United States Patent
Olsen et al.

(10) Patent No.: US 7,335,334 B2
(45) Date of Patent: Feb. 26, 2008

(54) ACTIVE AIR REMOVAL FROM AN EXTRACORPOREAL BLOOD CIRCUIT

(75) Inventors: Robert W. Olsen, Plymouth, MN (US); Walter L. Carpenter, Minneapolis, MN (US); John B. Dickey, Woods Cross, UT (US); Mark D. Stringham, Salt Lake City, UT (US)

(73) Assignee: Medtronic, Inc., Minneapolis, MN (US)

( * ) Notice: Subject to any disclaimer, the term of this patent is extended or adjusted under 35 U.S.C. 154(b) by 409 days.

(21) Appl. No.: 10/743,599

(22) Filed: Dec. 22, 2003

(65) Prior Publication Data

US 2004/0220509 A1    Nov. 4, 2004

Related U.S. Application Data

(60) Provisional application No. 60/440,005, filed on Jan. 14, 2003, provisional application No. 60/515,619, filed on Oct. 30, 2003.

(51) Int. Cl.
  *A61M 1/14*   (2006.01)
  *A61M 37/00*  (2006.01)
  *C02F 1/44*   (2006.01)
  *B01D 53/22*  (2006.01)

(52) U.S. Cl. .................. 422/45; 210/645; 604/4.01; 604/6.09; 604/6.14; 261/DIG. 28; 422/44

(58) Field of Classification Search ...... 604/4.01–5.01, 604/6.09, 6.1, 6.11, 6.14–6.16, 7, 65–67, 604/27, 30, 80, 264, 45; 422/44–45; 210/645, 210/416.1, 500.21, 739, 746; 248/689, 122.1, 248/674, 676; 261/DIG. 28

See application file for complete search history.

(56) References Cited

U.S. PATENT DOCUMENTS 3,507,395 A   4/1970   Bentley (Continued)

FOREIGN PATENT DOCUMENTS

DE   4326886 A1   2/1995

(Continued)

OTHER PUBLICATIONS

*Journal of Extra-Corporeal Technology*: "Rapid Pediatric Cardiopulmonary Support System," J.W. Ojito, et al., 1997;29(2):96-99.

(Continued)

*Primary Examiner*—Tatyana Zalukaeva
*Assistant Examiner*—Leslie R. Deak
(74) *Attorney, Agent, or Firm*—Mike Jaro; Jeffrey J. Hohenshell

(57) ABSTRACT

A disposable, integrated extracorporeal blood circuit employed during cardiopulmonary bypass surgery performs gas exchange, heat transfer, and microemboli filtering functions in a way as to conserve volume, to reduce setup and change out times, to eliminate a venous blood reservoir, and to substantially reduce blood-air interface. Blood from the patient or prime solution is routed through an air removal device that is equipped with air sensors for detection of air. An active air removal controller removes detected air from blood in the air removal device. A disposable circuit support module is used to mount the components of the disposable, integrated extracorporeal blood circuit in close proximity and in a desirable spatial relationship to optimize priming and use of the disposable, integrated extracorporeal blood circuit. A reusable circuit holder supports the disposable circuit support module in relation to a prime solution source, the active air removal controller and other components.

53 Claims, 24 Drawing Sheets

U.S. PATENT DOCUMENTS

| | | | |
|---|---|---|---|
| 3,929,414 A | 12/1975 | Leonard | 23/258.5 |
| 4,061,470 A | 12/1977 | Leonard | 25/258.5 |
| 4,185,629 A | 1/1980 | Cullis et al. | |
| 4,186,565 A | 2/1980 | Toledo-Pereyra | 62/306 |
| 4,205,677 A | 6/1980 | Engstrom | 128/276 |
| 4,243,531 A | 1/1981 | Crockett et al. | 210/188 |
| 4,370,983 A | 2/1983 | Lichtenstein | 128/630 |
| 4,402,687 A | 9/1983 | Denty et al. | 604/319 |
| 4,411,783 A | 10/1983 | Dickens et al. | |
| 4,416,658 A | 11/1983 | Numazawa et al. | 604/48 |
| 4,418,565 A | 12/1983 | St. John | 73/19 |
| 4,424,190 A | 1/1984 | Mather, III et al. | 422/46 |
| 4,436,620 A | 3/1984 | Bellotti et al. | 210/90 |
| 4,479,761 A | 10/1984 | Bilstad et al. | 417/395 |
| 4,479,762 A | 10/1984 | Bilstad et al. | 417/395 |
| 4,490,331 A | 12/1984 | Steg, Jr. | 422/46 |
| 4,540,399 A | 9/1985 | Litzie et al. | 607/4 |
| 4,572,724 A | 2/1986 | Rosenberg et al. | 55/159 |
| 4,573,992 A | 3/1986 | Marx | 604/408 |
| 4,599,093 A | 7/1986 | Steg, Jr. | 55/16 |
| 4,607,520 A | 8/1986 | Dam | 73/19 |
| 4,610,656 A | 9/1986 | Mortensen | 604/4 |
| 4,622,032 A | 11/1986 | Katsura et al. | 604/122 |
| 4,651,555 A | 3/1987 | Dam | 73/19 |
| 4,676,771 A | 6/1987 | Henke | 604/4 |
| 4,710,165 A | 12/1987 | McNeil et al. | |
| 4,722,224 A | 2/1988 | Scheller et al. | 73/599 |
| 4,734,269 A | 3/1988 | Clarke et al. | 422/310 |
| 4,758,337 A | 7/1988 | Köhn et al. | |
| 4,828,543 A | 5/1989 | Weiss et al. | 604/4 |
| 4,850,954 A | 7/1989 | Charvin | 604/4 |
| 4,923,438 A | 5/1990 | Vasconcellos et al. | |
| 4,975,247 A | 12/1990 | Badolato et al. | 422/48 |
| 4,997,464 A | 3/1991 | Kopf | |
| 5,011,469 A | 4/1991 | Buckberg et al. | 604/4 |
| 5,021,048 A | 6/1991 | Buckholtz | 604/151 |
| 5,039,482 A | 8/1991 | Panzani et al. | 422/46 |
| 5,049,146 A | 9/1991 | Bringham et al. | 604/4 |
| 5,055,198 A | 10/1991 | Shettigar | |
| 5,061,236 A | 10/1991 | Sutherland et al. | 604/4 |
| 5,069,661 A | 12/1991 | Trudell | 604/4 |
| 5,074,839 A | 12/1991 | Choksi et al. | |
| 5,110,548 A | 5/1992 | Montevecchi | 422/48 |
| 5,147,186 A | 9/1992 | Buckholtz | 417/420 |
| 5,158,533 A | 10/1992 | Strauss et al. | 604/4 |
| 5,162,102 A | 11/1992 | Nogawa et al. | |
| 5,205,153 A | 4/1993 | Hlavinka et al. | 73/79.03 |
| 5,238,655 A | 8/1993 | Laible et al. | 422/101 |
| 5,266,265 A | 11/1993 | Raible | 422/46 |
| 5,270,005 A | 12/1993 | Raible | 422/46 |
| 5,305,982 A | 4/1994 | Tamari | 281/5 |
| 5,308,314 A | 5/1994 | Fukui et al. | 604/4 |
| 5,308,320 A | 5/1994 | Safar et al. | 604/4 |
| 5,312,589 A | 5/1994 | Reeder et al. | 422/45 |
| 5,334,136 A | 8/1994 | Schwarz et al. | 604/4 |
| 5,336,051 A | 8/1994 | Tamari | 417/19 |
| 5,346,621 A | 9/1994 | Haworth et al. | 210/645 |
| 5,372,593 A | 12/1994 | Boehringer et al. | 609/319 |
| 5,376,334 A | 12/1994 | Haworth et al. | 422/46 |
| 5,382,227 A | 1/1995 | Riquier | 604/4 |
| 5,395,468 A | 3/1995 | Juliar et al. | 156/169 |
| 5,411,706 A | 5/1995 | Hubbard et al. | 422/46 |
| 5,419,769 A | 5/1995 | Devlin et al. | 604/119 |
| 5,429,058 A | 7/1995 | Miller et al. | |
| 5,462,619 A | 10/1995 | Haworth et al. | 156/172 |
| 5,540,653 A | 7/1996 | Schock et al. | 604/7 |
| 5,573,502 A | 11/1996 | LeCocq et al. | 604/4 |
| 5,573,526 A | 11/1996 | Hess | 604/408 |
| 5,588,816 A | 12/1996 | Abbott et al. | 417/479 |
| 5,632,894 A | 5/1997 | White et al. | 210/436 |
| 5,651,765 A | 7/1997 | Haworth et al. | 604/4 |
| 5,762,868 A | 6/1998 | Leonard | 422/46 |
| 5,766,480 A | 6/1998 | Cosentino et al. | 210/644 |
| 5,782,791 A | 7/1998 | Peterson et al. | 604/4 |
| 5,820,579 A | 10/1998 | Plotkin | 604/5 |
| 5,823,986 A | 10/1998 | Peterson | 604/4 |
| 5,837,905 A | 11/1998 | Strauss et al. | 73/861.63 |
| 5,876,611 A | 3/1999 | Shettigar | |
| 5,879,316 A | 3/1999 | Safar et al. | 604/4 |
| 5,931,646 A | 8/1999 | Nogawa et al. | |
| 5,958,338 A | 9/1999 | Lindsay et al. | 422/45 |
| 5,965,089 A | 10/1999 | Jarvik et al. | |
| 5,984,892 A | 11/1999 | Bedingham | |
| 6,017,493 A | 1/2000 | Cambron et al. | 422/44 |
| 6,071,258 A | 6/2000 | Dalke et al. | 604/5 |
| 6,083,198 A | 7/2000 | Afzal | |
| 6,105,912 A | 8/2000 | Lindsay et al. | 248/223.41 |
| 6,117,390 A | 9/2000 | Corey, Jr. | 422/45 |
| 6,200,276 B1 | 3/2001 | Biesel et al. | |
| 6,210,365 B1 | 4/2001 | Afzal | |
| 6,224,829 B1 | 5/2001 | Piplani | |
| 6,299,589 B1 | 10/2001 | Utterberg | |
| 6,302,860 B1 | 10/2001 | Gremel et al. | 604/60.9 |
| 6,306,346 B1 | 10/2001 | Lindsay | 422/45 |
| 6,315,751 B1 | 11/2001 | Cosgrove et al. | 604/5.01 |
| 6,337,049 B1 * | 1/2002 | Tamari | 422/44 |
| 6,368,557 B1 | 4/2002 | Piplani et al. | 422/45 |
| 6,379,618 B1 | 4/2002 | Piplani et al. | 422/45 |
| 6,387,323 B1 | 5/2002 | Afzal et al. | 422/45 |
| 6,428,742 B1 | 8/2002 | Lemken | |
| 6,451,257 B1 | 9/2002 | Flamer | 422/44 |
| 6,454,999 B1 | 9/2002 | Farhangnia et al. | 422/45 |
| 6,495,366 B1 | 12/2002 | Briggs | |
| 6,503,450 B1 | 1/2003 | Afzal | |
| 6,524,267 B1 | 2/2003 | Gremel et al. | |
| 6,559,132 B1 | 5/2003 | Holmer | 514/56 |
| 6,607,698 B1 | 8/2003 | Spears et al. | |
| 6,689,315 B2 | 2/2004 | Linker | |
| 6,716,189 B1 | 4/2004 | Jarvik et al. | |
| 6,730,267 B2 * | 5/2004 | Stringer et al. | 422/45 |
| 6,824,524 B1 | 11/2004 | Favre | |
| 6,890,316 B2 | 5/2005 | Rawles et al. | |
| 6,946,099 B2 | 9/2005 | Vijay et al. | |
| 7,022,284 B2 | 4/2006 | Brian et al. | |
| 2002/0044889 A1 | 4/2002 | Aboul-Hosn et al. | 422/45 |
| 2002/0057989 A1 | 5/2002 | Afzal et al. | 422/45 |
| 2002/0110485 A1 | 8/2002 | Stringer et al. | 422/45 |
| 2002/0114731 A1 | 8/2002 | Stringer et al. | 422/44 |
| 2002/0136662 A1 | 9/2002 | Myrick et al. | 422/45 |
| 2002/0151804 A1 | 10/2002 | Gelfand et al. | |
| 2002/0176797 A1 | 11/2002 | Roberts et al. | 422/44 |
| 2002/0176798 A1 | 11/2002 | Linker et al. | 422/45 |
| 2003/0060421 A1 | 3/2003 | Hesson et al. | 514/23 |
| 2003/0091470 A1 | 5/2003 | Patterson et al. | 422/45 |
| 2003/0095892 A1 | 5/2003 | Patterson et al. | 422/45 |
| 2003/0135152 A1 | 7/2003 | Kollar | |
| 2003/0161759 A1 | 8/2003 | Myrick et al. | 422/45 |
| 2003/0163078 A1 | 8/2003 | Fallen et al. | 604/6.01 |
| 2003/0194348 A1 | 10/2003 | Divino, Jr. et al. | 422/45 |
| 2003/0204127 A1 | 10/2003 | Rawles et al. | 600/16 |
| 2003/0215356 A1 | 11/2003 | Patterson et al. | 422/45 |
| 2003/0231982 A1 | 12/2003 | Myrick et al. | 422/45 |
| 2004/0009097 A1 | 1/2004 | Stringer et al. | 422/45 |
| 2004/0084358 A1 | 5/2004 | O'Mahony et al. | |
| 2004/0195178 A1 | 10/2004 | Carpenter et al. | |
| 2004/0197223 A1 | 10/2004 | Olsen et al. | |
| 2004/0217054 A1 | 11/2004 | Olsen et al. | |
| 2004/0220509 A1 | 11/2004 | Olsen et al. | |
| 2005/0063860 A1 | 3/2005 | Carpenter et al. | |

FOREIGN PATENT DOCUMENTS

| | | |
|---|---|---|
| EP | 0351980 B1 | 4/1994 |
| EP | 0786261 A2 | 7/1997 |

| | | |
|---|---|---|
| EP | 1036567 A2 | 2/2001 |
| EP | 1 166 806 | 1/2002 |
| EP | 1180374 A1 | 2/2002 |
| EP | 1182452 A2 | 2/2002 |
| EP | 1 374 929 | 1/2004 |
| IT | MO2005A000243 | 9/2005 |
| IT | MO2005A000244 | 9/2005 |
| WO | WO 96/24397 | 8/1996 |
| WO | WO 00/12155 | 3/2000 |
| WO | WO 00/47248 | 8/2000 |
| WO | 02/26288 | 4/2002 |
| WO | WO 02/26288 | 4/2002 |
| WO | WO 02/064013 | 8/2002 |
| WO | WO 02/100475 | 12/2002 |
| WO | WO 03/058608 | 7/2003 |
| WO | WO 03/066134 | 8/2003 |
| WO | WO 2004/000391 | 12/2003 |
| WO | WO 2004/064896 | 8/2004 |
| WO | 2005/067998 | 7/2005 |

OTHER PUBLICATIONS

*Pediatric Cardiac Anesthia*: "Extracorporeal Circulation and Circulatory Assist Devices in the Pediatric Patient," Frank H. Kern, et al., 1997; 3rd Ed.:219-258.

*Journal of Extra-Corporeal Technology*: "Experimental Use Of An Ultra-Low Prime Neonatal Cardiopulmonary Bypass Circuit Utilizing Vacuum-Assisted Venous Drainage," Edward Darling, et al., 1998; 30(4):184-89.

*Perfusion*: "Minimizing The Bypass Circuit: A Rational Step In The Development Of Paediatric Perfusion," Martin Elliott, 1993; 8:81-86.

*Zasshi Journal* (English Abstract): "The Indications and Limitations of Open Heart Surgery Without Homologous Blood Transfusion in Children and Infants," Masanobu Maeda, et al., 1994; 42:1-7.

*Journal of Cardiovascular Surgery*: "Clear Prime for Infant Cardiopulmonary Bypass: A Miniaturized Circuit," Eric Wabeke, et al., 1988; 29(2):117-22.

*Journal of Extra-Corporeal Technology*: "A Modification Of The Sarns Conducer Heat Exchanger As A Low Prime Pediatric Cardioplegia System," Ronald Gorney, et al., 1994; 26(1):37-39.

*International Anesthesiology Clinics*: "Pediatric Cardiopulmonary Bypass: A Review of Current Practice," Robert C. Groom, et al., 1996; 34:141-63.

*Journal of Extra-Corporeal Technology*: "Micro-Prime Circuit Facilitating Minimal Blood Use During Infant Perfusion," Charles M. Tyndal Jr., et al., 1987; 19(3):352-57.

*Ann. Thoracic Surgery*: "A Venous Reservoir For Cardiopulmonary Bypass In Newborns And Small Infants," John L. Ochsner, et al., 1988; 45:686.

*Proc. Eur. Society Artificial Internal Organs*: "Automation of Cardiopulmonary Bypass for Open Heart Surgery," P.H. Mook, et al., 1978; 5:234-37.

*Perfusion*: "Mini-Circuit Cardiopulmonary Bypass With Vacuum Assisted Venous Drainage: Feasibility Of An Asanguineous Prime In the Neonate," Christine L. Lau, et al., 1999; 14:389-96.

*Artificial Organs*: "A Novel Technique for Cardiopulmonary Bypass using Vacuum System for Venous Drainage with Pressure Relief Valve: An Experimental Study," Satoshi Taketani, et al., 1998; 22(4):337-41.

*Perfusion*: "Paediatric Perfusion Practice in North America: An Update," Robert C. Groom, et al., 1995; 10:393-401.

*Perfusion*: "Single Pump Mechanically Aspirated Venous Drainage (SPMAVD) for Cardiac Reoperation," 1996; 11:351-353 (Applicants only have p. 351).

*Ann. Thoracic Surg*: "Minimally Invasive Coronary Artery Bypass Grafting," Tea E. Acuff, M.D., et al., 1996; 61:135-7 (Applicants only have p. 135).

*Ann. Thoracic Surg*.: "Transpericardial Inferior Vena Caval Cannulation in Thoracic Aorta Operations," Eugenio Neri, M.D., et al., 1996; 62:1208-1209 (Applicants only have p. 1208).

*Ann. Thoracic Surg.*: "Minimally Invasive Valve Operations," Delos M. Cosgrove III, M.D., et al., 1998;65:1535-9 (Applicants only have p. 1535).

*Ann. Thoracic Surg.*: "Augmented Femoral Venous Return," Lynn Solomon, M.D., et al., 1993; 55:1262-3 (Applicants only have p. 1262).

Drawing provided by Miami Children's Hospital, drawn on Jul. 7, 1997.

Specification Sheets of a venous assisted CB circuit, specification sheets sent between Miami Children's Hospital and Medtronic, Inc., earliest date is Dec. 16, 1998 (7 pages).

Specification Sheets of a hybrid CB circuit, specification sheets sent between Miami Children's Hospital and Medtronic, Inc., earliest date is Jun. 20, 1997.

Email relating to augmented venous return sent to PerfList@aol.com, PerfList@aol.com is a multiple recipient medical informational email group, sent on Apr. 27, 1997.

Email relating to augmented venous return and minimally invasive procedures sent to PerfList@aol.com, PerfList@aol.com is a multiple recipient medical informational email group, sent on Apr. 27, 1997.

Email relating to venous drainage sent from Brian Crawford CCP to Jorge Ojito on Apr. 28, 1997.

Email relating to augmented venous return sent by Jorge Ojito on Apr. 26, 1997.

*Ann. Thoracic Surgery*: "Assisted Venous Drainage Cardiopulmonary Bypass in Congenital Heart Surgery," Jorge Ojito, et al., 2001; 71:1267-72.

Ann. Thoracic Surgery: "Rapid Cardiopulmonary Support for Children with Complex Congenital Heart Disease," Jeffrey P. Jacobs, et al., 2000;70:742-50.

"Minimally Invasive & Bypass" computer search results, 1998.

"Minimally Invasive & Valve" computer search results, 1998.

"Intersept® Custom Tubing Pack with Carmeda® BioActive Surface" product label, 2003.

Facsimile transmission sheet from Elly Wierenga, Medtronic, Inc., regarding Carmeda® Data Analysis, Sep. 14, 1998.

"Venous Pull Circuit" diagram.

*Journal of Thoracic and Cardiovascular Surgery* Copyright and Conflict of Interest Statement regarding manuscript entitled "Assisted Venous Drainage Cardiopulmonary Bypass: (AVDCPB) An Alternative Technique in Minimally Invasive Congenital Surgery" signature page, signed by Jorge Ojito, Nov. 25, 1998.

May 4, 1999 correspondence from John A. Waldhausen, M.D., *The Journal of Thoracic and Cardiovascular Surgery*, to Redmond Burke, M.D. regarding his manuscript entitled "Assisted Venous Drainage Cardiopulmonary Bypass: an Alternative Technique in Minimally Invasive Congenital Cardiac Surgery."

Jun. 28, 2000 correspondence from L. Henry Edmunds, Jr., M.D., Editor, *The Annals of Thoracic Surgery*, to Redmond P. Burke, M.D. regarding his paper entitled "Assisted Venous Drainage Cardiopulmonary Bypass: Safety and Efficacy in Congenital Heart Surgery."

Program and certificate of participation of Jorge Ojito at Sociedad Chilenade Circulacion Extracorporea, Vina del Mar, Chile, Nov. 12-15, 1998.

"Assisted Venous Drainage Cardiopulmonary Bypass: Safety and Efficacy in Congenital Heart Surgery" presentation, Jorge Ojito.

Certificates of participation by Jorge Ojito Jornados Sobre Perfusion Pediatrica y Asistencia Circulatoria Mecanica, Buenos Aires, Argentina, Nov. 17, 1998.

Cardiologia program, Caracas, Venezuela, Jun. 6-10, 2000.

"Assisted Venous Drainage Cardiopulmonary Bypass: Safety and Efficacy in Congenital Heart Surgery," presented by Jorge Ojito, Mechanisms of Perfusion XVI, Lake Buena Vista, Florida, May 17-20, 2001.

"Assisted Venous Drainage During CPB: Safety and Efficacy in Congenital Heart Surgery," presented by Jorge Ojito, The 38th Annual Scientific Meeting of Japanese Society of Pediatric Cardiology and Cardiac Surgery, 2002.

Comparison of claims in United States Patent No. 6,302,860 (Gremel, et al.) and United States Patent No. 6,337,049 (Tamari).

Declaration of Jorge Ojito in the matter of United States Patent Nos. 6,302,860 and 6,524,267, Aug. 2003.
*Curriculum Vitae* of Jorge Ojito.
Declaration of Yehuda Tamari in the matter of United States Patent Nos. 6,302,860 and 6,524,267.
*Curriculum vitae* of Yehuda Tamari.
Documents labeled CV 038666-CV 038724 produced in *CardioVention, Inc. v. Medtronic, Inc.*, U.S. District Court, District of Minnesota, Civil File No. 04-CV-02669 (59 pages).
Agenda for New Era 2002 Perfusion Mini-Symposium held in Jan. 2002 (1 page).
Declaration of Jorge Ojito in the matter of United States District Court, District of Minnesota, Civil File No. 04-CV-02669, *CardioVention, Inc. v. Medtronic, Inc.*, executed Nov. 22, 2005.
Curriculum Vitae of Jorge Ojito, Exhibit 1 to the Declaration of Jorge Ojito executed Nov. 22, 2005 (5 pages).
Drawing of the Venous Pull Circuit dated Jul. 1997, Exhibit 2 to the Declaration of Jorge Ojito executed Nov. 22, 2005 (1 page).
Drawing from Katsura U.S. Patent No. 4,919,802, issued on Apr. 24, 1990, Exhibit 3 to the Declaration of Jorge Ojito executed Nov. 22, 2005 (2 pages).
Advertising brochure from COBE Cardiovascular for the Century Perfusion System circa 1997, Exhibit 4 to the Declaration of Jorge Ojito executed Nov. 22, 2005 (4 pages).
Two pictures of an ultrasonic air sensor allegedly used on the Venous Pull Circuit in 1997 and 1998, Exhibit 5 to the Declaration of Jorge Ojito executed Nov. 22, 2005 (2 pages).
Picture of the Venous Pull Circuit, Exhibit 6 to the Declaration of Jorge Ojito executed Nov. 22, 2005 (1 page).
Ojito, et al., "Assisted Venous Drainage Cardiopulumonary Bypass in Congenital Heart Surgery," Ann. Thorac. Surg., 2001;71:1267-72, Exhibit 7 to the Declaration of Jorge Ojito executed Nov. 22, 2005 (5 pages).
Custom Tubing Pack Specification, Exhibit 8 to the Declaration of Jorge Ojito executed Nov. 22, 2005 (5 pages).
Medtronic Cardiopulmonary personnel business cards, Exhibit 9 to the Declaration of Jorge Ojito executed Nov. 22, 2005 (1 page).
Circulacion Extracorporea presentation brochure, Exhibit 10 to the Declaration of Jorge Ojito executed Nov. 22, 2005 (4 pages).
Certificate of participation of Jorge Ojito, Exhibit 11 to the Declaration of Jorge Ojito executed Nov. 22, 2005 (2 pages).
AmSECT Region XI Annual Fall Meeting agenda, Exhibit 12 to the Declaration of Jorge Ojito executed Nov. 22, 2005 (2 pages).
PowerPoint presentation regarding Assisted Venous Drainage Cardiopulmonary Bypass: Safety and Efficacy in Congenital Heart Surgery, Jorge W. Ojito, Exhibit 13 to the Declaration of Jorge Ojito executed Nov. 22, 2005 (48 pages).
United States Patent 6,302,860, Exhibit 14 to the Declaration of Jorge Ojito executed Nov. 22, 2005 (5 pages).
United States Patent 6,524,267, Exhibit 15 to the Declaration of Jorge Ojito executed Nov. 22, 2005 (5 pages).
Gremel I patent comparison chart, Exhibit 16 to the Declaration of Jorge Ojito executed Nov. 22, 2005 (4 pages).
Gremel II patent comparison chart, Exhibit 17 to the Declaration of Jorge Ojito executed Nov. 22, 2005 (5 pages).
Mueller, et al., "A new concept of integrated cardiopulmonary bypass circuit," European Journal of Cardio-thoracic Surgery 21 (2002) 840-846.
Morita, et al., "Closed Circuit Cardiopulmonary Bypass with Centrifugal Pump for Open-Heart Surgery: New Trial for Air Removal," Artificial Organs 2000; 24(6):442-445.
Jegger, et al., "Introduction & Description of CardioVention's CORx System. A replacement technology for traditional cardiopulmonary bypass," Dept of Cardiovascular Surgery, Centre Hospitalier Universitaire Vaudois (CHUV), Switzerland (9 pages).
Instructions for Use CORx System, CardioVention, Inc., Santa Clara, CA, 2001 (21 pages).
Complaint in *CardioVention, Inc. v. Medtronic, Inc.*, U.S. District Court, District of Minnesota, Civil File No. 04-CV-02669 (16 pages).
Declaration of Ben F. Brian, Ph.D., in *CardioVention, Inc. v. Medtronic, Inc.*, U.S. District Court, District of Minnesota, Civil File No. 04-CV-02669 (13 pages).
Plaintiff's Answers and Objections to Defendant's First Set of Interrogatories to Plaintiff in *CardioVention, Inc. v. Medtronic, Inc.*, U.S. District Court, District of Minnesota, Civil File No. 04-CV-02669 (11 pages).
Memorandum of Law & Order in *CardioVention, Inc. v. Medtronic, Inc.*, U.S. District Court, District of Minnesota, Civil File No. 04-CV-02669 (18 pages).
CardioVention CORx System 510(k) Summary dated Jun. 16, 2001 (8 pages).
Matayoshi, et al., "Development of a Completely Closed Circuit Using an Air Filter in a Drainage Circuit for Minimally Invasive Cardiac Surgery," Artificial Organs, 24(6):454-458, 2000.
McCusker, et al., "High-flow femoro-femoral bypass utilizing small cannulae and a centrifugal pump on the venous side," Perfusion 1992; 7:295-300.
Hatteland, "Doppler Ultrasound Application in Cardiology and Cardiac Surgery," from the Thoracic Surgical Clinic, Karolinska Institutet, Stockholm, Sweden, 1985 (6 pages).
Memorandum in Support of Plaintiff's Motion to Compel Production of Documents in *CardioVention, Inc. v. Medtronic, Inc.*, U.S. District Court, District of Minnesota, Civil File No. 04-CV-02669 (22 pages).

* cited by examiner 138A, 138B, 138C, 138D 138A, 138B, 138C, 138D

ACTIVE AIR REMOVAL FROM AN EXTRACORPOREAL BLOOD CIRCUIT

This application claims benefit of Provisional No. 60/440,005 filed Jan. 14, 2003, and Provisional No. 60/515,619 filed Oct. 30, 2003.

REFERENCE TO RELATED APPLICATIONS

Reference is hereby made to commonly assigned co-pending U.S. patent application Ser. No. 10/743,598 filed on an even date herewith EXTRACORPOREAL BLOOD CIRCUIT AIR REMOVAL SYSTEM AND METHOD in the names of Robert W. Olsen, Walter L. Carpenter, John B. Dickey, Frederick A. Shorey, Laura A. Yonce, and Mark D. Stringham; Ser. No. 10/743,373 filed on an even date herewith for DISPOSABLE, INTEGRATED, EXTRACORPOREAL BLOOD CIRCUIT in the names of Walter L. Carpenter, Robert W. Olsen, Stefanie Heine, Frederick A. Shorey, and Laura A. Yonce; Ser. No. 10/743,357 filed on an even date herewith for EXTRACORPOREAL BLOOD CIRCUIT PRIMING SYSTEM AND METHOD in the names of Walter L. Carpenter, Robert W. Olsen, Frederick A. Shorey, Mark G. Bearss, Bruce R. Jones, and Laura A. Yonce; and Ser. No. 10/743,116 filed on an even date herewith for ACTIVE AIR REMOVAL OPERATING MODES OF AN EXTRACORPOREAL BLOOD CIRCUIT in the names of Robert W. Olsen, Walter L. Carpenter, John B. Dickey, and Mark D. Stringham.

FIELD OF THE INVENTION

This invention relates to extracorporeal blood circuits, systems, and methods of use and more particularly to a disposable, integrated extracorporeal blood circuit comprising a plurality of components and lines interconnecting components supported spatially in 3-D space by a component organizing and supporting system, the components including an air removal device, particularly a Venous Air Removal Device (VARD), from which air is purged under the control of a reusable Active Air Removal (AAR) controller operable in a Self-Test Mode, a Standby Mode, and an Automatic Mode.

BACKGROUND OF THE INVENTION

Conventional cardiopulmonary bypass uses an extracorporeal blood circuit that is to be coupled between arterial and venous cannulae and includes a venous drainage or return line, a venous blood reservoir, a blood pump, an oxygenator, an arterial filter, and blood transporting tubing or "lines", ports, and valves interconnecting these components. Prior art, extracorporeal blood circuits as schematically depicted in FIGS. 1-3 and described in commonly assigned U.S. Pat. No. 6,302,860, draw venous blood of a patient 10 during cardiovascular surgery through the venous cannula (not shown) coupled to venous return line 12, oxygenates the blood, and returns the oxygenated blood to the patient 10 through an arterial line 14 coupled to an arterial cannula (not shown). Cardiotomy blood and surgical field debris that is aspirated by a suction device 16 is pumped by cardiotomy pump 18 into a cardiotomy reservoir 20.

Air can enter the extracorporeal blood circuit from a number of sources, including around the venous cannula, through loose fittings of the lines or ports in the lines, and as a result of various unanticipated intra-operative events. It is necessary to minimize the introduction of air in the blood in the extracorporeal blood circuit and to remove any air that does accumulate in the extracorporeal blood circuit before the filtered and oxygenated blood is returned to the patient through the arterial cannula to prevent injury to the patient. Moreover, if a centrifugal blood pump is used, a large volume of air accumulating in the venous line of the extracorporeal blood circuit can accumulate in the blood pump and either de-prime the blood pump and deprive it of its pumping capability or be pumped into the oxygenator and de-prime the oxygenator, inhibiting oxygenation of the blood.

In practice, it is necessary to initially fill the cannulae with the patient's blood and to prime (i.e., completely fill) the extracorporeal blood circuit with a bio-compatible prime solution before the arterial line and the venous return lines are coupled to the blood filled cannulae inserted into the patient's arterial and venous systems, respectively. The volume of blood and/or prime solution liquid that is pumped into the extracorporeal blood circuit to "prime" it is referred to as the "prime volume". Typically, the extracorporeal blood circuit is first flushed with $CO_2$ prior to priming. The priming flushes out any extraneous $CO_2$ gas from the extracorporeal blood circuit prior to the introduction of the blood. The larger the prime volume, the greater the amount of prime solution present in the extracorporeal blood circuit that mixes with the patient's blood. The mixing of the blood and prime solution causes hemodilution that is disadvantageous and undesirable because the relative concentration of red blood cells must be maintained during the operation in order to minimize adverse effects to the patient. It is therefore desirable to minimize the volume of prime solution that is required.

In one conventional extracorporeal blood circuit of the type depicted in FIG. 1, venous blood from venous return line 12, as well as de-foamed and filtered cardiotomy blood from cardiotomy reservoir 20, are discharged into a venous blood reservoir 22. Air entrapped in the venous blood rises to the surface of the blood in venous blood reservoir 22 and is vented to atmosphere through a purge line 24. The purge line 24 is typically about a 6 mm ID flexible tubing, and the air space above the blood in venous blood reservoir 22 is substantial. A venous blood pump 26 draws blood from the venous blood reservoir 22 and pumps it through an oxygenator 28, an arterial blood filter 30, and the arterial line 14 to return the oxygenated and filtered blood back to the patient's arterial system via the arterial cannula coupled to the arterial line 14.

A negative pressure with respect to atmosphere is imposed upon the mixed venous and cardiotomy blood in the venous blood reservoir 22 as it is drawn by the venous blood pump 26 from the venous blood reservoir 22. The negative pressure causes the blood to be prone to entrain air bubbles. Although arterial blood filters, e.g., arterial blood filter 30, are designed to capture and remove air bubbles, they are not designed to handle larger volumes of air that may accumulate in the extracorporeal blood circuit. The arterial blood filter 30 is basically a bubble trap that traps any air bubbles larger than about 20-40 microns and discharges the air to atmosphere through a typically about 1.5 mm ID purge line 32. The arterial filter 30 is designed to operate at positive blood pressure provided by the venous blood pump 26. The arterial blood filter 30 cannot prevent accumulation of air in the venous blood pump 26 and the oxygenator 28 because it is located in the extracorporeal blood circuit downstream from them.

As shown in FIG. 2 from the above-referenced '860 patent, it has been proposed to substitute an assisted venous return (AVR) extracorporeal blood circuit for the conventional extracorporeal blood circuit of the type depicted in FIG. 1, whereby venous blood is drawn under negative pressure from the patient's body. The arterial blood filter 30 is moved into the venous return line 12 upstream of the venous blood pump 26 to function as a venous blood filter 30'. The venous blood reservoir 22, which accounts for a major portion of the prime volume of the extracorporeal blood circuit, is thereby eliminated. De-foamed and filtered cardiotomy blood from cardiotomy reservoir 20 is drained into the venous blood filter 30, and venous blood in venous return line 12 and the venous cannula coupled to it is pumped through the venous blood filter 30. Exposure of the venous blood to air is reduced because the venous blood filter 30' does not have an air space between its inlet and outlet (except to the extent that air accumulates above the venous blood inlet), as the venous blood reservoir 22 does. Suction is provided in the venous return line 12 through the negative pressure applied at the outlet of venous blood filter 30' by the venous blood pump 26 to pump the filtered venous blood through the oxygenator 28 and into the arterial blood line 14 to deliver it back to patient 10. Again, the venous blood filter 30' is basically a bubble trap that traps any air bubbles larger than about 20-40 microns and discharges the air through a typically about 1.5 mm ID purge line 32.

The arterial blood filter 30 is also relocated with respect to the cardiotomy reservoir 20 and modified to function as a venous blood filter 30' in the extracorporeal blood circuit shown in FIG. 3. Evacuation of air from venous blood received through venous return line 12 is facilitated by increasing the size of the purge port 34 of the venous blood filter 30' to accept a larger diameter purge line 42, e.g. a 6 mm ID line, rather than the 1.5 mm ID line. A vacuum greater than that normally used for venous drainage is applied through purge line 42 to the purge port 34 to actively purge air from venous blood filter 30. The cardiotomy reservoir 20 is at ambient pressure but is conveniently purged by the same vacuum that purges air from venous blood filter 30. A valve 36, e.g., a one-way check valve, is incorporated into the purge port 34 or purge line 42 to prevent air or blood purged from the cardiotomy reservoir 20 from being drawn into venous blood filter 30' by the negative pressure in venous blood filter 30' when the purging vacuum is not active.

As shown in FIG. 4 from the above-referenced '860 patent, venous blood is drawn through the upper venous blood inlet 44 of venous blood filter 30', down through the filter 46 and a screen or other conventional bubble trapping device (not shown), and out the venous blood outlet 48 by the venous blood pump 26. The purge port 34 is located above the venous blood inlet 44, and air that is separated out by the screen or other conventional bubble trapping device accumulates in the space 50 above the venous blood inlet 44. An air sensor 38 is disposed adjacent the purge port 34 that generates a sensor signal or modifies a signal parameter in the presence of air in the space 50. The sensor signal is processed by circuitry in a controller (not shown) that applies the vacuum to the purge line 42 to draw the accumulated air out of the space 50. The vacuum is discontinued when the sensor signal indicates that venous blood is in the space 50. Thus, an "Active Air Removal" (AAR) system is provided to draw the accumulated air out of space 50 when, and only when, air present in the space 50 is detected by air sensor 38 to purge the air and to prevent venous blood filling space 50 from being aspirated out the purge line 42 by the purging vacuum. The purging vacuum may be produced by a pump 40, or it may be produced by connecting the purge line 42 to the vacuum outlet conventionally provided in operating rooms.

Again, suction is provided in the venous return line 12 through the negative pressure applied at the outlet 48 of venous blood filter 30' by the venous blood pump 26 to pump the filtered venous blood through the oxygenator 28 and into the arterial blood line 14 to deliver it back to patient 10. De-foamed and filtered cardiotomy blood is also pumped by venous blood pump 26 from cardiotomy reservoir 20 through the oxygenator 28 and into the arterial blood line 14 to deliver it back to patient 10.

While the AVR extracorporeal blood circuit illustrated in FIGS. 3 and 4, and particularly the use of the AAR method and system, represents a significant improvement in extracorporeal circuits, its implementation can be further refined and improved. A need remains for an AAR system and method that optimizes the air sensor and its functions and that detects and responds to error conditions and faults that can arise over the course of prolonged surgical use.

Moreover, the typical prior art extracorporeal blood circuit, e.g. the above-described extracorporeal blood circuits of FIGS. 1-3, has to be assembled in the operating room from the above-described components, primed, and monitored during the surgical procedure while the patient is on bypass. This set-up of the components can be time-consuming and cumbersome and can result in missteps that have to be corrected. Therefore, a need remains for an extracorporeal blood circuit having standardized components and that can be set up for use using standardized setup procedures minimizing the risk of error.

The resulting distribution of the components and lines about the operating table can take up considerable space and get in the way during the procedure as described in U.S. Pat. No. 6,071,258, for example. The connections that have to be made can also introduce air leaks introducing air into the extracorporeal blood circuit. A need remains for a compact extracorporeal blood circuit that is optimally positioned in relation to the patient and involves making a minimal number of connections.

The lengths of the interconnected lines are not optimized to minimize prime volume and attendant hemodilution and to minimize the blood contacting surface area. A large blood contacting surface area increases the incidences of embolization of blood cells and plasma traversing the extracorporeal blood circuit and complications associated with immune response, e.g., as platelet depletion, complement activation, and leukocyte activation. Therefore, a need remains for a compact extracorporeal blood circuit having minimal line lengths and minimal blood contacting surface area.

Furthermore, a need remains for such a compact extracorporeal blood circuit with minimal blood-air interfaces causing air to be entrained in the blood. In addition, it is desirable that the components be arranged to take advantage of the kinetic assisted, venous drainage that is provided by the centrifugal venous blood pump in an AVR extracorporeal blood circuit employing an AAR system.

Occasionally, it becomes necessary to "change out" one or more of the components of the extracorporeal blood circuit during the procedure. For example, it may be necessary to replace a blood pump or oxygenator. It may be necessary to prime and flush the newly constituted extracorporeal blood circuit after replacement of the malfunctioning component. The arrangement of lines and connectors may make this very difficult to accomplish. A need therefore remains for a compact extracorporeal blood circuit that can be rapidly and easily substituted for a malfunctioning extracorporeal blood circuit and that can be rapidly primed.

Consequently, a need remains for a extracorporeal blood circuit that is compactly arranged in the operating room, that takes advantage of kinetic assist, and is small in volume to minimize the required prime volume and to minimize the blood contacting surface area and blood-air interfaces. Moreover, a need remains for such an extracorporeal blood circuit that is simple to assemble in relation to other components, that provides for automatic monitoring of blood flow and other operating parameters, that can be simply and rapidly primed, that provides for detection and removal of air from the extracorporeal blood circuit, and that facilitates change out of the extracorporeal blood circuit or components employed with it during the procedure.

SUMMARY OF THE INVENTION

The present invention addresses at least some of these needs in unique and advantageous ways.

This invention relates to purging methods and systems for detecting and purging air from the components and lines of an extracorporeal blood circuit, particularly, a disposable, integrated extracorporeal blood circuit comprising a plurality of components and lines interconnecting components supported spatially in 3-D space. The purging system and method employ an air removal device incorporated into the extracorporeal blood circuit in which air accumulates and a reusable Active Air Removal (AAR) controller interconnected with the air removal device to purge the accumulated air therefrom.

The air removal device comprises a housing enclosing a chamber, an air removal device purge port through the housing to the chamber, and an air sensor supported by the air removal device housing. The air sensor generates an air sensor signal indicative of the absence or presence of air in the air removal device housing. An air removal device purge line is coupled to the air removal device purge port, the air removal device purge line extending to a purge line connector adapted to be coupled to a vacuum source to apply suction to the air removal device purge port to draw air therefrom.

A portion of the air removal purge line extends through a purge valve of the AAR controller. The purge valve is movable between a purge valve open position and a purge valve closed position. The purge valve is opened in response to an air sensor signal indicative of the presence of air in the air removal device chamber to allow air sensed in the air removal device to be purged through the purge line by the suction of the vacuum source. The AAR controller removes air accumulating in the air removal device chamber until fluid is sensed in the air removal purge line by a fluid in line (FIL) sensor. Various operating states and conditions are also monitored. Automatic air removal is inhibited, that is interrupted if already started or prevented if not started, by closure of the purge valve if an error condition of the purging system is detected. Mechanical opening of the purge valve is enabled at any time.

In a preferred embodiment, the AAR controller is operable in a Self-Test Mode, a Standby Mode, and an Automatic Mode. Air is automatically or manually drawn air from blood or prime solution circulating through the disposable, integrated extracorporeal blood circuit and accumulating in the air removal device. In such modes, various sensor output signals are examined to determine any error conditions or declared error states of the purging system comprising the AAR controller and the air removal device as well as other ambient conditions, e.g., absence of mains power and sufficient vacuum to draw air from the air removal device. The AAR controller generates displays of operating state and error messages and emits audible and visible Cautions and Alarms in response to detected error conditions.

In a preferred embodiment, the VARD is equipped with upper and lower air sensors for providing sensor signals when air accumulates in the VARD and needs to be removed through a VARD air removal purge line coupled to a VARD purge port.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
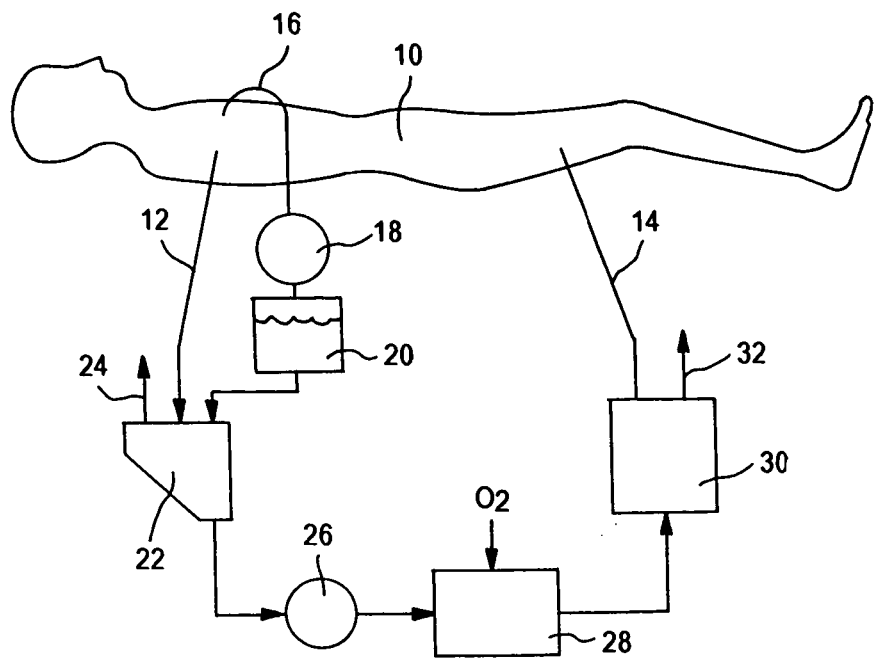
FIG. 1 is a schematic diagram of a first prior art extracorporeal blood circuit that uses a venous reservoir.
Figure 2:
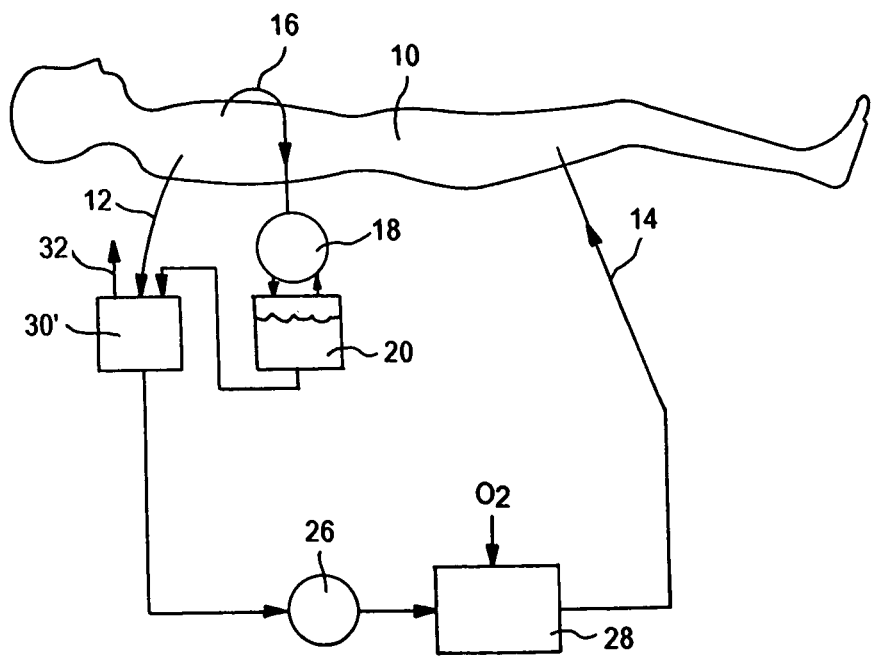
FIG. 2 is a schematic diagram of a second prior art extracorporeal blood circuit that does not use a venous reservoir.
Figure 3:
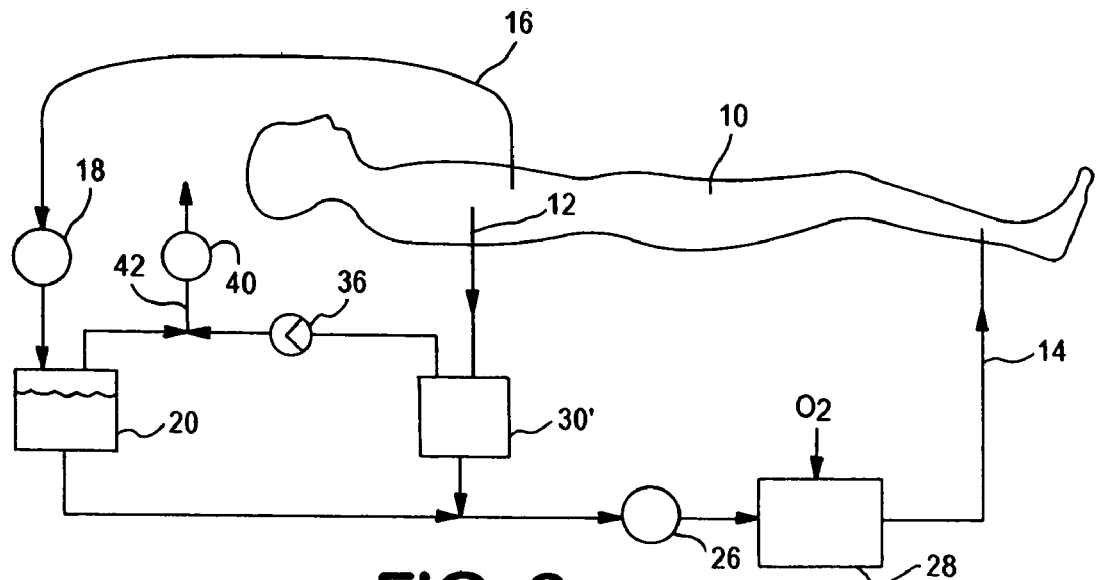
FIG. 3 is a schematic diagram of a third prior art extracorporeal blood circuit that does not use a venous reservoir and employs a venous blood filter with active air removal.
Figure 4:
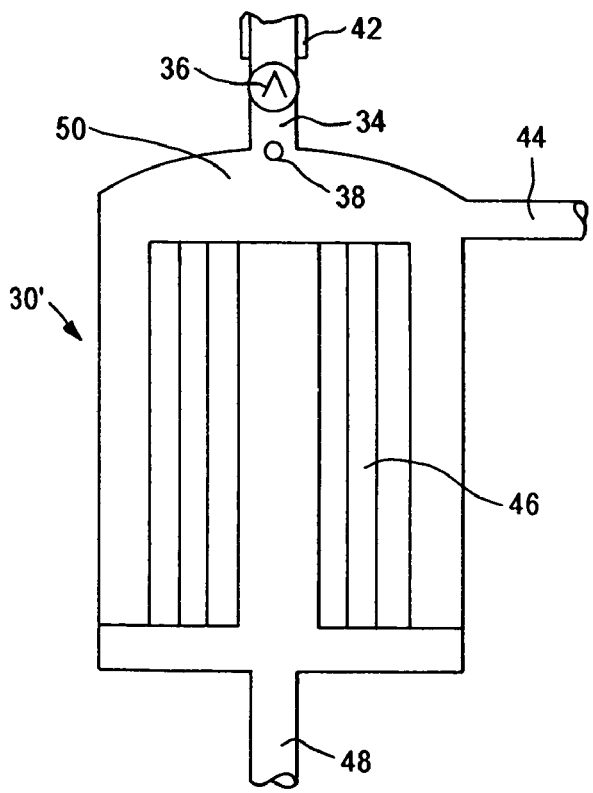
FIG. 4 is a simplified schematic view of the prior art venous blood filter of FIG. 3.

The various aspects of the present invention are preferably embodied in a method and system that incorporates a disposable, integrated extracorporeal blood circuit with reusable components including the reusable components of a heart-lung machine. The disposable, integrated extracorporeal blood circuit preferably comprises the set of principal components comprising a VARD, a centrifugal blood pump, an oxygenator, and an arterial blood filter all interconnected with fluid lines. The disposable centrifugal blood pump is coupled with the reusable blood pump driver that is in turn coupled to a pump driver console. An oxygen line is coupled to the disposable blood oxygenator via a flow meter and blender. Water lines are coupled to the disposable blood oxygenator via a module for controlling water flow and water temperature. The preferred embodiment of the VARD of the present invention comprises a venous filter that provides an AAR function under the control of a reusable AAR controller. The disposable, integrated extracorporeal blood circuit of the preferred embodiment of the present invention further comprises a disposable component organizing device or circuit support module for supporting the principal components and lines in a predetermined 3-D spatial relationship. The preferred embodiment of the present invention further comprises a reusable circuit holder adapted to be coupled to the reusable components of the heart lung machine to support the AAR controller and the reusable circuit support module.

The disposable, integrated extracorporeal blood circuit of the present invention preferably has access ports through which the operator or perfusionist may administer medications, fluids, and blood. In addition, the extracorporeal blood circuit preferably includes multiple sites for sampling blood and for monitoring various parameters, e.g., temperature, pressure, and blood gas saturation. Clamps and valves are also disposed in the lines extending between or from the principal components of the disposable, integrated extracorporeal blood circuit. The disposable, integrated extracorporeal blood circuit of the present invention can be set up and changed out more rapidly than conventional extracorporeal blood circuits, and arrangement of the supplied components minimizes the possibility of erroneous setup. The disposable, integrated extracorporeal blood circuit of the present invention is a closed system that reduces the air-blood interface and that minimizes the blood contacting surface area.

The disposable, integrated extracorporeal blood circuit of the present invention may be rapidly primed with prime solution. During priming, the venous return line connector is coupled to the arterial line connector. The extracorporeal blood circuit is supported in 3-D space so that the components and lines interconnecting the components are disposed between a circuit high elevation and a circuit low elevation. A prime solution source is supported at a source elevation higher than the circuit high elevation, and prime solution is delivered into the integrated extracorporeal blood circuit at the circuit low elevation. The flow of prime solution from the prime solution source into the extracorporeal blood circuit is controlled to upward fill the components and lines of the extracorporeal blood circuit with prime solution, thereby displacing air upward. Air is purged from the extracorporeal blood circuit as the prime solution fills the extracorporeal blood circuit.

The preferred embodiment of the best mode of practicing the invention disclosed herein incorporates all of the features of the present invention. However, it will be understood that the various aspects of the present invention can be practiced in alternative contexts than the context provided by the described preferred embodiment.

Disposable, Integrated Extracorporeal Blood Circuit

Figure 5:
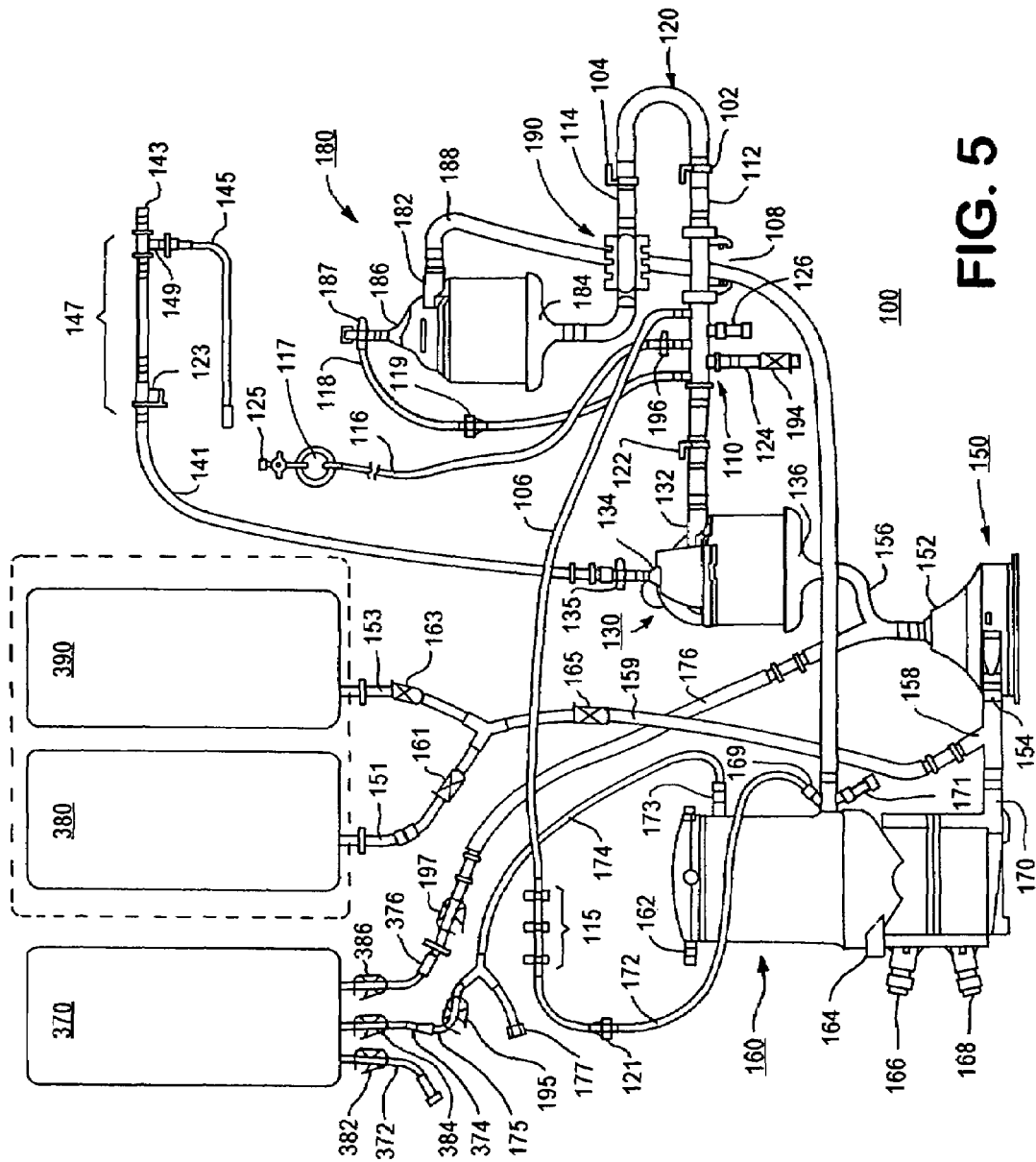
FIG. 5 is a schematic view of the components of the disposable, integrated extracorporeal blood circuit of the present invention in relation to prime solution holding bags and a sequestering bag.
Figure 6:
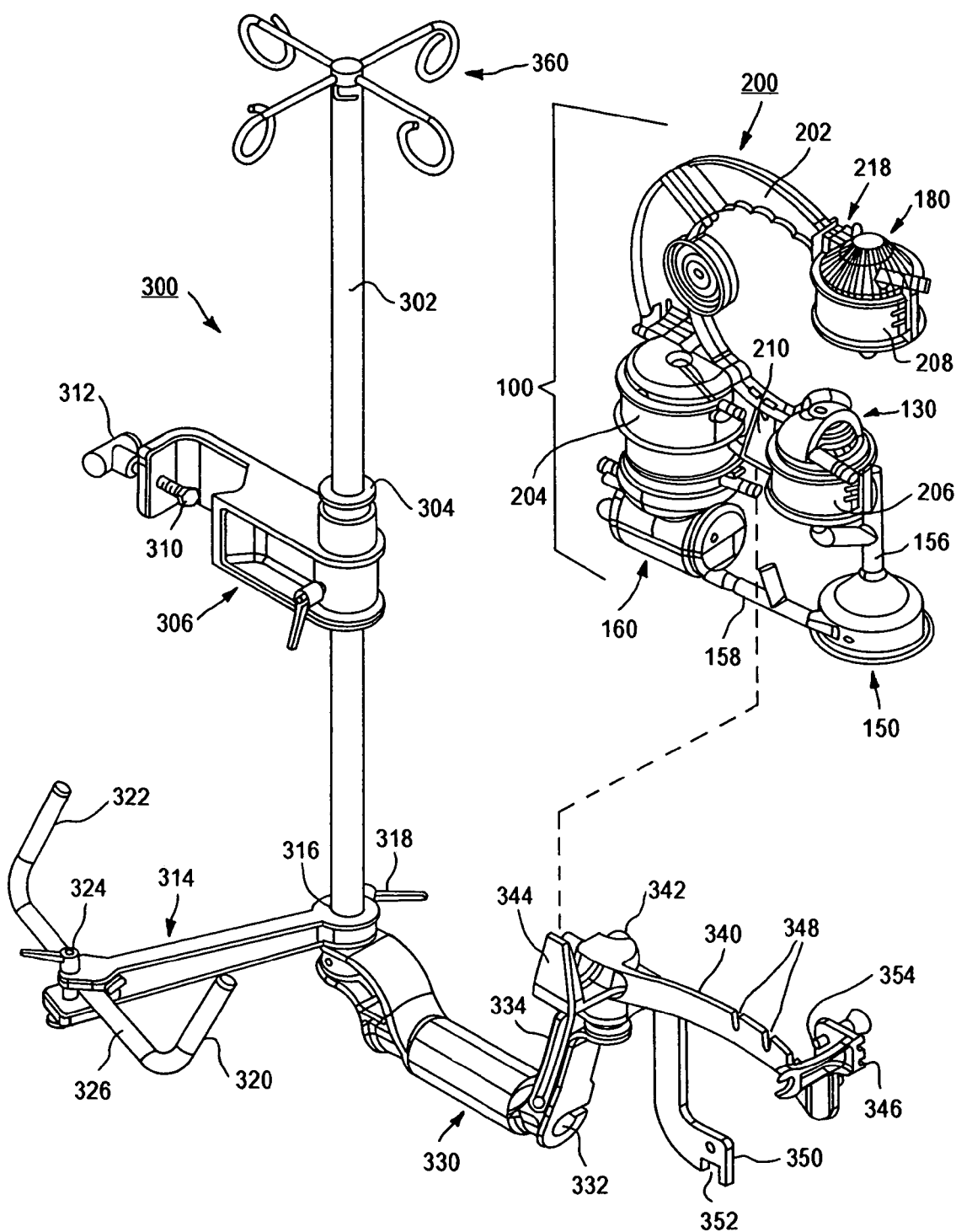
FIG. 6 is a representational diagram of the arrangement of the principle components of the disposable, integrated extracorporeal blood circuit of FIG. 5 supported in 3-D space by a disposable circuit support module that is mounted to a reusable circuit holder that supports further reusable components and is adapted to be mounted to the a heart lung machine console for operating the oxygenator and blood pump of the disposable, integrated extracorporeal blood circuit.

The components of the disposable, integrated extracorporeal blood circuit 100 are illustrated in FIGS. 5 and 6. The principal components of the disposable, integrated extracorporeal circuit 100 comprise the VARD 130, the centrifugal blood pump 150, the oxygenator 160, and the arterial blood filter 180. The disposable, integrated extracorporeal blood circuit 100 is illustrated in FIG. 5 in relation to prime solution holding bags 380 and 390 that drain prime solution into the disposable, integrated extracorporeal blood circuit 100 during priming and a sequestering bag 370 adapted to sequester excess prime solution or blood at times during the bypass procedure. The prime solution holding bags 380 and 390 are conventional IV bags that have penetrable seals that spikes can be inserted through in use. The sequestering bag 370 is supplied with three bag tubes 372, 374 and 376 that have respective Roberts clamps 382, 384 and 386 applied thereto to selectively clamp shut or open the bag tube lumens. For example, the Roberts clamps 382, 384, and 386 may be clamped shut when the sequestering bag 370 is attached to or detached from the disposable, integrated extracorporeal blood circuit 100. The interconnection of these principal components and the prime solution holding bags 380 and 390 and sequestering bag 370 through lines and further components is first described as follows.

Figure 9:
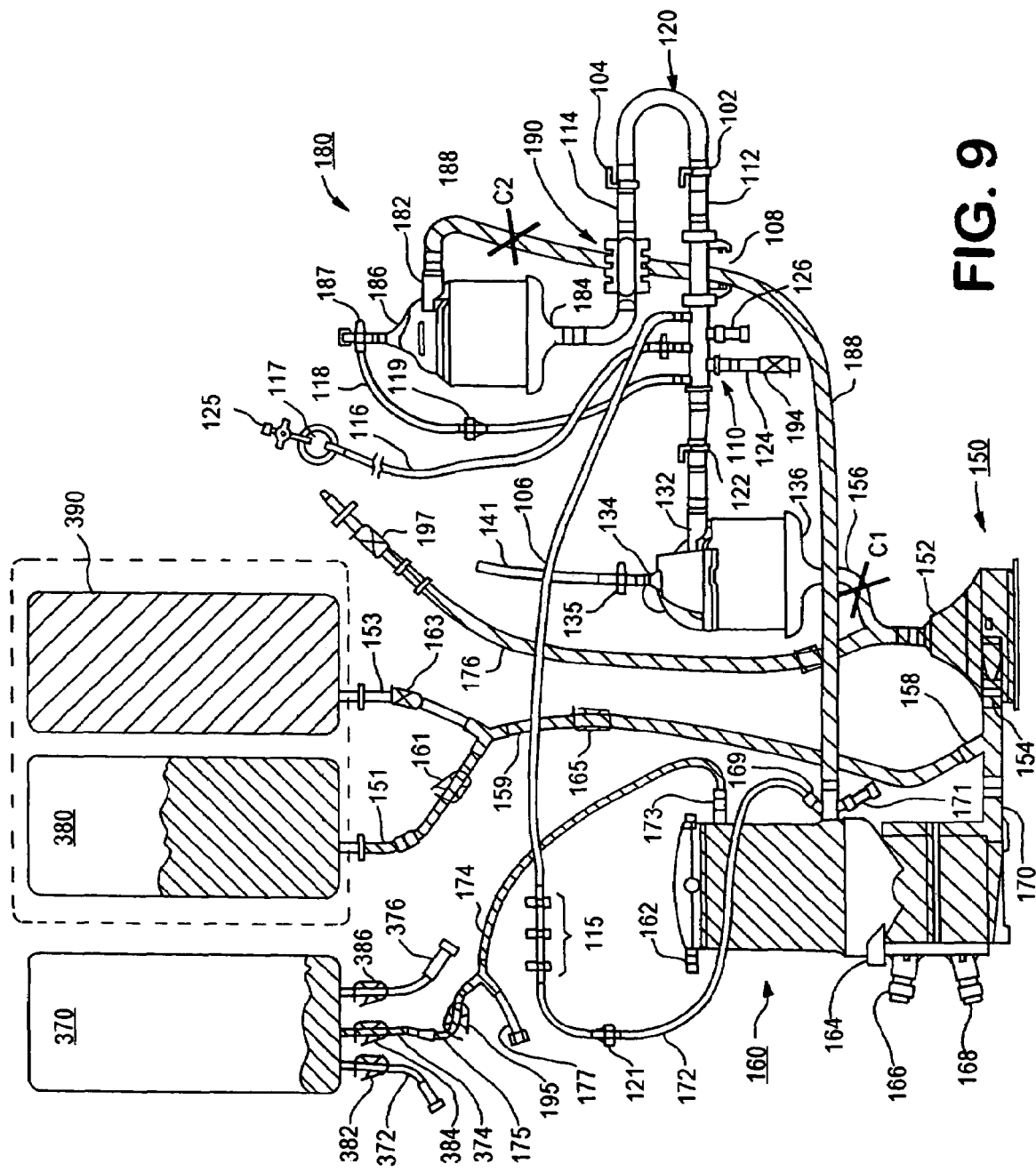
FIGS. 9-11 are schematic views of the components of the disposable, integrated extracorporeal blood circuit of the present invention in relation to a sequestering bag and first and second prime solution bags illustrating the steps of priming the disposable, integrated extracorporeal blood circuit with prime solution.
Figure 10:
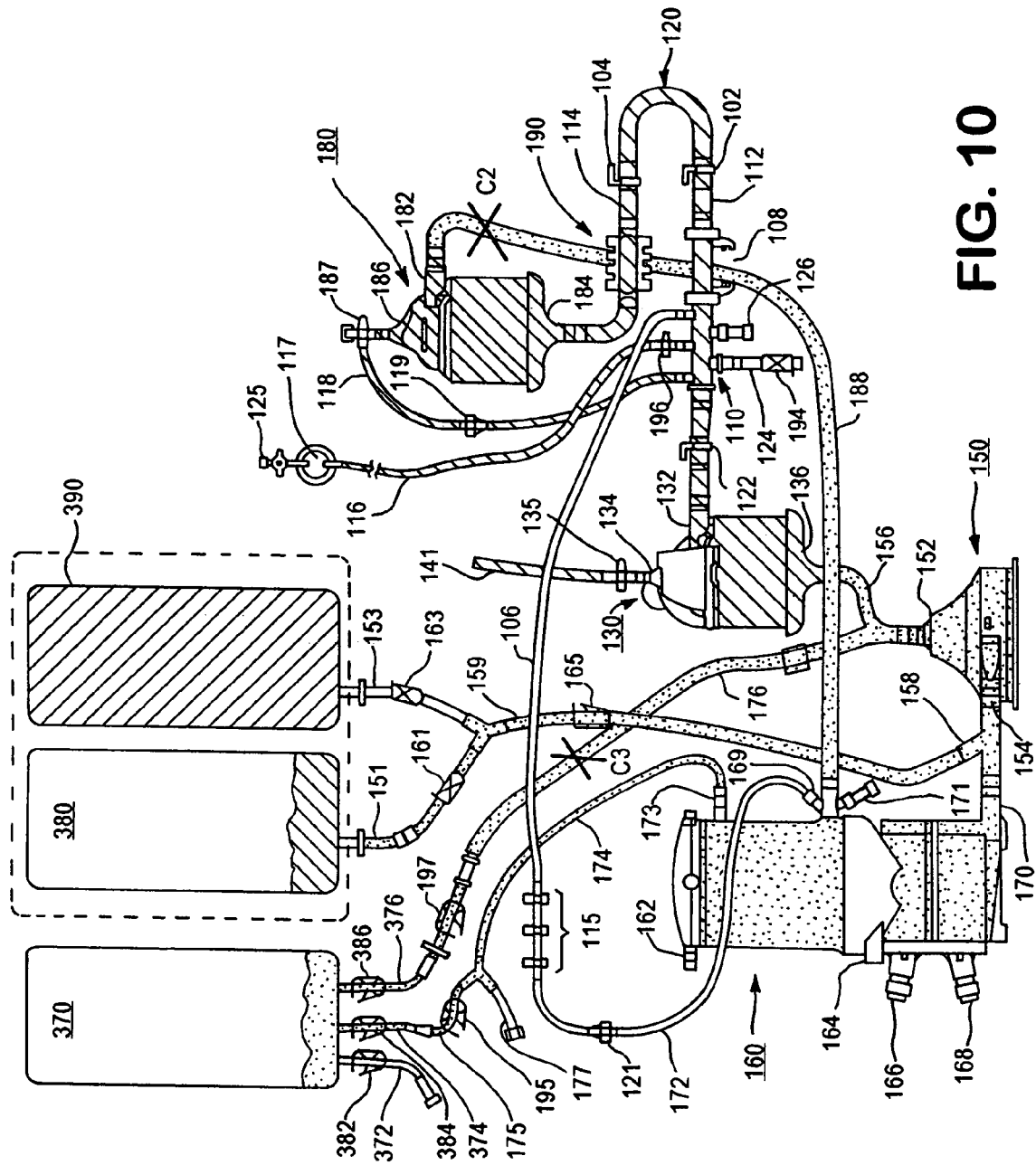
Figure 11:
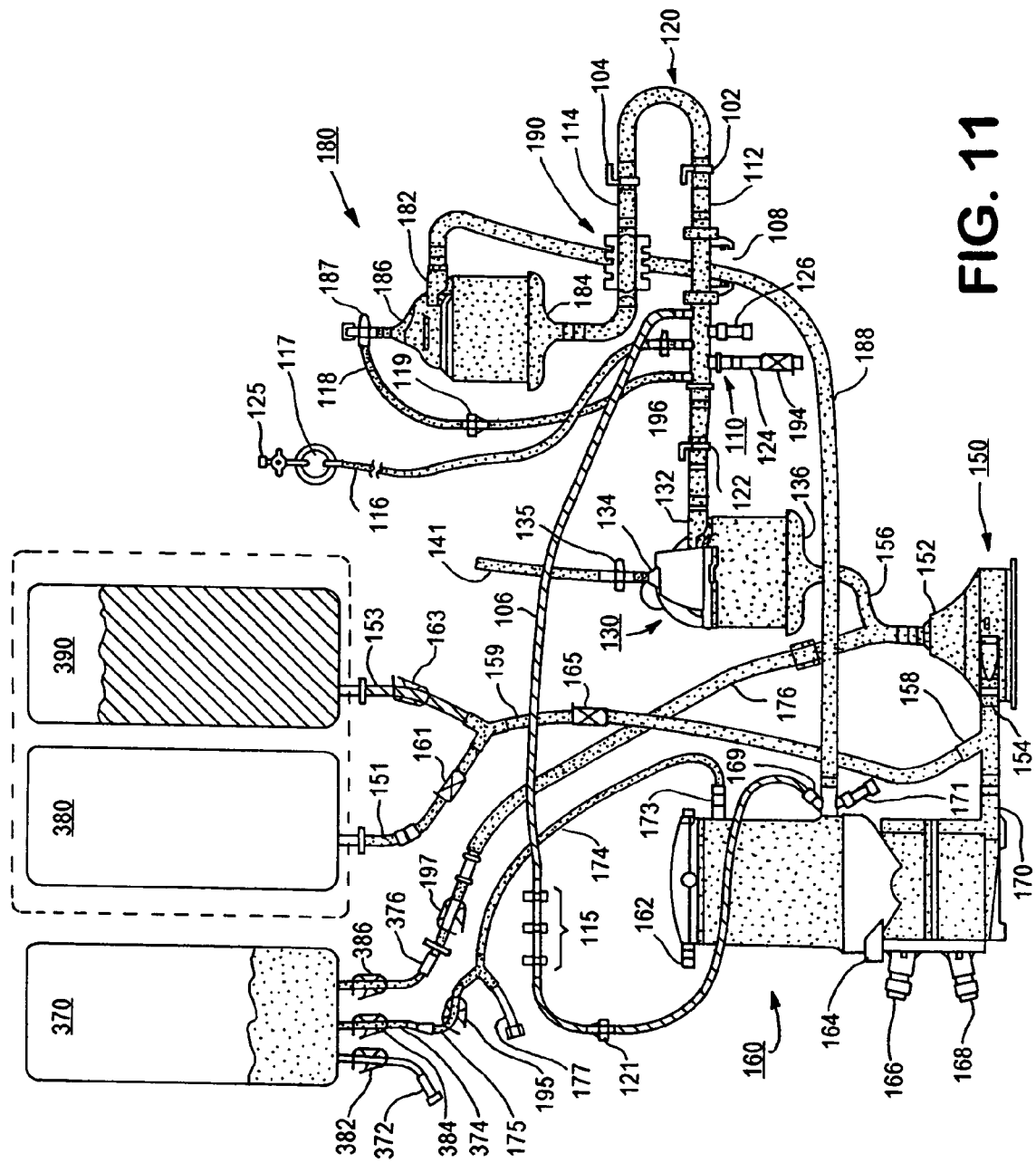

The disposable, integrated extracorporeal blood circuit 100 is also illustrated in FIG. 5 with a U-shaped, tubular, pre-bypass loop 120 that can be selectively used to connect the arterial blood line 114 with the venous return line 112 during flushing of the disposable, integrated extracorporeal blood circuit 100 with $CO_2$ gas and during priming of the disposable, integrated extracorporeal blood circuit 100 with prime solution from prime solution bags 380 and 390 as described further below with respect to FIGS. 9-11. The pre-bypass loop 120 is coupled to the venous return line 112 by a quick connect connector 102 and to the arterial line 114 by a quick connect connector 104. The arterial line 114 and venous return line 112 are preferably formed of 0.375 inch ID PVC tubing.

It will be understood that the pre-bypass loop 120 is disconnected from the venous and arterial blood lines 112 and 114, respectively, after the disposable, integrated extracorporeal blood circuit 100 is primed. Table lines extending to venous and arterial cannulae extending into the patient are then connected to the respective venous return line 112 and arterial line 114 through quick connectors 102 and 104, respectively. Any air that enters the venous return line 112 during this switching process is eliminated by the AAR system and method of the present invention as described further below.

The venous return line 112 extends from the quick connector 102 through a quick disconnect connector 122 to the inlet 132 of the VARD 130. The assembly of a tri-optic measurement cell (TMC) 38 BioTrend® connector 108 having a 0.375 inch ID lumen coupled to a utility connector 110 having a 0.375 inch ID lumen is interposed in the venous return line 112. The TMC 38 BioTrend® connector 108 may be used to hold a TMC cell (not shown) of the BioTrend™ Oxygen Saturation and Hematocrit System, sold by Medtronic, Inc., to measure blood oxygen saturation and blood hematocrit of venous blood passing through the venous return line 112. The utility connector 110 supports a plurality of standard luer ports and barbed ports.

A venous blood sampling line 106, preferably formed of 0.125 inch ID PVC tubing, extends between one port of the utility connector 110 to one side of a manifold 115. The manifold 115 comprises a rigid tube having a 0.125 inch ID tube lumen and three stopcocks with side vent ports arrayed along the tube and employed as described further below.

A venous blood pressure monitoring line 116 that is preferably formed of 0.125 inch ID PVC tubing is coupled to a stopcock 196 attached to a luer port of the utility connector 110 and extends to a pressure isolator 117 and stopcock 125. The pressure isolator 117 of the venous blood pressure monitoring line 116 has a flexible bladder and is sized to be attached to a Medtronic® Model 6600 pressure monitor and display box. Venous blood pressure monitoring may be used to optimize kinetic drainage. For example, venous blood pressure that is too high, too low, oscillating and/or chattering may indicate that the speed of the venous blood pump is incorrect and should be adjusted.

An arterial filter recirculation line 118, preferably formed of 0.125 inch ID PVC tubing and including a check valve 119, extends from a further luer port of the utility connector 110 to the arterial filter purge port 186 of the arterial filter 180. Under operating conditions described below, a small volume of arterial blood and any air bubbles are drawn through the arterial filter recirculation line 118 and check valve 119 from the arterial filter 180 into the venous return line 112. The check valve 119 prevents reverse flow of venous blood into the arterial filter 180.

In certain cases, it is desirable to provide passive venting of the venous blood in the venous return line 112, and so a short, 0.250 inch ID, tube stub 124, terminating in a 0.250 inch ID barbed port, extends from the utility connector 110 to function as a vent blood return port. A Roberts clamp 194 is fitted across the 0.250 inch ID tube stub 124 to be opened or closed in use when the tube stub is coupled to active or passive venting equipment, e.g., the Gentle Vent passive venting system sold by Medtronic, Inc.

A blood temperature monitoring adaptor 126 is provided extending from the utility connector 110 and enabling insertion of a temperature probe connected with temperature monitoring equipment.

The VARD 130 is described further below with reference to FIGS. 12A, 12B and 13. In general, air that is entrained in the venous blood drawn through the VARD inlet 132 tends to be separated from the venous blood within VARD 130 and accumulates in an upper chamber thereof. The presence of air is detected by signals output from air sensors located about the VARD 130, and the air is evacuated from the chamber.

The venous blood outlet 136 of VARD 130 is coupled to one branch of a "Y" style segment or blood pump inlet line 156, preferably formed of 0.375 inch ID PVC. The trunk of the "Y" style segment or line 156 is coupled to the blood pump inlet 152 of the centrifugal venous blood pump 150. The blood pump 150 is adapted to be positioned in use with a drive motor (not shown) as described further below that is selectively operated to draw venous blood through the VARD 130 and pump it into the oxygenator 160.

Preferably, venous blood pump 150 is a centrifugal blood pump, e.g., a Bio-Pump® centrifugal blood pump sold by Medtronic, Inc., that is capable of providing sufficient negative pressure (to −200 mm Hg) for kinetic assisted drainage of venous blood from the patient. Operation of the Bio-Pump® centrifugal blood pump is controlled by a Bio-Console® drive console sold by Medtronic, Inc. The Bio-Console® drive console provides electrical energy to drive a reusable pump drive that in turn drives the Bio-Pump® centrifugal blood pump. Exemplary blood pump drive systems are disclosed, for example, in U.S. Pat. Nos. 5,021,048 and 5,147,186.

A fluid infusion line 176, preferably formed of 0.375 inch ID PVC tubing, is coupled to the other branch of the "Y" style segment or line 156 and extends to a connection with the tube 376 of the sequestering bag 370 made through a tubing size adaptor and Roberts clamp 197. Prime solution can be selectively pumped or drained from the sequestering bag 370 during priming, and blood can be selectively pumped or drained from the sequestering bag 370 during the course of the bypass procedure.

The location of VARD 130 upstream of venous blood pump 150 in the depicted closed system provides kinetic assisted venous drainage due to the negative pressure exerted on venous blood by the venous blood pump 150. An AAR system and method automatically detects and suctions off air that collects in a high, quiescent point in the venous line of the disposable, integrated extracorporeal blood circuit 100. In the preferred embodiment of the present invention, the high point is within the upper part of VARD 130 adjacent to the purge port 134.

A VARD purge line 141, preferably formed of 0.250 inch ID PVC tubing, is coupled to the purge port 134 of VARD 130 through a stopcock 135 and extends to a purge line distal end connector 143 adapted to be coupled to a vacuum line. A VARD purge line segment 147 formed of silicone rubber and a vacuum sensor line 145 are coupled to an AAR controller as described further below. VARD purge line 141 or the purge port 134 of VARD 130 may include a means, e.g., a one-way check valve, to prevent air from being pulled into the VARD 130 prior to attachment of the purge line distal end connector 143 to the vacuum line. For example, a check valve 123 is located at the connection of the VARD purge line 141 with the VARD purge line segment 147. In addition, an air permeable, hydrophobic, fluid isolation filter 149, is located in a T-shaped branch of the purge line distal end connector 143 to prevent any blood suctioned from VARD 130 during operation of the AAR system from being suctioned into the vacuum sensor within the AAR controller that the vacuum sensor line 145 is connected to. The fluid isolation filter 149 is preformed with a female luer lock and a male luer lock for attachment between the T-connector of VARD purge line segment 147 and the vacuum sensor line 145, e.g., a 25 mm filter enclosing 0.2 µm Versapor® 200R hydrophobic acrylic copolymer on a non-woven support available from PALL Life Sciences Division, Ann Arbor, Mich., of Pall Corporation.

A purging vacuum produced by a pump or a vacuum outlet conventionally provided in operating rooms is applied through a vacuum line coupled to the purging line distal end connector 143. Although not shown in FIG. 5, a collection container or trap is to be interposed between purge line distal end connector 143 and the vacuum source or pump to trap the red blood cells that may be suctioned from VARD 130 through VARD purge line 141 for possible salvage and return to the patient. The liquid trap can be a standard hard-shell venous reservoir, a standard cardiotomy reservoir, a chest drainage container, or a blood collection reservoir used with the autoLog™ Autotransfusion System sold by Medtronic, Inc. The blood collection reservoir used with the autoLog™ Autotransfusion System has a 40 micron filter and may be mounted onto a mast of the console of the heart-lung machine or other equipment in the operating room to function as a liquid trap. Preferably, the vacuum source or pump is capable of supplying a minimum of about −215 mmHg vacuum, and preferably is capable of suctioning about 400 ml/min of air from the liquid trap without the vacuum decreasing below about −180 mmHg.

The blood pump outlet 154 is coupled to one end of a "T" style connector functioning as an oxygenator inlet line 158, preferably formed of 0.375 inch ID PVC tubing. The other end of the "T" style line 158 is coupled to the oxygenator blood inlet 170 of oxygenator 160. The oxygenator blood inlet 170 and the venous blood outlet 154 are thereby coupled together and supported at substantially the same venous blood outlet/inlet elevation by the "T" style line 158.

One end of a priming line 159, preferably formed of 0.250 inch ID PVC tubing, is coupled to a side branch of the "T" style connector or line 158. The priming line 159 extends to branching segments or lines 151 and 153, preferably formed of 0.250 inch ID PVC tubing, that terminate in spikes that are inserted into the penetrable openings or seals of the prime solution bags 380 and 390. Roberts clamps 161, 163, and 165 are fitted over the respective tubing segments or lines 151, 153 and 159 to selectively clamp shut or open the tube lumens during gravity priming of the disposable, integrated extracorporeal blood circuit 100 as described further below. The side branch of the "T" style line 158 preferably extends away from the blood pump 150 at an angle less than 90° to the trunk of the "T" style line 158 so that any air that is entrained in the prime solution does not stick at the junction of the side branch and instead rises through the side branch and the priming line 159 to accumulate in a prime solution bag 380 or 390. Due to this arrangement, no air bubbles are entrapped in the line 159 during priming or operation of the disposable, integrated extracorporeal blood circuit 100.

A blend of oxygen and air enters the oxygenator 160 through gas inlet 162 and exits the oxygenator 160 through access port 164. Gas exchange between the oxygen and the venous blood entering oxygenator blood inlet 170 then takes place by diffusion through the pores in the hollow fibers of the oxygenator 160. Thermal energy may be added or removed through the blood heat exchanger that is integral with the oxygenator 160. Water is heated or cooled by a heater/cooler of the heart-lung machine and warmed or chilled water is delivered to the water-side of the heat exchanger. Water enters the heat exchanger through a hose (not shown) coupled to water inlet port 166 and exits the heat exchanger through water outlet port 168 and a hose (not shown) coupled thereto. The oxygenator 160 is preferably a blood oxygenator of the type disclosed U.S. Pat. Nos. 4,975,247, 5,312,589, 5,346,621, 5,376,334, 5,395,468, 5,462,619, and 6,117,390, for example. Preferably, oxygenator 160 comprises an AFFINITY® hollow fiber membrane oxygenator sold by Medtronic, Inc.

The temperature modulated, oxygenated blood is pumped out of the oxygenator blood outlet 169 and through an oxygenator outlet line 188, preferably formed of 0.375 inch ID PVC tubing, that is coupled to the arterial filter inlet 182 of the arterial filter 180. The heated or cooled oxygenated blood can also be pumped out of a branch of the oxygenator outlet 169 and through an arterial blood sampling line 172, preferably formed of 0.125 inch ID PVC tubing and including a check valve 121, that extends to one input of manifold 115 for sampling of arterial blood and for drug administration.

A temperature monitoring adaptor 171 similar to adaptor 126 branches from of the oxygenator blood outlet 169 to be used to monitor oxygenated blood temperature.

A recirculation/cardioplegia line 174, preferably formed of 0.250 inch ID PVC tubing, extends from a recirculation port 173 of the oxygenator 160 to a "Y" style connector having two branches 175 and 177. The branch 175 is coupled to the luer port of line 58 of the sequestering bag 370. A Roberts clamp 195 is used to open or close the branch 175 of the "Y" style connector coupled to line 58 so that prime solution or oxygenated blood can be selectively pumped into the sequestering bag 370 during the course of priming or performance of the bypass procedure. A second branch 177 of the recirculation/cardioplegia line 174 comprises a tube that is provided with a closed end and can be left intact or cut away so that the recirculation/cardioplegia line 174 can be selectively coupled to a cardiaplegia source or a hemoconcentrator while the Roberts clamp 195 is closed.

The delivery of cardioplegia solution reduces or discontinues the beating of the heart in a manner that will minimize damage to the myocardium. Cardioplegia solution can also supply other ingredients to provide for myocardium protection and may be delivered alone or may include oxygenated blood diverted from the arterial line. A cardioplegia circuit is formed that comprises the oxygenated blood line, a cardioplegia solution bag and line, a cardioplegia delivery line, a pump (e.g., peristaltic), and may also comprise pressure transducers to monitor the solution pressure, an air detector and filters to prevent bubbles from entering the heart, a timer, temperature sensors and a heat exchanger to monitor and control fluid temperature, and a device for controlling and recording the total volume of cardioplegia solution that is pumped. The cardioplegia solution is delivered to the coronary arterial network or coronary sinus for distribution throughout the myocardium and the circulatory system in a manner well known in the art.

The arterial blood filter 180 may take the form disclosed in U.S. Pat. Nos. 5,651,765 and 5,782,791, for example, and preferably comprises an AFFINITY® Arterial Filter sold by Medtronic, Inc. The oxygenated blood is pumped under the pressure exerted by the venous blood pump 150 through the arterial filter inlet 182, through a filter and screen disposed within the arterial blood filter 180, and through the arterial filter outlet 184 into the arterial line 114. Microemboli are filtered from the oxygenated blood as it passes through the arterial filter 180. Air that is entrained in the oxygenated blood tends to be separated from the oxygenated venous blood by the screen and accumulates in an upper chamber the arterial filter 180 below arterial filter purge port 186.

The arterial filter purge port 186 is coupled to a three-way stopcock 187 in the arterial filter purge port 186 that has a branch coupled to an end of arterial filter recirculation line 118. The three-way stopcock 187 is normally in an air evacuation position that connects the arterial filter recirculation line 118 with the arterial filter purge port 186. A low volume of arterial blood and any air that collects in the upper chamber the arterial filter 180 below arterial filter purge port 186 are drawn by blood pump 150 through the utility connector 110 and venous return line 112 into the VARD 130. The difference in pressure between the positive pressure of the oxygenated blood within the chamber of the arterial filter 180 and the negative pressure in the venous return line 112 draws the blood and air from the chamber of the arterial filter 180 when the venous blood pump 150 is running and the three-way stopcock 187 is moved to the air evacuation position. The check valve 119 in the arterial filter recirculation line 118 prevents reverse flow of venous blood through the recirculation line 118 when the blood pump 150 is not pumping. The three-way stopcock 187 can be manually moved to a priming position opening the arterial filter chamber to atmosphere to facilitate priming of the disposable, integrated extracorporeal blood circuit 100. As described below, the arterial filter 180 is fitted into a receptacle of a disposable circuit support module such that the operator can manually lift and invert the arterial filter 180 during priming or during the bypass procedure to facilitate evacuation of any air observed in the arterial filter 180.

The filtered, oxygenated blood is returned to the patient as arterial blood through the arterial line 114 coupled to the arterial filter outlet 184 and through a table line fitted to the quick connector 104 and coupled to an arterial canulla (not shown) or directly to an end of an elongated arterial cannula extending into the patient's heart. The arterial line 114 passes through a blood flow transducer connector 190 that receives and supports a Bio-Probe® blood flow transducer sold by Medtronic, Inc. to make arterial flow rate measurements. In normal operation, the Bio-Console® drive console determines arterial blood flow rate from the output signal of the Bio-Probe® flow probe transducer mounted to blood flow transducer connector 190 to make flow rate measurements of blood flow in arterial line 114 or in oxygenator outlet line 188. Oxygenated, arterial blood flow rate is generally determined to an accuracy of +/−5%.

The above-described barbed connections and luer connections with lines or tubing preferably do not leak at pressures ranging between +750 mmHg and −300 mmHg. In addition, the barbed connections preferably withstand pull forces up to 10 lbs linear pull.

All surfaces of the disposable, integrated extracorporeal blood circuit exposed to blood should be blood compatible through the use of biocompatible materials e.g., silicone rubber, PVC, polycarbonate or plastisol materials. Preferably, the blood contacting surfaces of the disposable, integrated extracorporeal blood circuit are coated with Carmeda® BioActive Surface (CBAS™) heparin coating under license from Carmeda AB and described in U.S. Pat. No. 6,559,132, for example.

The disposable, integrated extracorporeal blood circuit 100 of the present invention preferably has operable flow rates of 1-6 liters per minute of blood through it without producing gas bubbles within venous blood pump 150 or through fibers of oxygenator 160. The disposable, integrated extracorporeal blood circuit is spatially arranged and supported in 3-D space by a component organizing and supporting system of the present invention at the height of the patient so that the respective venous return and arterial lines 112 and 114 can be made as shortened to reduce prime volume.

Figure 7:
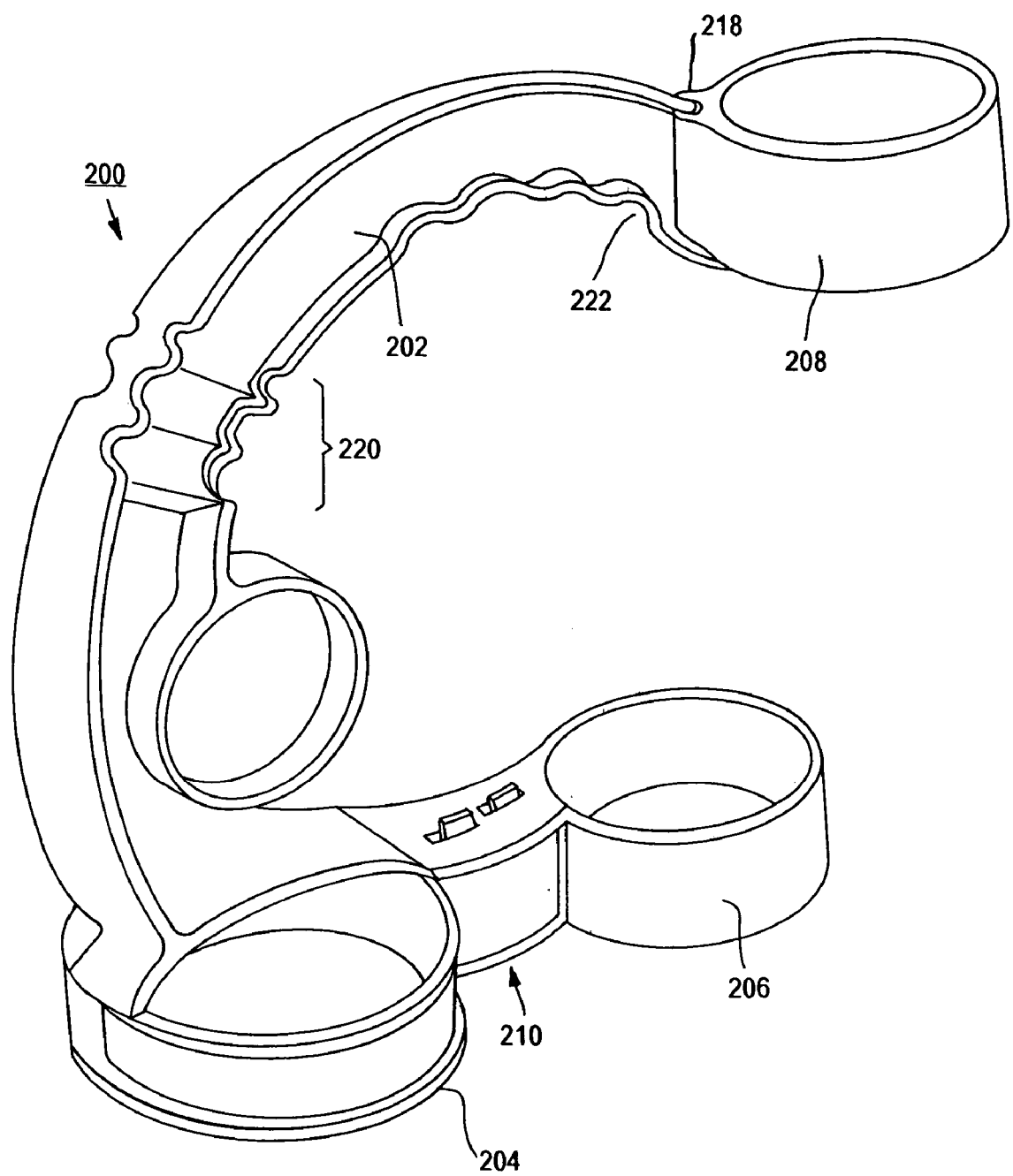
FIG. 7 is a perspective view of the disposable circuit support module of FIG. 6.
Figure 8:
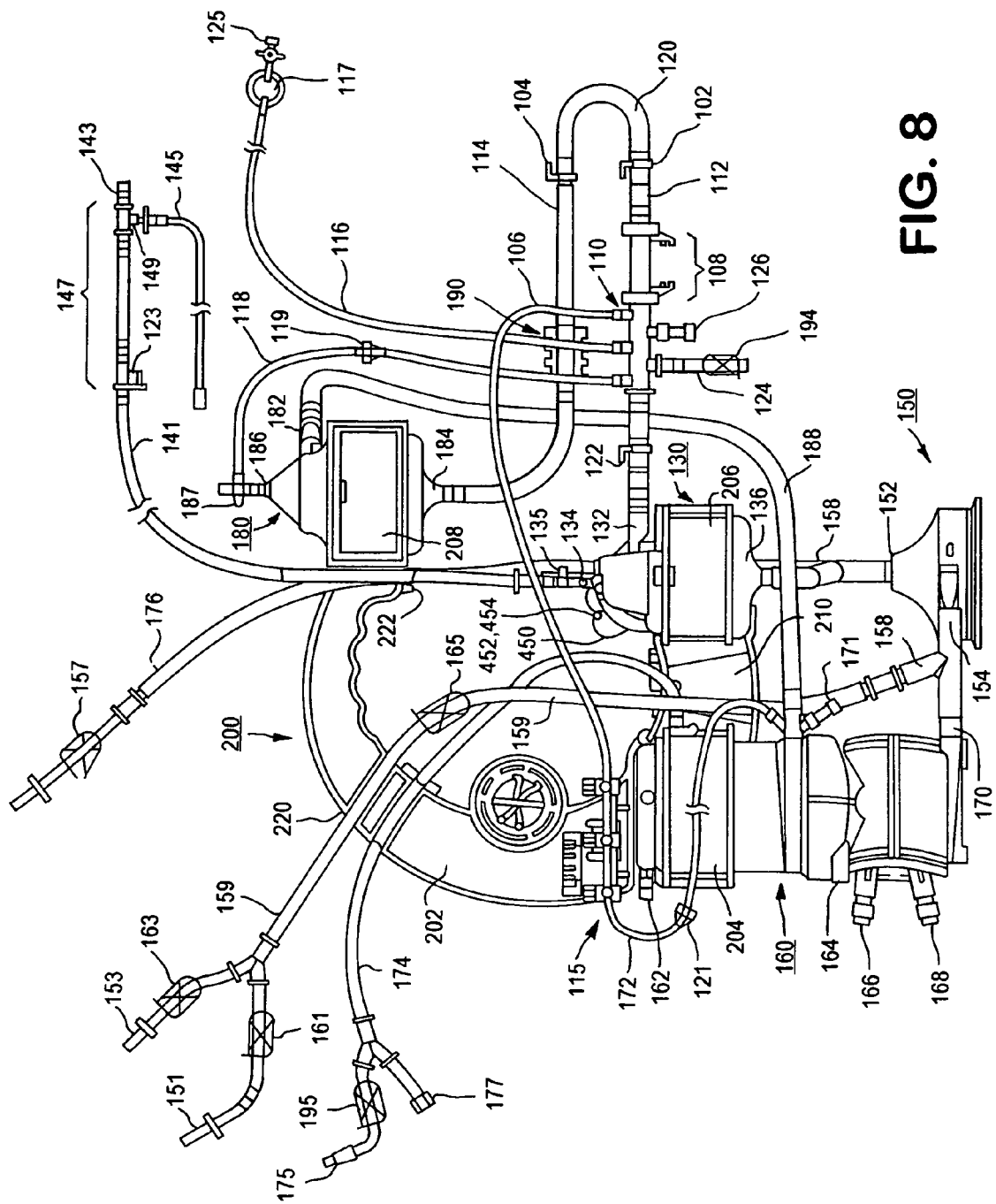
FIG. 8 is a schematic view of the components of the disposable, integrated extracorporeal blood circuit of the present invention supported by the disposable circuit support module of FIGS. 6 and 7.

The above-described components of the disposable, integrated extracorporeal blood circuit 100 are spatially arranged and supported in 3-D space as shown in FIG. 5 by a disposable circuit support module 200 and a reusable circuit holder 300 as shown in FIGS. 6-8. Most of the above-described lines and other components interconnecting or extending from the VARD 130, the centrifugal blood pump 150, the oxygenator 160, and the arterial blood filter 180 are not shown in FIG. 6 to simplify the illustration.

The disposable circuit support module 200 is formed of a rigid plastic material having a C-shaped arm 202 extending between lower snap fittings 204 and 206 and an upper snap fitting 208. A receptacle 210 is adapted to fit onto the receiver 344 of the circuit holder 300. As shown in FIG. 6, the VARD 130 and the oxygenator 160 are directly supported by the C-shaped arm 202, and the "Y" style line 156 and "T" style line 158 couple the centrifugal blood pump 150 between the venous blood outlet 136 and the venous blood inlet 170, whereby the blood pump 150 is indirectly supported by the C-shaped arm 202. The "Y" style line 156 and "T" style line 158 are flexible, which advantageously allows the perfusionist to grasp the blood pump 150 while it is not being driven during priming and tilt it to see if any air is accumulating in the blood pump chamber. Any air accumulating in the blood pump chamber during priming, as described further below, can be dislodged in this way.

The snap fittings 204 and 206 each comprise a fixed, concave, band formed as part of C-shaped arm 202 and a separate U-shaped, band. The snap fitting 208 comprises a concave band that can be attached to or detached from the C-shaped arm 202 and a separate U-shaped band. The separate U-shaped bands can be snapped into engagement with the concave bands to form a generally cylindrical retainer band dimensioned to engage the sidewalls of the oxygenator 160, the VARD 130 and the arterial blood filter 180.

During assembly, the oxygenator 160 is applied against the fixed, concave, half-band, and the U-shaped, half-band is snapped around the oxygenator 160 and to slots on either side of the fixed, concave, half-band to entrap oxygenator 160 in lower oxygenator snap fitting 204 during assembly of the extracorporeal blood circuit 100 so that it is difficult to remove the oxygenator 160. Similarly, the VARD 130 and the arterial blood filter 180 are supported and entrapped in lower and upper VARD and arterial filter snap fittings 206 and 208, respectively.

The upper snap fitting 208 encircling arterial blood filter 180 is detachable at a clip 218 from the C-shaped arm 202. The arterial blood filter 180 and upper snap fitting 208 can be manually detached at clip 218 and inverted by the perfusionist during priming. Any air bubbles trapped in the lower portion of the arterial blood filter 180 adjacent the arterial filter outlet 184 can then rise up through the inverted arterial filter outlet 184 into the arterial line 114 to be drawn through the bypass circuit 120 and the venous return line 112 into the VARD 130 to be purged therefrom. The perfusionist can observe the movement of the air bubbles and then insert the arterial filter 180 back into clip 218.

As shown in FIG. 8, lateral raceways 220 and vertical raceways 222 are provided in the C-shaped arm 202 that laterally and vertically extending lines can be fitted into. The VARD purge line 141 and the fluid infusion line 176 are extended vertically from the VARD 130 and the branch of the "Y" style line 156, respectively, through one vertical raceway 222. The priming line 159 and the recirculation/cardioplegia line 174 are extended laterally through the lateral raceways 220.

Disposable circuit support module 200 advantageously maintains proper orientation and positioning of the supported principal components and the lines extending between or from them to optimize function. The short lines minimize surface area contacted by blood. The oxygenator 160 is supported by disposable circuit support module 200 so that the blood pump outlet 154 and the oxygenator blood inlet 170 connected by "T" style connector or line 158 are at about the same circuit low elevation level below prime solution holding bags 380 and 390 in order to facilitate gravity priming through priming line 159 and upward filling of the blood pump 150 and oxygenator 160 and other circuit components and lines with prime solution. Disposable circuit support module 200 positions the VARD 130 above the blood pump 150 and the arterial blood filter 180 above the VARD 130 in order to facilitate upward priming and movement of air into the arterial filter purge port 186 to be drawn into the VARD 130 and purged as described further below.

Module 200 is advantageously configured to allow access for clamping or unclamping the lines or tubing segments or for making connections to the various ports. The disposable circuit support module 200 advantageously allows venous blood pump 150 to be independently manipulated, e.g., rotated, swiveled, and/or pivoted, with respect to the disposable circuit support module 200 and holder 300. Disposable circuit support module 200 maintains proper positioning/alignment of the components and lines of the disposable, integrated extracorporeal blood circuit 100 to optimize priming of the disposable, integrated extracorporeal blood circuit 100 in a very short time. Preferably, disposable circuit support module 200 is transparent to allow sight confirmation of prime solution or blood in the lines and other transparent components.

Moreover, the disposable, integrated extracorporeal system 100 mounted to the disposable circuit support module 200 can be assembled as a unit and then attached to the circuit holder 300 for priming and use during a bypass procedure. A replacement assembly of a disposable, integrated extracorporeal system 100 and a disposable circuit support module 200 as shown in FIG. 8 can be quickly assembled and substituted in a change-out during priming or the bypass procedure if it is necessary to do so.

The circuit holder 300 comprises a mast 302 that extends through a shaft collar 304 of a mast arm assembly 306. The shaft collar 304 can be moved along the mast 302, and mast arm assembly 306 can be fixed at a selected position by tightening a lever 308. The mast arm assembly 306 includes a U-shaped notch 310 that can be inserted around an upright mast (not shown) of a heart-lung machine console (not shown), and a clamp 312 can be rotated and tightened to hold the mast 302 in a vertical orientation close to the heart-lung machine console. The mast 302 is provided with an IV hanger 360 that the prime solution holding bags 380 and 390 and the sequestering bag 370 can be hung from.

The mast 302 extends downward from the mast arm assembly 306 and through a collar 316 of an electronics arm assembly 314 that can be moved along the mast 302 and fixed in place by tightening a lever 318. The electronics arm assembly 314 extends to a cross-bar 326 supporting a right support arm 320 adapted to support an AAR controller and a left support arm 322 adapted to support a pressure monitor and display box, e.g., the Medtronic® Model 6600 pressure monitor and display box sold by Medtronic, Inc. The angle of the cross-bar 326 with respect to the electronics arm assembly 314 and the support angle of the right and left support arms 320 and 322 with respect to the cross-bar 326 can be adjusted by loosening the lever 324, rotating the cross-bar 326 and pivoting the right and left support arms 320 and 322 to the desired angles, and tightening the lever 324.

The lower end of the mast 302 is coupled to a laterally extending support arm assembly 330 that is formed with a cable supporting and routing channel 332. A laterally extending module arm assembly 340 and a downwardly extending external drive arm assembly 350 are mounted to an upward extension 334 of the support arm assembly 330 by a spring lock mechanism 342. A tapered male receiver 344 extends upward to be received in the downwardly extending female receptacle 210 of the circuit support module 200 when the disposable, integrated extracorporeal blood circuit 100 is mounted to the circuit holder 300. Line receiving slots 348 are provided in the laterally extending module arm assembly 340 for supporting cables for temperature monitoring and the VARD cable 450. VARD cable 450 has a cable connector 452 that is attached to a VARD sensor connector 454 as schematically illustrated in FIG. 12B.

A TMC clip 346 is fitted to the free end of the laterally extending module arm assembly 340 for engaging the TMC 38 BioTrend® connector 108 into which the TMC cell of the BioTrend™ Oxygen Saturation and Hematocrit System is inserted to measure venous blood oxygen saturation and venous blood hematocrit of venous blood flowing through the venous return line 112 of the disposable, integrated extracorporeal blood circuit 100. A cable (not shown) from the TMC cell supported by TMC clip 346 extends to a BioTrend™ Oxygen Saturation and Hematocrit System.

The Bio-Probe® blood flow transducer sold by Medtronic, Inc. to make blood flow rate measurements through the arterial line is adapted to be mounted to the laterally extending module arm assembly 340 at pin 354. A cable (not shown) extends from the Bio-Probe® blood flow transducer supported at pin 354 extends to a Bio-Probe® blood flow monitor sold by Medtronic, Inc.

An external drive motor for the blood pump 150 is attached to the free end mount 352 of the external drive arm assembly 350 to mechanically support and drive the blood pump 150 through magnetic coupling of a motor driven magnet in the external drive motor with a magnet of the centrifugal blood pump 150. An adaptor can be attached to the free end mount for coupling a hand-cranked magnet with the magnet of the centrifugal blood pump 150 in an emergency situation.

Thus, the VARD 130, the centrifugal blood pump 150, the oxygenator 160, and the arterial blood filter 180 principal components, as well as the lines and other associated components identified in FIG. 5, are spatially arranged and supported in 3-D space by the disposable circuit support module 200 and the reusable circuit holder 300 as shown in FIGS. 6-8. The assembly is closely positioned to the heart-lung machine console that operates the drive motor of the centrifugal blood pump 150, supplies oxygen to the oxygenator 130, and controls the temperature of the blood or cardioplegia solution traversing the oxygenator 130. The position of the mast arm assembly 306 along the mast 302 can be adjusted to optimally extend the module arm assembly 340 toward and over the patient during the procedure. The position of the electronics arm assembly 314 along the mast 302 can be adjusted and fixed in place by tightening a lever 318 to optimally position the AAR controller and Medtronic® Model 6600 pressure monitor and display box for use during the bypass procedure. The fixed distance between the support arm assembly 330 and the IV hanger 360 ensures that the lengths of the priming line 159 and the fluid infusion line 176 coupled with the prime solution holding bags 380 and 390 and the sequestering bag 370, respectively, are advantageously minimized and are not affected by the positioning of the mast arm assembly 306 along the mast 302.

Connections of the sensors, lines, ports, etc., with further components can be readily effected after the disposable, integrated extracorporeal blood circuit 100 is assembled with the disposable circuit support module 200 and mounted to the reusable circuit holder 300. For example, the reusable VARD sensor cable 450 depicted in FIG. 8 extends from the VARD connector 454 laterally through channel 332 to make a connection with an AAR controller in a manner described further herein.

In accordance with a further aspect of the present invention, flushing, priming, and use of the disposable, integrated extracorporeal blood circuit is simplified and made more reliable and efficient.

The disposable, integrated extracorporeal circuit 100 is flushed with the pre-bypass loop 120 in place with $CO_2$ gas after set-up and prior to priming in order to drive out any ambient air. Referring to FIG. 8, the fluid infusion line 176 is clamped by closing Roberts clamp 197. In reference to FIG. 14, a portion of the VARD purge line segment 147 is fitted into a fluid in-line (FIL) sensor 404, and the purge line distal end connector 143 is fitted into a clip 426 to orient the fluid isolation filter 149 vertically. The VARD purge line segment 147 is not fitted into the purge valve 410 (preferably a pinch valve as described further below) at this time so that $CO_2$ gas can flow through the VARD 130 and the VARD purge line 141 and purge line segment 147 to atmosphere. The VARD stopcock 135 is set to the open position so that $CO_2$ gas can flow through the VARD 130 to atmosphere. The arterial filter purge port 186 is opened to atmosphere by setting stopcock 187 to the appropriate position so that $CO_2$ gas can flow through the arterial filter 180 to atmosphere.

A $CO_2$ gas delivery line with a microporous bacteria filter is attached to the 0.250 inch spike at the end of one of priming line branch 151 or 153, and the associated Roberts clamp 161 or 163 and the Roberts clamp 165 are opened. The Roberts clamps 195 and 197 are also opened. The $CO_2$ gas is then turned on to flow through 0.250 inch PVC tubing priming line 159 and then through all of the major components and lines of the disposable, integrated extracorporeal circuit 100 to atmosphere at a flow rate of 2-3 liters per minute. Upon completion, the $CO_2$ gas is turned off, and the VARD stopcock 135 is closed. The 0.250 inch priming line 151 or 153 is disconnected from the $CO_2$ line, and the associated Roberts clamp 161 or 163 is clamped again.

Priming

The prime volume of the disposable, integrated extracorporeal blood circuit 100 preferably is roughly about 1000 ml or less. Preferably, the disposable, integrated extracorporeal blood circuit may be primed using a single one-liter intravenous bag 380 of prime solution, e.g., a saline solution. However, two prime solution bags 380 and 390 are preferably provided and filled with prime solution for use in initial priming or as required during the bypass procedure.

The steps of priming the disposable, integrated extracorporeal circuit 100 with the bypass circuit 120 fitted in place are shown in FIGS. 9-11. The blood pump 150 is turned off during initial stages of priming and turned on at the end stage of priming. The VARD purge line 141 (shown in part) is extended upward so that purge line distal end connector 143 is located about at the elevation of hanger 360 so that air accumulating in can VARD 130 can escape through the open purge line distal end connector 143. The arterial line 114 is at a slightly higher elevation than the venous return line 112 due to the U-shape of the bypass circuit 120. As prime solution is fed by gravity through the priming line 159, the prime solution enters the circuit low elevation at "T" style connector or line 158 and upward fills the components and lines of the extracorporeal blood circuit 100 in a sequence illustrated in FIGS. 9-11. Oxygenator 160 and the oxygenator outlet line 188 are antegrade filled, i.e., upward filled with the normal direction of blood flow when blood pump 150 is operating. Blood pump 150, VARD 130, venous return line 112, utility connector 110, bypass circuit 120, and arterial line 114 are retrograde filled, that is upward filled against the normal direction of blood flow when blood pump 150 is operating.

The prime solution bags 380 and 390, filled with prime solution, and the empty sequestering bag 370 are hung on the IV hangar 360 in preparation for priming. The Roberts clamps 382 and 386 can be left open as shown in FIG. 9 because the spike ports 372 and 376 are not yet perforated. The branch 177 of the "Y" style connector attached to the recirculation/cardioplegia line 174 employed during cardioplegia remains plugged, and the temperature sensor ports 171 and 126 are sealed. Initially, Roberts clamps 384, 161, 163, 165, 194 and 195 are closed, and the Roberts clamp 197 remains open.

As shown in FIG. 9, the 0.250 inch spikes of the lines 151 and 153 branching from the 0.250 inch priming line 159 are inserted through the penetrable seals of the prime solution bags 380 and 390, respectively. A branch 175 of the "Y" style connector attached to the recirculation/cardioplegia line 174 is coupled to the bayonet access port at the free end of the bag line 374 of the sequestering bag 370. The remaining ports and stopcocks remain as set at the end of the flushing operation. Tubing clamps, e.g., hemostats, are applied at about point C1 of the branch of the "Y" style line 156 that is coupled at its trunk to the blood pump inlet 152 and at about point C2 in the oxygenator outlet line 188 to prevent flow of prime solution into the chambers of VARD 130 and arterial blood filter 180, respectively.

Then, the Roberts clamps 161 and 165 are opened to gravity fill the pump 150, the oxygenator 160, the fluid infusion line 176, and the oxygenator outlet line 188 with prime solution draining from prime solution bag 380 while the clamp is maintained at C1. The Roberts clamp 197 is opened (if not already open) while the fluid infusion line 176 extends upward supported in one vertical raceway 222 as shown in FIG. 8. The upward direction of the branch of "Y" style line 156 coupled to the fluid infusion line 176, and the upward support of the fluid infusion line provides a "standpipe" that facilitates driving air out of the blood pump 150 and retrograde filling of the blood pump 150 and fluid infusion line 176 with prime solution. The Roberts clamp 197 is closed as shown in FIG. 9 after the fluid infusion line 176 is filled with prime solution. Antegrade filling of the oxygenator outlet line 188 is assisted by unclamping the tubing clamp at about C2 and applying the tubing clamp again at about C2 when prime solution reaches the arterial filter inlet 182.

Turning to FIG. 10, the 0.250 inch spike at the end of the fluid infusion line 176 is then inserted into the bayonet port at the free end of bag line 376 extending from sequestering bag 370. One of the Roberts clamps 384 and 195 is closed as shown in FIG. 10 when prime solution rises through the recirculation/cardioplegia line 174 and begins to fill the sequestering bag 370. Thus, upward filling of the oxygenator 160 and the pump 150 and the fluid infusion line 176 and recirculation/cardioplegia line 174 is accomplished to drive air bubbles upward and out of the venous blood pump 150 and oxygenator 160 and the lines coupled therewith as shown by the cross-hatching in FIGS. 9 and 10.

The tubing clamp at C1 is also released in FIG. 10 to allow the prime solution to rise upward through the VARD outlet 136, to fill the VARD 130, and to pass through the VARD inlet 132 into the venous return line 112. The prime solution rises upward through the venous return line 112, the utility connector 110, the TMC 38 BioTrend® connector 108, the bypass circuit 120, the arterial line 114 passing through the blood flow transducer connector 190, and through the arterial filter outlet 184 into the chamber of the arterial filter 180. The check valve 119 prevents prime solution from rising from the utility connector 110 through the arterial filter recirculation line 118 to the stopcock 187. The housing of the arterial filter 180 is preferably transparent so that the upward rising prime solution and any air bubbles can be seen. The stopcock 187 is closed when the prime solution starts to escape the arterial filter purge port 186.

The stopcock 135 is also opened so that prime solution begins to fill the upwardly extending VARD purge line 141 as shown in FIG. 10 and is then closed. As noted above, the VARD purge line 141 is supported to extend upward during priming by one vertical raceway 222 of the C-shaped arm 202 as shown in FIG. 8 so that air can escape through VARD purge line 141 and to atmosphere. At least the upper part of the housing of the VARD 130 is preferably transparent so that any air bubbles can be seen. The purge line segment 147 is inserted into the purge line pinch valve 410 to close the purge line segment 147 as the VARD purge line 141 begins to fill with prime solution. The stopcock 135 remains open, and the stopcocks 196, and 125 are opened. Stopcock 125 is then closed when prime solution rises and fills the venous blood pressure monitoring line 116 and the pressure isolator 117.

Thus, air is driven upward and out of the chambers of the VARD 130 and the arterial filter 180 as they are filled with prime solution as shown in the cross-hatching in FIG. 10. The Roberts clamps 161 and 165 remain open. In FIG. 11, the tubing clamp is applied at about C3 is removed to allow priming fluid to drain from prime solution bag 380 through the priming line 159, the pump 150, and the fluid infusion line 176 into the sequestering bag 370. The sequestering bag 370 is filled with sufficient prime solution to enable priming of the cardioplegia circuit through the cardioplegia port 177. It may be necessary to open Roberts clamp 163 to drain prime solution from the second prime solution bag 390 in filling sequestering bag 370.

The wall vacuum source is then coupled to the purge line distal end connector 143 via the vacuum line and liquid trap to provide a regulated −215 mmHg vacuum through the VARD purge line 141 when the pinch valve 410 is opened. The VARD sensor cable 450 is attached to the sensor element connector on VARD 130 and the cable connector 454 on the housing 402 of the AAR controller 400. The Roberts clamp 165 is closed, the tubing clamp at C2 is released, and the venous blood pump 150 is turned on at minimum flow.

The three stopcocks of sampling manifold 115 are then set to allow arterial blood flow and air to be drawn by the venous blood pump 150 through the arterial blood sampling line 172, check valve 121, the sampling manifold 115, line venous blood sampling line 106 and into the utility connector 110. Air is thereby vented out of the arterial filter recirculation line 118 and sampling manifold 115 through the utility connector 110 into the VARD 130 by the venous blood pump 150. The air that accumulates in the VARD upper chamber is then suctioned out through the line VARD purge line 141 when the AAR controller pinch valve is manually opened as described below. Arterial filter 180 and fitting 208 can be detached, inverted, and gently tapped so that the pumped prime solution moves any air in the arterial filter 180 out through the arterial filter outlet 184 and to the VARD 130. The arterial filter 180 and fitting 208 are then reinstalled into the fitting 208 and inspected visually for evidence of any air bubbles that may require repeating of the inverting and tapping steps. The stopcocks of the sampling manifold 115 is then reset to block flow.

At this point, the extracorporeal blood circuit 100 is primed. The pre-bypass loop 120 is disconnected, and table lines coupled to cannulae or elongated cannulae (herein referred to generally and collectively as table lines) can be attached to the quick disconnect connectors 102 and 104. The oxygen lines are coupled to the access ports 162 and 164 and the water lies are coupled to the water inlet 166 and water outlet 168 of the oxygenator 160.

AAR System and Method

In a further aspect of the present invention, an improved AAR system and method are provided that are capable of sensing and removing air and blood froth from VARD 130 while removing a minimal amount of liquid blood. The AAR system comprises the VARD 130 depicted in greater detail in FIGS. 12A, 12B and 13 functioning with an AAR controller 400 of the present invention depicted in FIGS. 14-15. The AAR system is capable of removing a continuous stream of air injected into the venous return line 112 at a rate of up to about 200 ml/min from VARD 130 after the AAR controller 400 is connected with the VARD 130 and made operational as described further below in reference to FIGS. 16-57. The AAR system preferably can handle a maximum rate of air removal of about 400 ml/min of air and blood froth. In addition, the AAR system is capable of removing a 50 cc bolus of air injected into the venous return line 112 over several seconds from VARD 130. The VARD 130 is advantageously employed with the AAR controller 400 performing the methods described herein, but the principles of design and operation of VARD 130 may be alternatively employed in other contexts.

The VARD 130 is preferably a modified conventional arterial blood filter having upper and lower air sensors. For example, VARD 130 may be a modified AFFINITY® Arterial Filter sold by Medtronic, Inc. Air entrapped in the venous blood is actively removed by a vacuum applied to the purge port 134 of VARD 130 through the VARD purge line 141. The VARD 130 preferably comprises a housing 142 having a hollow volume displacer 146 comprising an inverted cone that extends down into center of the venous blood chamber 140 from an upper end wall of the housing 142 and defines an annular upper VARD inlet chamber 148 and an annular lower VARD chamber 140. The housing 142 incorporates components enabling the filtering of the venous blood drawn through it by blood pump 150 and the detection and automatic removal of air and froth rising to the VARD inlet chamber 148. The lower cap or portion of housing 142 including the outlet port 136 are not shown in FIGS. 12A and 12B.

Normally, the lower VARD chamber 140 and the upper inlet chamber 148 of VARD 130 is filled with blood as venous blood pump 150 draws venous blood through upper inlet 144 coupled to venous return line 112 into VARD inlet chamber 148, through an internally disposed filter element (not shown) and out of the lower VARD outlet 136. A screen or other conventional bubble-trapping device may be inserted in venous blood chamber 140 below the VARD inlet chamber 148 to trap air bubbles in the blood stream and cause them to stay in the VARD inlet chamber 148. The VARD 130 differs from the arterial blood filter 180 in that it incorporates a sensor array 138 comprising four piezoelectric elements 138A, 138B and 138C, 138D that are arranged in orthogonally disposed pairs of piezoelectric elements 138A, 138B and 138C, 138D as shown in FIGS. 12A, 12B, and 13 that sense the level of blood within the upper VARD inlet chamber 148 or in the lower VARD chamber 140.

In one embodiment of the present invention, a first or upper pair of ultrasonic piezoelectric elements 138A and 138B is disposed across the purge port 134 and a second or lower pair of ultrasonic piezoelectric elements 138A and 138B is disposed below the VARD inlet chamber 148 forming the sensor array 138. The piezoelectric elements 138A and 138C are disposed, preferably by bonding, on the exterior surface of the cavity inside the volume displacer 146. The piezoelectric elements 138B and 138D are disposed, preferably by bonding, on the exterior surface of the housing extending between the upper portion of the VARD inlet chamber 148 to the purge port 134 and the housing 142, respectively.

Figure 12B:
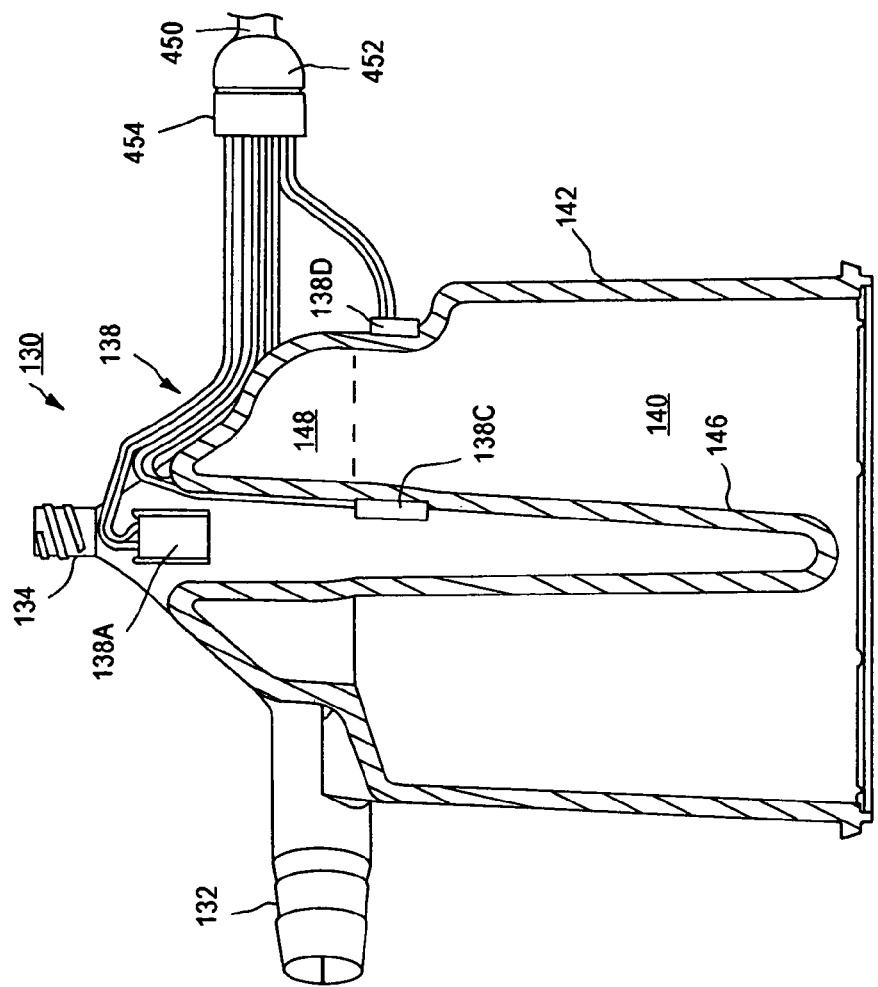
FIGS. 12A and 12B are cross-section views of one embodiment of a VARD employed in the disposable, integrated extracorporeal blood circuit in accordance with the present invention.
Figure 12A:
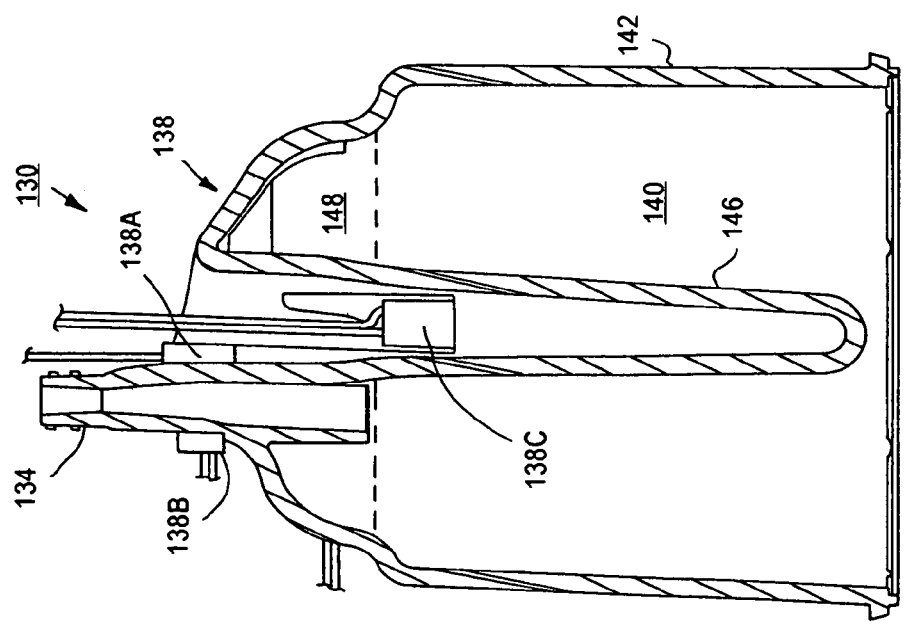

The piezoelectric elements 138A, 138B and 138C, 138D utilized herein may preferably be formed employing conventional, rectangular, piezoelectric crystal layers of a thickness selected to be resonant in the range of 1 to 3 MHz, and specifically about 2.25 MHz and mounted as depicted in FIGS. 12A and 12B and described below. Conductive thin film electrodes are deposited, plated or otherwise applied to the major surfaces of the piezoelectric crystal layers, and conductors are welded or soldered to the electrodes. As is well known, such a piezoelectric element can be excited to oscillate in a thickness mode by an RF signal applied, via the conductors and electrodes, across the thickness of the crystal layer. The resulting mechanical vibration of the transmitting piezoelectric element is transmitted though a fluid chamber or conduit. Ultrasonic vibrations emitted by the transmitting piezoelectric element pass through the liquid in the chamber or conduit to impinge upon the receiving piezoelectric element. The receiving piezoelectric element vibrates in sympathy with the ultrasonic vibrations and produces an alternating current potential proportional to the relative degree of vibratory coupling of the transmitting and receiving piezoelectric elements. The degree of coupling of the ultrasonic vibrations abruptly drops when air is introduced between the transmitting and receiving piezoelectric elements, and the output amplitude of the signal generated by the receiving piezoelectric element drops proportionally.

Therefore, one piezoelectric element of each pair 138A, 138B and 138C, 138D is used as a transmitting crystal, and the other piezoelectric element of each pair 138A, 138B and 138C, 138D is used as the signal receiver. It is preferable to use pairs of piezoelectric elements, one a transmitter and the other a receiver, rather than to employ a single piezoelectric element used as both transmitter and receiver, because a pair of piezoelectric elements provides a more robust sensing system. The presence of liquid or air between the transmitting piezoelectric element and the receiving piezoelectric element differentially attenuates the transmitted ultrasonic signal in a manner that can be detected from the electrical signal output by the receiving piezoelectric element in response to the ultrasonic signal.

Figure 14:
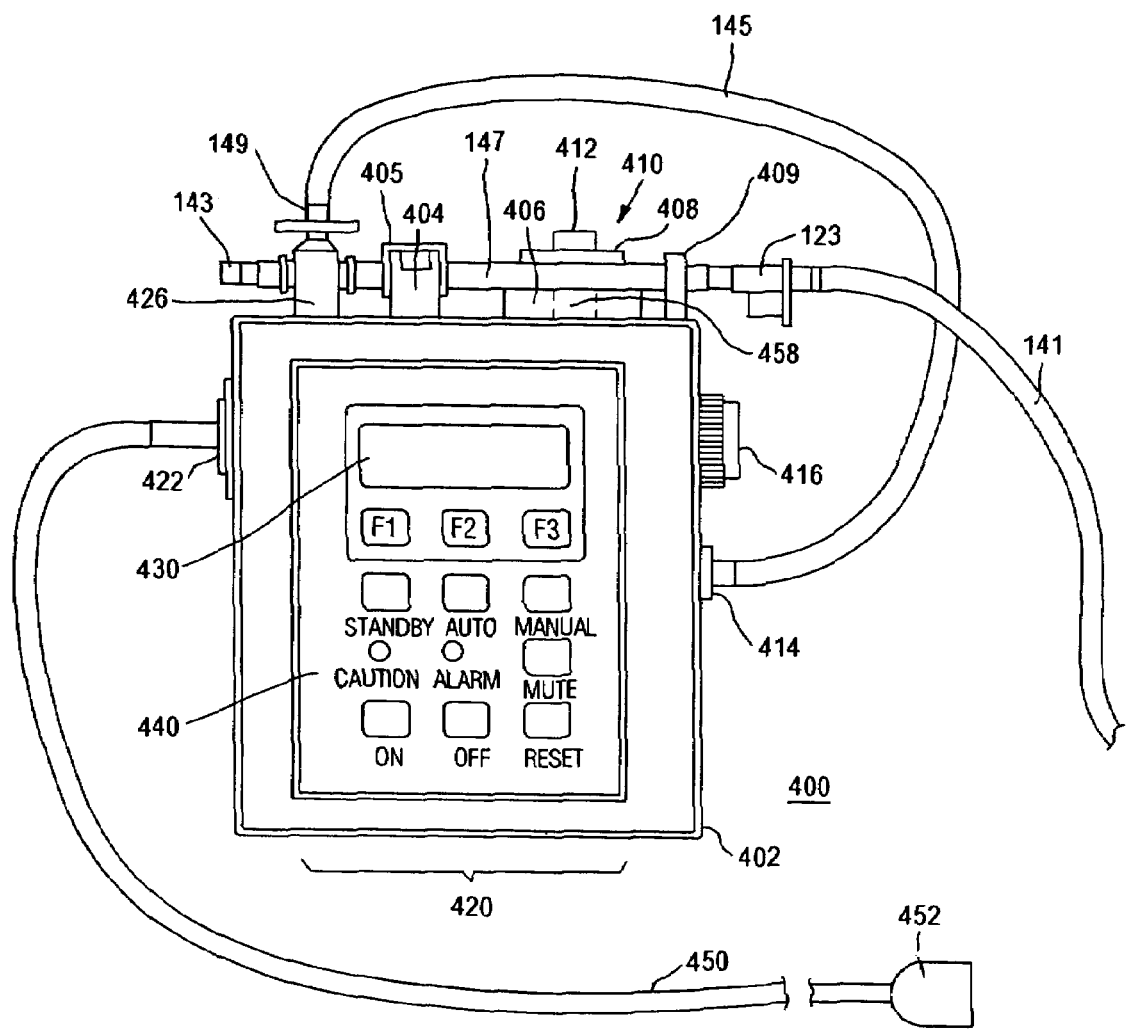
FIG. 14 is a plan view of an AAR controller employed in the practice of the present invention.

The eight conductors coupled to the eight electrodes of the piezoelectric elements 138A, 138B and 138C, 138D are extended to VARD connector 454 (depicted schematically in FIG. 12B) mounted on the VARD housing 142. The distal cable connector 452 of reusable VARD cable 450 extending to AAR controller 400 shown in FIG. 14 is intended to be coupled to the VARD connector 454. The VARD cable 450 comprises 10 conductors, and the distal cable connector 452 and VARD connector 454 comprise 10 contact elements. Eight of the cable conductors are coupled through eight of the mating connector elements with the eight conductive thin film electrodes of the sensor array 138. Two further connector elements of the VARD connector 454 are electrically in common, and a continuity check can be performed by the VARD circuitry through the two cable conductors joined when contacting the two connector elements. In this way, any cable or connector failure can be immediately detected and an alarm sounded by the VARD 400.

The excitation of the transmitting piezoelectric elements and the processing of the signals generated by the receiving piezoelectric elements is performed by an electronic circuit of the AAR controller 400 coupled to the cable. A microprocessor or controller of the electronic circuit of AAR controller 400 utilizes the processed received signals to determine when the liquid level is below the upper pair of piezoelectric elements 138A, 138B and opens a pinch valve 410 engaging and normally closing the silicone rubber purge line segment 147 to allow suction to be applied through the VARD purge line 141 to purge port 134 to evacuate the air and froth within the upper VARD inlet chamber 148 below the level of the piezoelectric elements 138A, 138B. The vacuum applied at the purge port 134 overcomes the negative pressure imposed by venous blood pump 150 within VARD inlet chamber 148 and draws out the accumulated air through the purge port 134. An audible and/or visual warning may be activated to indicate the presence of air within the VARD inlet chamber 148. For example, an audible and/or visual alarm may be activated if liquid, e.g., blood or saline, is not sensed for approximately five seconds. The warning may continue while air is being removed. Detection of liquid between the upper pair of piezoelectric elements 138A, 138B causes the controller to close the pinch valve 410 to halt the application of vacuum through the VARD purge line 141.

The second, lower pair of piezoelectric elements 138C, 138D located just above the transition of the venous blood chamber 140 with the VARD inlet chamber 148 provides a backup to the first, upper pair of piezoelectric elements 138A, 138B, should the first, upper pair of piezoelectric elements fail. The second, lower pair of piezoelectric elements 138C, 138D also provide a way to detect if the liquid level has dropped below a minimally acceptable level, even though pinch valve 410 has been opened by the detection of air by the first, upper pair of piezoelectric elements 138A, 138B. A further distinctive audible and/or visual alarm may be activated if the blood level falls below the second pair of piezoelectric elements 138C, 138D.

In one embodiment of the present invention, the piezoelectric elements 138A, 138B, 138C, 138D are preferably rectangular in shape and arranged so that the long axis of the transmitter piezoelectric element 138A, 138C is rotated 90° from the long axis of the receiver piezoelectric element 138B, 138D in the manner shown in FIG. 10. This configuration provides better transmission overlap at 139 of the transmitted ultrasonic signal to the receiver piezoelectric element of the pair.

Figure 13A:
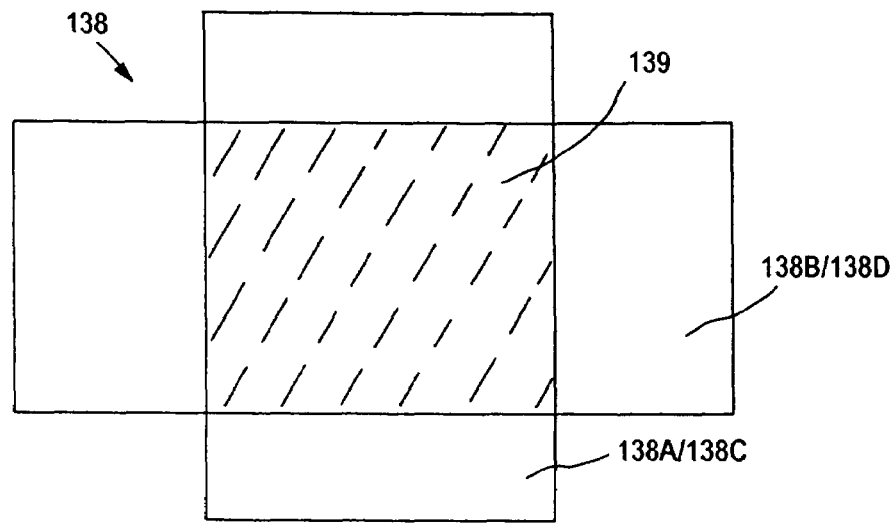
FIG. 13A is a schematic view of the orientation of piezoelectric elements employed in the VARD illustrated in FIGS. 12A and 12B in accordance with the present invention.
Figure 13B:
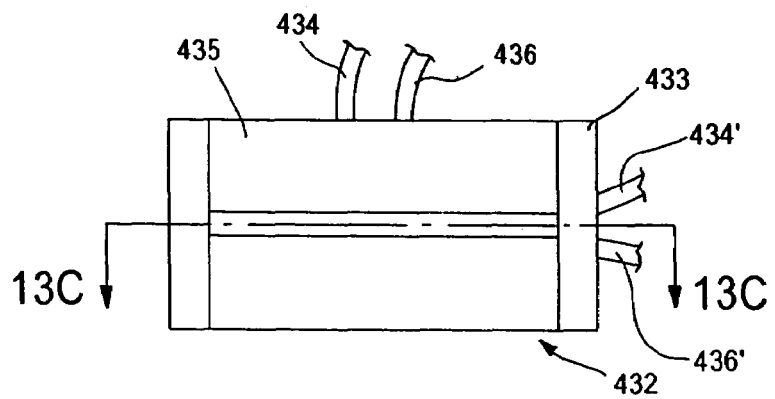
FIG. 13B is a plan view of a piezoelectric element employed in the VARD illustrated in FIGS. 12A and 12B.
Figure 13C:
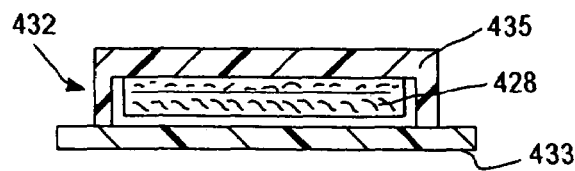
FIG. 13C is a side cross-section view taken along lines 13C-13C in FIG. 13B of the internal components of the piezoelectric element.

The piezoelectric elements 138A, 138B, 138C and 138D are also illustrated in FIGS. 13B-13E. Each piezoelectric element 138A, 138B, 138C and 138D comprises a piezoelectric crystal assembly 428 encased within a nonconductive element housing 432. The element housing 432 preferably comprises a lid 435 and a base 433, wherein the base 433 is longer than the lid 435. The lid 435 has an upwardly extending rib as shown in FIGS. 13B and 13C. The sides of base 433 extend past the lid 435 as shown in FIG. 13C.

A pair of conductors 434 and 436 extend through the long side of lid 435 of the element housing 432 in the configuration of piezoelectric elements 138B and 138D. An alternative pair of conductors 434' and 436' extend through the short side of lid 435 of the element housing 432 in the configuration of piezoelectric elements 138A and 138C. In each configuration, the conductors 434, 436 or 434', 436' are coupled to thin film electrodes formed on the major opposed surfaces of the piezoelectric crystal layer 428 within the lid 435. The piezoelectric crystal layer 428 may be formed of any suitable piezoelectric ceramic bearing the opposed surface electrodes. One surface electrode is adhered to the base 433 that is to be applied against the slot side wall of the VARD housing 142.

Figure 13D:
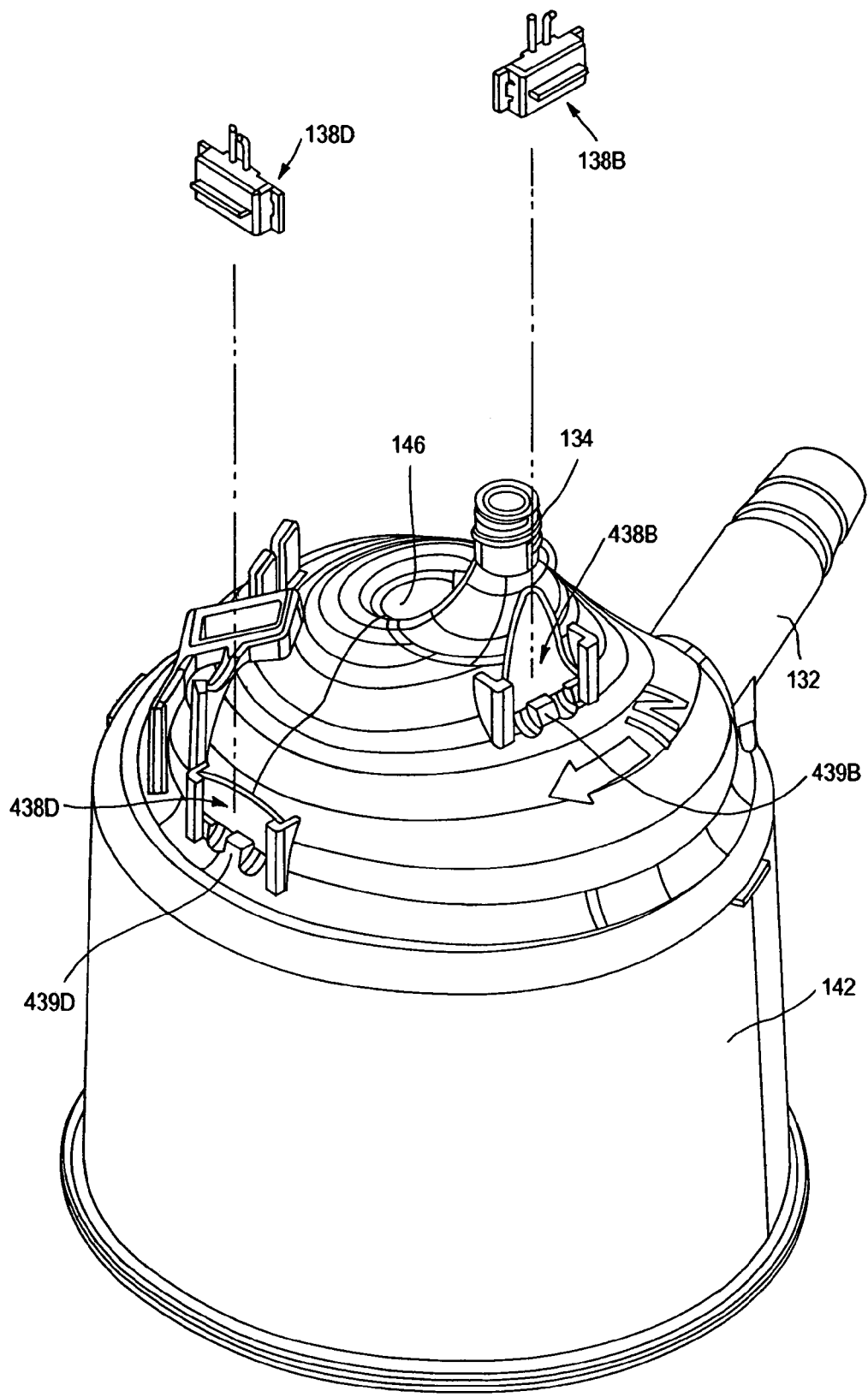
FIG. 13D is a partial exploded perspective view of the VARD and piezoelectric elements.
Figure 13E:
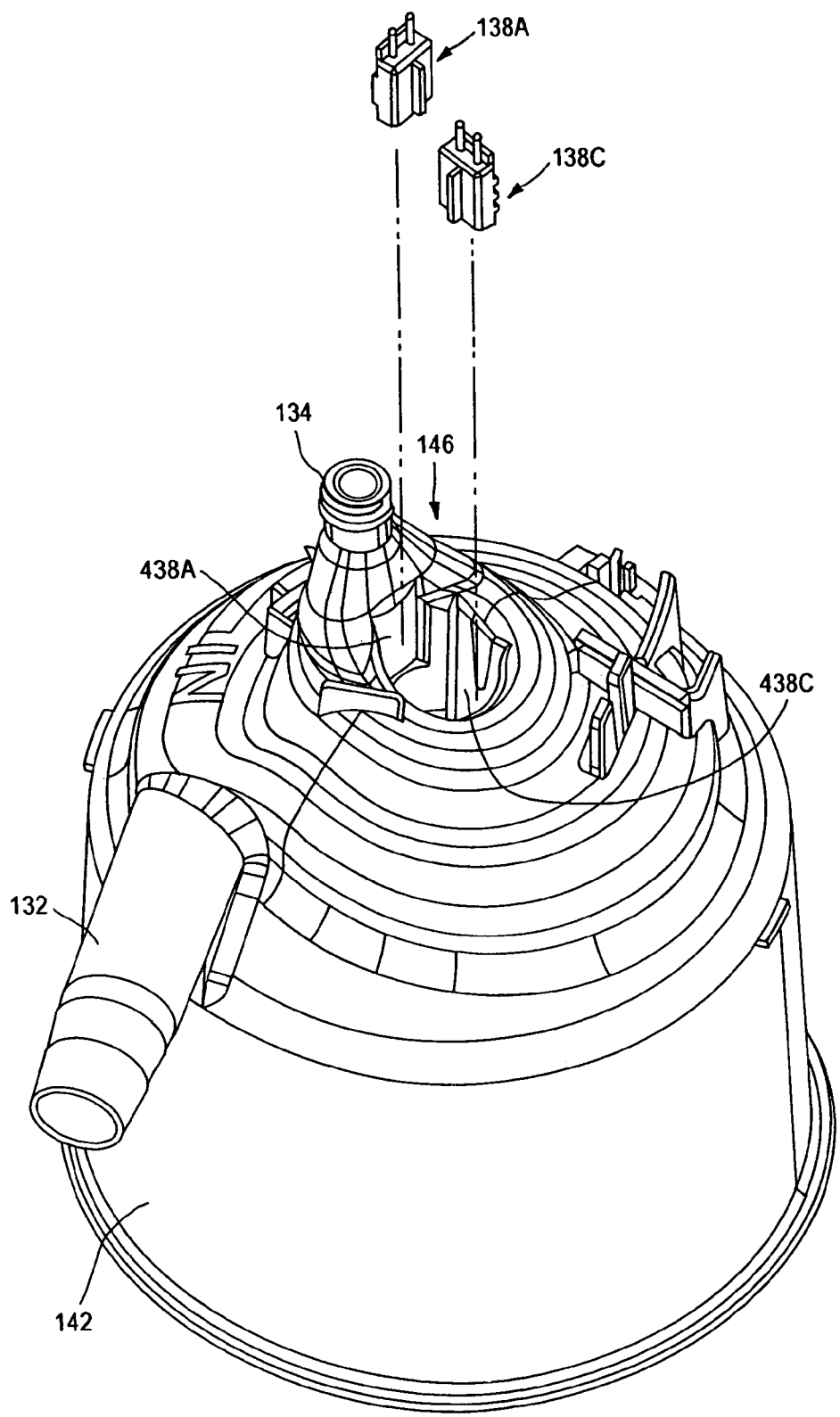
FIG. 13E is a further partial exploded perspective view of the VARD and piezoelectric elements.

Preferred ways of mounting the piezoelectric elements 138A, 138B, 138C and 138D to the VARD housing 142 are illustrated in FIGS. 13D and 13E. Four slots 438A, 438B, 438C, and 438D shaped to conform to the element housing 432 are formed on the outer wall of the housing 142. The slots 438B and 438D shown in FIG. 13D are shaped to receive the respective piezoelectric elements 138B and 138D extending orthogonally to the axis of the VARD housing 142 and the hollow volume displacer 146 as shown in FIGS. 12A, 12B, and 13A. Each slot 438B and 438D, is shaped to receive the lid 433 that is applied against he housing wall. Stops 439B and 439D fit against the side of container 435 when the lid 433 is slipped into the respective slot 438B and 438D against the housing wall. The slots 438A and 438C shown in FIG. 13E are formed within the wall of hollow volume displacer 146 and are shaped to receive the respective piezoelectric elements 138A and 138C extending in alignment with the axis of the VARD housing 142 and the hollow volume displacer 146 as shown in FIGS. 12A, 12B and 13A.

During assembly, the outer surface of the nonconductive element housing 432 is coated with a gel adhesive that is cured when exposed to UV light, for example, and is fitted into the slots 438A, 438B, 438C, and 438D. The VARD housing 142 is exposed to UV light to cure the adhesive.

Figure 15:
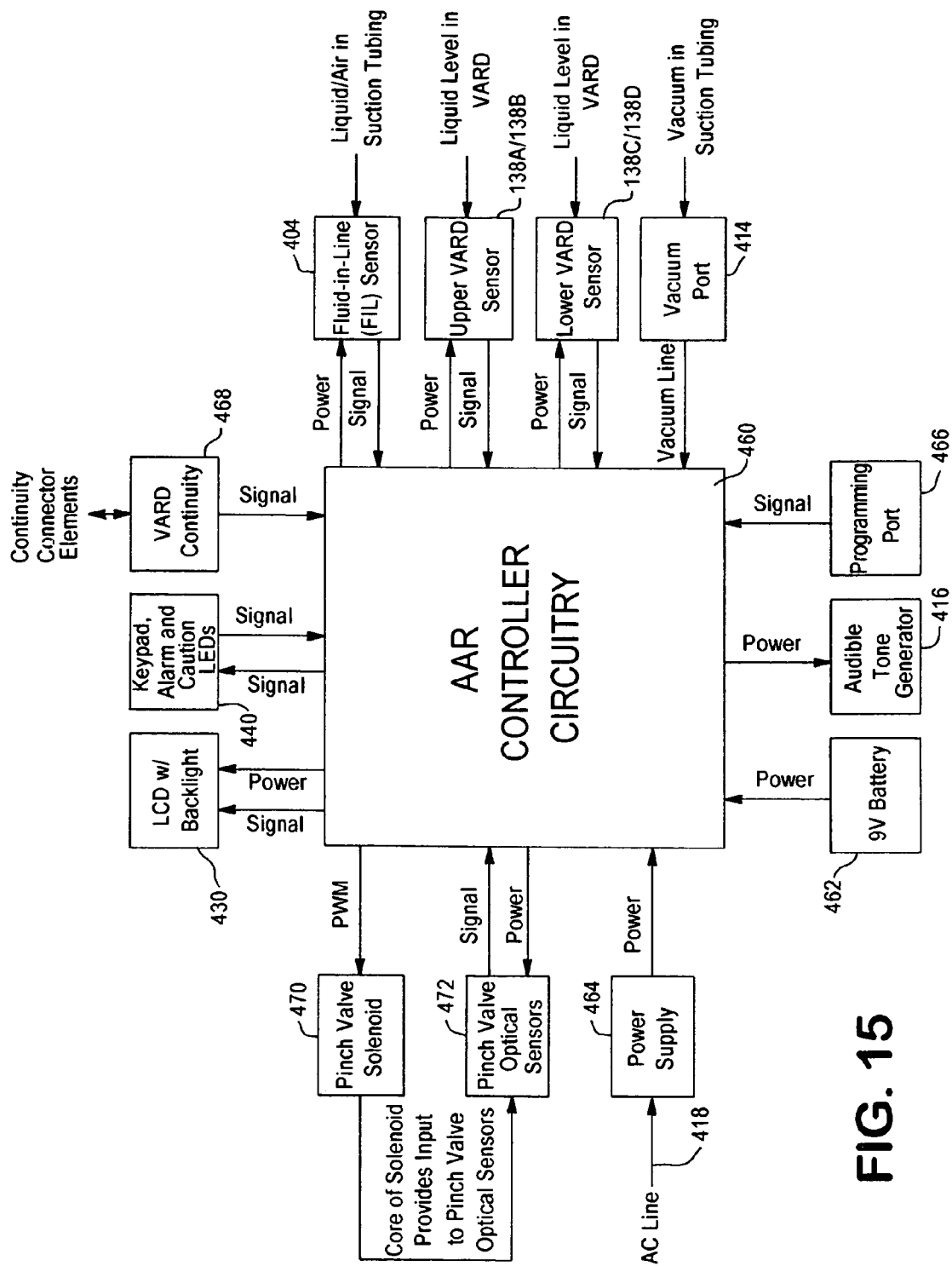
FIG. 15 is a system block diagram of the AAR controller of FIG. 14.

The AAR controller 400 is shown in greater detail in FIGS. 14 and 15 comprising an AAR controller operating system that includes AAR controller circuitry 460 and electrical components coupled thereto to function as described further herein. The AAR controller circuitry 460 and certain components coupled to the circuitry shown in FIG. 15 are powered normally by an AC line input 418 to power supply 464 but can be powered by a backup battery 462 in case of general power failure or failure of the power supply 464. The power supply 464 comprises redundant power supply circuits and switching circuitry for selecting an operable power supply circuit to deliver operating power. The AAR controller circuitry 460 takes the form of a microprocessor-based computer operating under control of software stored in RAM and can be programmed via the programming port 466.

In FIG. 14, a clamp (not shown) on the rear side of housing 402 of the AAR controller 400 is adapted to be attached to the left support arm 322 of the reusable circuit holder 300 shown in FIG. 6. After attachment, a perfusionist interface 420 comprising an LCD screen 430 and a control panel 440 are disposed outward to facilitate seeing the displayed text in LCD screen 430 and warning lights and to facilitate use of the soft keys of the control panel 440.

The FIL sensor 404 disposed on the upper surface of the housing 402 has a hinged cover or latch 405 extending across an upward opening slot so that the slot cross-section area is constant when the latch 405 is closed. The latch 405 preferably has a downward extending bar that extends into the FIL sensor upward opening slot. In use, the FIL sensor latch 405 is opened, the VARD purge line 141 is extended laterally across the oxygenator 160, a portion of the compressible VARD purge line segment 147 is fitted into the FIL sensor slot, and the FIL sensor latch 405 is closed. The portion of the compressible VARD purge line segment 147 fitted into the FIL sensor slot is compressed by the downwardly extending bar when the latch 405 is closed so that the tubing wall is pressed tightly and uniformly against the opposed side walls of the FIL sensor slot. The purge line distal end connector 143 is fitted into the upward opening slot of clip 426 with the isolation filter 149 and the vacuum sensor line 145 extending vertically.

The pinch valve 410 disposed on the upper surface of the housing 402 comprises upper and lower members 406 and 408 that define a side opening slot between them that a further section or portion of the compressible VARD purge line segment 147 can be fitted into. A purge line guide post 409 also extends upward from the upper surface of the housing 402 so that the purge line segment 147 is routed between the purge line guide post 409 and the pinch valve 410 when the pinch valve 410 is closed and the purge line segment 147 is not yet positioned in the pinch valve slot.

A pinch rod 458 extends upward from within the AAR controller housing 402 under spring tension. The pinch rod 458 extends transversely into and across the slot between the upper and lower members 406 and 408. The pinch rod 458 can be moved downward out of the pinch valve slot by depression of mechanical release button 412 to insert a portion of the compressible VARD purge line segment 147 into the slot. The purge line guide post 409 and the FIL sensor slot holding another portion of the VARD purge line segment 147 as described above keep the portion of the VARD purge line segment 147 within the pinch valve slot when the pinch rod 458 is later moved downward out of the pinch valve slot as described below.

The pinch rod 458 again extends upward under spring tension to compress the section of compressible VARD purge line segment 147 closed upon release of the mechanical release button 412. The pinch rod 458 cannot extend all the way across the slot between the upper and lower members 406 and 408 when a portion of the purge line segment 147 is fitted into the slot. The pinch rod 130 can be retracted by again depressing mechanical release button 412. The pinch rod 130 extends through the core of a solenoid coil that is powered under the control of the circuitry of the AAR controller 400 to draw the pinch rod 458 downward to the pinch valve open position.

The tubing of purge line segment 147 inserted into the pinch valve and FIL sensor slots is composed of a soft, biocompatible material having a suitable durability and resilience, e.g., silicone rubber tubing. Preferably, the silicone rubber tubing of purge line segment 147 has a 0.250 inch ID and a 0.375 inch OD, and the silicone rubber tubing has sufficient resilience to restore the lumen diameter to at least ¾ of its nominal lumen diameter upon retraction of the pinch rod 130.

Typically, if air is sensed in the VARD 130, fluid would not be sensed in the purge line segment 147 by the FIL sensor 404, and so the pinch valve would close 410 before blood is suctioned all the way to the FIL sensor 404. However, the intermittent detection and purging of air through the purge line 141 will in time draw boluses of blood or blood-air froth out of the VARD 130 through the purge line segment 147 such that detection of blood by the FIL sensor 404 could cause the AAR operating system to inappropriately close the pinch valve 410 while air is still sensed in the VARD 130. Therefore, preferably the sensor output signal of the FIL sensor 404 is processed over a time window that minimizes this possibility.

More particularly, the FIL sensor 404 is preferably a high frequency acoustic sensor employing a piezoelectric element disposed on one side of the FIL sensor slot that is energized to emit acoustic energy and a piezoelectric element disposed on the other side of the FIL sensor slot that is coupled to FIL sensor signal processing circuitry to function as a receiver element. The receiver element provides a FIL sensor output signal that varies in amplitude as a function of the modulation of the emitted acoustic energy by air or fluid in the portion of the purge line segment 147 within the FIL sensor slot. The FIL sensor output signal is attenuated by fluid in the portion of the purge line segment 147 within the FIL sensor slot. The FIL sensor output signal is sampled at a predetermined sampling rate, and the sampled amplitude is compared to a threshold set for air. Generally speaking, a count in a hardware or software counter of the AAR circuitry 460 (FIG. 15) is incremented or decremented by the high or low output of the comparator. For example, the count may be incremented each time that the sampled FIL sensor output signal is attenuated by fluid in the line and is decremented or reset to zero each time that the sampled FIL sensor output signal has an amplitude that is not attenuated by air in the line. A FIL error state is only declared when a predetermined count is met. Therefore, intermittent boluses of fluid, particularly the patient's venous blood, and blood-air froth do not trigger declaration of the FIL error state.

The distal end of the vacuum sensor line 145 is attached to a vacuum sensor input 414 on a first side of the housing 402 as shown in FIG. 14. An audible tone generator 416 is mounted to the first side of the housing 402. An AC power cord 418 is attached to a receptacle in the second side of the housing 402. The reusable VARD sensor cable 450 containing the eight conductors attached to the eight surface electrodes of the piezoelectric elements 138A, 138B, 138C and 138D and the two continuity checking conductors extends between the cable connector 452 and the cable connector 422 on the second side of the housing 402. The purge line segment 147 fitted into the slots of the FIL sensor 404 and a pinch valve 410 is preferably at the same level as the VARD purge port 134, and the height of the AAR controller 400 is adjustable by adjusting the electronics arm assembly 314 along the mast 302.

The soft keys in the control panel 440 depicted in FIG. 14 include an "ON" key and an "OFF" key that can be depressed by the perfusionist to power up and power down, respectively, the AAR controller circuitry 460 and the various sensors and electrical components coupled to the circuitry. A "RESET" key can be depressed at any time by the perfusionist to reset the controller signal processor and restart the AAR operating algorithm in the Self-Test Mode described further below. A yellow "Caution" light and a red "Alarm" light are lit when the signal processor determines certain respective caution and alarm conditions. The audible tone generator 416 emits respective audible caution and alarm tones. A "MUTE" switch can be depressed to silence the audible tones. The "STANDBY" and "AUTO" keys can be depressed to initiate the respective Standby and Automatic Modes described further below. The "MANUAL" soft key can be depressed to open the pinch valve 410 in the Standby and Automatic Modes if the AAR operating system is being powered by the power supply 464 and only for as long as the "MANUAL" soft key remains depressed. The function keys F1, F2, and F3 can be depressed in response to a message displayed along the lower edge of the LCD screen 430 in alignment with the particular function key.

Referring to FIG. 15, the pinch rod 458 is axially aligned with and coupled to a solenoid core that moves downward into housing 402 when the solenoid coil is energized or when the mechanical release button 412 is manually depressed. A solenoid driver 470 is selectively actuated by AAR controller circuitry 460 automatically or when the MANUAL key is depressed to drive the pinch rod 458 downward overcoming the biasing force of the spring. Preferably, a plurality of optical pinch valve sensors 472 are provided within the housing 402 to determine the position of the downwardly extending pinch rod 458 or solenoid core coupled to the pinch rod 458. For example, a plurality of holes are formed through the pinch rod 458, and light emitters and photocells arranged along the length of the pinch rod 458 so that emitted light passing through a particular hole is detected by a photocell of an optical position sensor to generate an output signal. The output signals of the optical position sensors 472 signify whether the pinch rod 410 is in a fully open position, a closed position against the portion of the purge line segment 147 fitted into the pinch valve slot, and a fully closed position extending all the way across the pinch valve slot. The output signals of the pinch rod position sensors 472 are also employed to confirm that the pinch rod 458 has moved from one position to the other position in response to the applied appropriate command or is in an improper position and malfunctioning. Pinch rod positions other than these fully open, closed or fully closed positions that are sensed at inappropriate times are considered error positions or states, and an audible and visible alarm are emitted and a valve error message is displayed on LCD screen 430 as described below.

The purging operation in the Automatic Mode is dependent upon a number of conditions and sensor input signals that effect the automatic opening and closing of the pinch valve 410. The AAR controller circuitry 460 and the solenoid that moves the pinch rod 458 must be powered by an operational power supply 464 rather than the backup battery 462 in order to automatically open the pinch valve 410. Generally speaking, the automatic opening of the pinch valve 410 in the Automatic Mode takes place when output signal generated by one of the upper air sensor piezoelectric elements 138A, 138B (or the lower air sensor piezoelectric elements 138C, 138D) indicates that air is present in the VARD inlet chamber 148 and when specific error states are not declared. The conditions and states are continually monitored, and a declared error state inhibits the opening of the pinch valve 410, that is interrupts and closes the purge valve if purging has already started or prevents the purge valve opening if purging has not started. The depression of the OFF, STANDBY and RESET keys also both interrupt the opening of the pinch valve 410 and terminate the Automatic Mode. Mechanical opening of the purge valve 410 is possible at any time.

Figure 53:
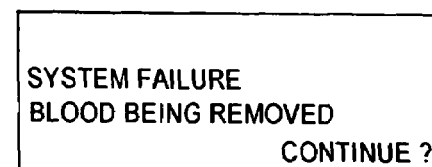

The error states declared in the Automatic Mode that inhibit opening of the purge valve 410 are indicated by error messages displayed on the LCD screen 430 depicted in FIGS. 50-56 and emission of light and sound Cautions that alert the perfusionist to take appropriate corrective action. The declared error states include low suction (FIG. 55), failure of the VARD sensors (FIG. 54), a pinch valve failure (FIGS. 50-52), failure of the VARD cable continuity check (FIG. 56), and a FIL error state (FIG. 53). A vacuum threshold level must be met by the vacuum in the vacuum line segment 147 measured through vacuum sensor line 145 and isolation filter 149 by the vacuum sensor coupled to vacuum sensor input 414. The failure of one or more of the piezoelectric elements 138 is declared in the event that the air sensor signal from the receiver one of the lower piezoelectric element 138C or 138D signifies detection of air while the air sensor signal from the receiver one of the upper piezoelectric element 138A or 138B signifies detection of fluid. A pinch valve error state is declared when the pinch rod 458 does not move to or from the open or closed position or is in an improper position. A VARD cable connection failure is declared when the continually check results in an open circuit as described above. A FIL error state is declared when blood is sensed in the purge line segment 147 for the required time as described above. The perfusionist then must take appropriate action, which may include replacing the AAR controller 400 or the VARD cable 450 or manually opening the pinch valve 410 to purge air.

If the AAR controller circuitry 460 is powered by power supply 464, the operator can manually evacuate the air by depressing the MANUAL key on the control panel 440 if no error state is declared. When the MANUAL key is depressed in the absence of an error state, power is supplied to the solenoid to draw the pinch rod 458 down to open the pinch valve 410 thereby allowing the vacuum source coupled to nozzle 143 to remove air from the VARD 130 through the VARD purge line 141. The LCD screen 430 displays "VALVE OPEN" while the MANUAL key is depressed, although the Automatic Mode remains enabled when pressing the MANUAL key. The perfusionist releases the MANUAL key to close the pinch valve 410 once air has been removed from the VARD 130. The Alert message "AIR IN VARD" automatically clears from the LCD screen 430. The yellow LED stops flashing and the audible tone stops.

The method of operation of the AAR system in the Self-Test, Standby, and automatic (AUTO) operating modes and in response to detected normal and abnormal conditions and battery power states is illustrated in the flowcharts of FIGS. 16A-16B and 17A-17B and the LCD screen displays in FIGS. 18-57. It is assumed that the above-described components of the disposable, integrated extracorporeal blood circuit 100 are spatially arranged and supported in 3-D space as shown in FIG. 5 in relation to the patient on the operating table by the disposable circuit support module 200 and reusable circuit holder 300. It is also assumed that all operational connections, sensors, lines and the like, are made with components and lines of the extracorporeal blood circuit 100 as described above, and that the priming solution bags 380 and 390 and the sequestering bag 370 are supported by the IV hangar 360 with the lines connected in preparation for priming as shown in FIG. 9. The reusable VARD sensor cable 450 extends from the VARD connector 454 laterally through channel 332 and is connected with the AAR controller VARD connector 422. At this point, the purge line segment 147 is routed to extend upward for priming, and the VARD controller 400 is connected to an AC power line.

Figure 16A:
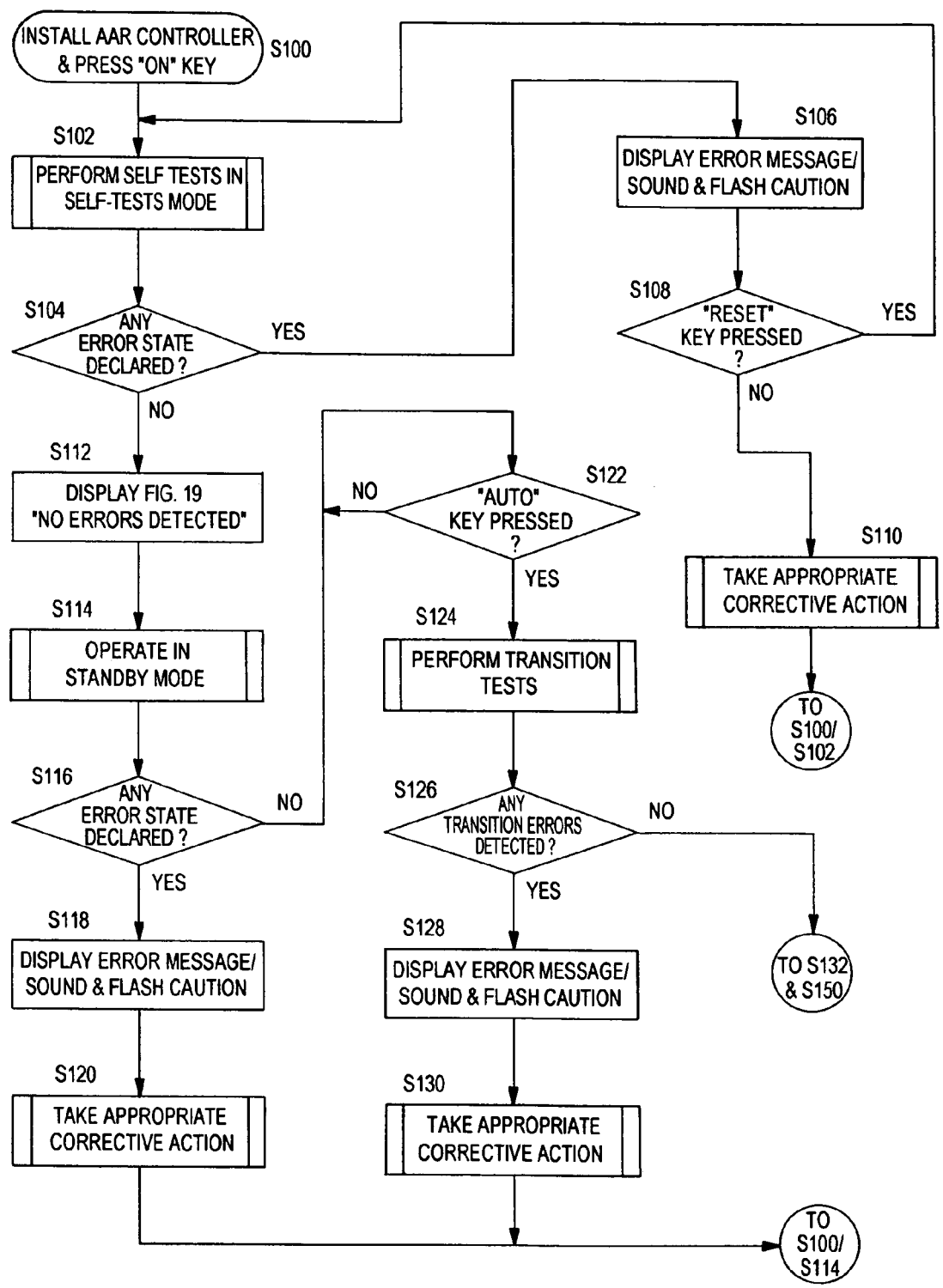
FIGS. 16A and 16B are a high level flow chart illustrating the Self Test, Standby, and Automatic Modes of operation of the AAR system of the present invention.
Figure 18:
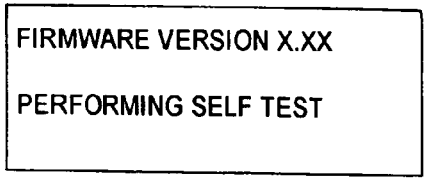
FIG. 18 is an LCD screen display during the Self-Test Mode.

Turning to FIG. 16A, the AAR controller circuitry 460 commences a self-test operating mode in step S102 when the "ON" key is depressed in starting step S100. A solid LCD display appears in LCD display screen 430 for 2 seconds, for example, followed by a display of the version of the installed software as shown in FIG. 18, to verify proper operation of the LCD display screen 430. Furthermore, both the yellow (Caution) and red (Alarm) LEDs on control panel 440 flash momentarily to verify proper operation when the "ON" key is depressed, and a series of "chirp" sounds are emitted by the audible tone generator 416 for several seconds to verify proper operation. The perfusionist is expected to observe or hear the failure of these components and to check the power line connection and backup battery, repeat start up, and to replace the AAR controller 400 if does not pass these initial self-tests.

Further self-test operations ensue in step S102 if these components of the AAR controller 400 function properly. The backup battery 462, software, and pinch valve 410 are subjected to self-test in step S102 to test proper state or function upon power up. Failure messages shown in FIGS. 30-36 are displayed in step S106 on LCD screen 430 in response to certain declared self-test failures. The self-tests are repeated in step S102 if the perfusionist depresses the "RESET" key as detected in step S108. The perfusionist is expected to take appropriate action in step S110 if the self-test failure persists, particularly to replace the AAR controller 400 and start over at step S100 if the self-test failure messages of FIGS. 30-33 are displayed.

In one of the self-tests, a software cyclic redundancy check (CRC) is run in step S102 to ensure that the software is functioning correctly. In step S106, the LCD screen 430 displays the message appearing in FIG. 30 instructing the perfusionist to replace the AAR controller 400 with a backup unit in step S108 if the CRC failure is declared.

The pinch valve 410 is subjected to mechanical function and software self-tests. The pinch valve solenoid 470 is powered in response to a software instruction to move the pinch rod 458 upward to the closed position and downward to the open position. The response and position of the pinch rod 458 is detected employing the pinch valve optical sensors 472. The LCD screen 430 displays the message of FIG. 31 or FIG. 32 in step S106 if a pinch valve hardware failure is found. The LCD screen displays the message of FIG. 33 in step S106 if a pinch valve software failure is found. Again, the perfusionist can depress the RESET key per step S108, and the AAR controller 400 is to be replaced by a backup unit per step S110 if the pinch valve self-test failure is repeated.

Figure 34:
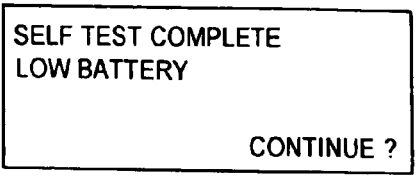
Figure 35:
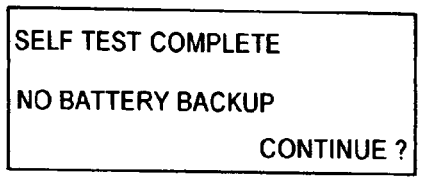
Figure 36:
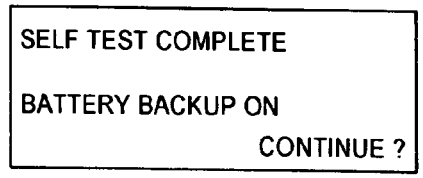

The power states of the AAR controller 400 are also determined, and the LCD screen 430 displays one of the messages of FIGS. 34-36 in step S106 if a power state failure is detected. While operating algorithm of the AAR controller 400 can be powered by the battery 462, use of line power applied to one of the redundant power supply circuits in power supply 464 is required to power the solenoid and is otherwise preferred since the battery power can deplete during the cardiac bypass procedure. The power state self-tests determine whether the AAR controller circuitry 460 is being powered by the battery 462 or the power supply 464. The power state self-tests also determine that a battery 462 is or is not present in its compartment and the current state of depletion of battery power, if the battery 462 is present. Thus, the perfusionist is instructed to take the appropriate action per step S110 if the battery power is low (FIG. 34), is not present (FIG. 35) or if battery backup is "ON" (FIG. 36) indicating a power supply failure or mains failure or simply that the AAR controller power cord is not plugged into mains power. The LCD screen displays of FIGS. 34-36 highlight the F3 key with the word "CONTINUE?" indicating that the perfusionist can proceed, if necessary, to the Standby Mode and employ the AAR controller 400 in battery backup, which may be necessary under certain conditions.

Figure 19:
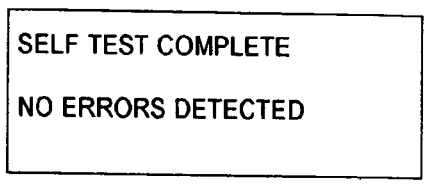
FIG. 19 is an LCD screen display during the Standby Mode.

The LCD screen 430 displays "NO ERRORS DETECTED" in step S112 as shown in FIG. 19 upon successful completion of the Self-Test mode or upon pressing the F3 key in response to the LCD screen displays of FIGS. 34-36. The operating algorithm automatically switches to the Standby Mode in step S114. The LCD screen 430 displays the message shown in FIG. 20 indicating that the pinch valve is in the normally closed (pinch rod 458 is up) state and that highlights the F2 key as "MENU" at the bottom of the LCD screen 430 unless an error state is immediately detected in step S116. Various conditions are also monitored when the operating algorithm is in the Standby Mode of step S114, and any corresponding error states are detected in step S116. In step S118, one of the error messages of FIGS. 37-42 is displayed on LCD screen 430, the Caution LED light is flashed, and the Caution note sounds. The MUTE key can be depressed to halt emission of the Caution sounds. The perfusionist can take appropriate action in step S120. The operating algorithm remains in the STANDBY Mode while action is taken to correct the condition causing the declaration of an error state or condition unless it is necessary to replace the AAR controller 400. In that case, the replacement AAR controller is installed and connected as described above in step S100, and the Standby Mode of step S114 is again entered upon successful completion of steps S102-S112.

Figure 37:
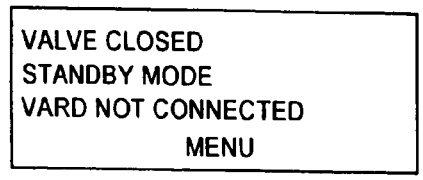

For example, a VARD cable continuity check is periodically conducted, and the message of FIG. 37 is displayed if the VARD cable connector 452 (FIG. 14) is not connected to the VARD connector 454 (FIG. 12B) as indicated by the failure of the continuity check performed in block 468 (FIG. 15). The VARD cable 450 can be reconnected or replaced in step S120.

Figure 38:
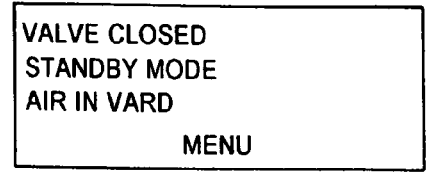
FIGS. 37-42 are LCD screen displays indicating error and system power states during the Standby Mode.

The message of FIG. 38 is displayed on LCD screen 430, and the corresponding Caution light and sound emitted when air is detected between the lower piezoelectric elements 138C, 138D and/or upper piezoelectric elements 138A, 138B. The detection of air in VARD 130 is not an error state per se, and purging of the air is possible as described below.

Figure 40:
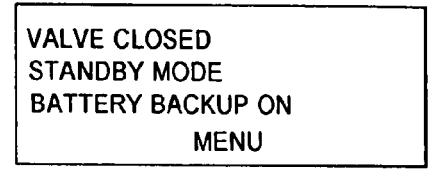
Figure 41:
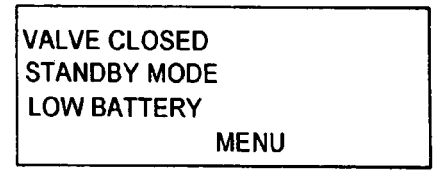
Figure 42:
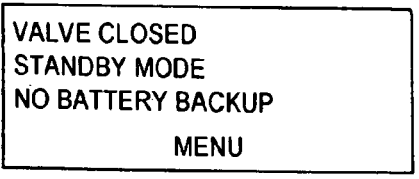

The power states are monitored, and one of the messages of FIGS. 40, 41, and 42 is displayed if the corresponding power state failure is detected, and the perfusionist can choose to ignore these error states.

Figure 39:
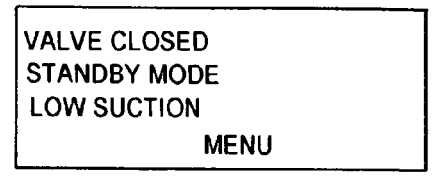

The error message of FIG. 39 may be displayed and the corresponding Caution light and sound emitted when suction is not sensed at suction port 414. In this way, the operability of the vacuum sensor or the connection of the vacuum sensor line 145 to the suction port 414 can be ascertained. However, the vacuum source is typically disconnected at this point so that further tests of the FIL sensor can be conducted as described below.

The displayed messages of FIGS. 37-42 also highlight the F2 key as "MENU" at the bottom of the LCD screen 430. The perfusionist can proceed to depress the F2 key from any of the displayed messages of FIGS. 20 and 37-42. If the perfusionist depresses the F2 key, the LCD screen 430 displays the message of FIG. 21 presenting three choices "LANG" (choose language) "SENSOR" (run FIL sensor test), and "RETURN" (go back to the FIG. 20 LCD screen display) for the keys F1, F2, and F3, respectively.

Figure 22:
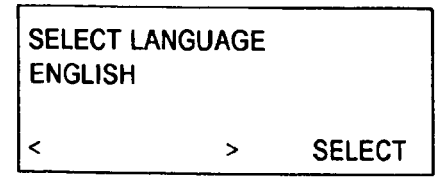
FIGS. 20-26 are LCD screen displays responsive to depression of certain keys by the perfusionist during the Standby Mode.

If the perfusionist depresses the F1 key, a choice of languages appears in the LCD screen display of FIG. 22 that the perfusionist can scroll through by repeatedly depressing the F1 or F2 key until the appropriate language is displayed, whereupon the perfusionist can then depress the F3 key to continue in the displayed language.

Figure 21:
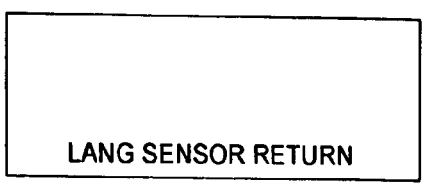
Figure 25:
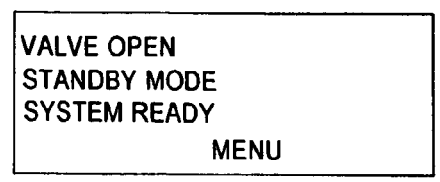
Figure 26:
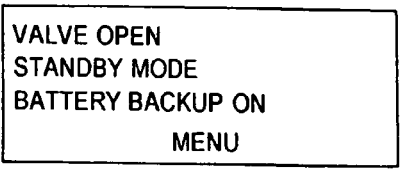
Figure 30:
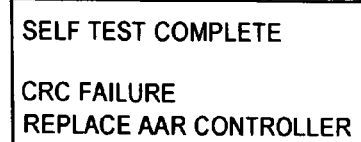
FIGS. 30-36 are LCD screen displays indicating error and system power states during the Self-Test Mode.

At this point, the perfusionist should test the operation of the FIL sensor 404 as indicated by the F2 key in the LCD screen display of FIG. 21. A test fluid tube in a diameter corresponding to the material and diameter specifications of the purge line segment 147 and that is empty of fluid can be temporarily placed passing through the FIL sensor 404. The perfusionist fits the tube into the FIL sensor 404, closes the sensor latch, and depresses the F2 key in the LCD screen display of FIG. 21 to initiate detection of the absence of fluid in the test tube, and the successful detection of air is indicated in the LCD screen display of FIG. 23.

It is also desirable to determine that the FIL sensor 404 can accurately detect fluid in the purge line segment 147 when it is placed to pass through it as shown in FIG. 14. So, the perfusionist depresses the F3 key designated "RETURN" to return to the LCD screen display of FIG. 20 and then depresses the F2 key to advance to the LCD screen display of FIG. 21. The perfusionist fills the test fluid tube with saline or water and places the fluid filled test tube passing through the FIL sensor 404. The FIL sensor latch is closed to apply uniform pressure against the fluid filled test tube, and the perfusionist again depresses the F2 key to conduct the test. The successful detection of fluid is indicated in the LCD screen display of FIG. 24, and the F3 key designated "RETURN" is then depressed to return to the LCD screen display of FIG. 20.

Figure 23:
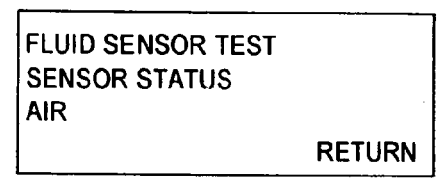
Figure 20:
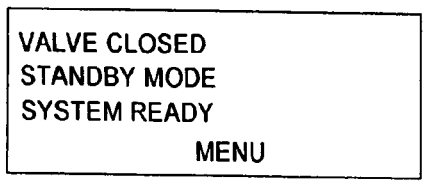
Figure 24:
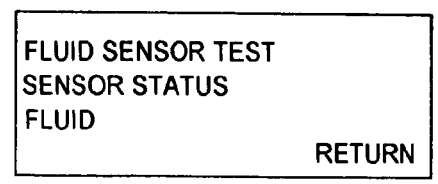

The AAR controller 400 is replaced by a backup unit and the process is restarted in step S100 if "AIR" or "FLUID" is inappropriately displayed in the messages of FIGS. 23 and 24, respectively, during the FIL sensor tests. The message of FIG. 20 is displayed on the LCD screen 430 upon successful completion of the FIL sensor tests. The disposable, integrated extracorporeal blood circuit 100 is then prepared for priming and primed as described above with respect to FIGS. 9-11 while the AAR controller 400 is in the Standby Mode.

The AAR system is employed in the concluding stages of priming as described above to complete the evacuation of air from the components and lines of the disposable, integrated extracorporeal blood circuit 100. The VARD stopcock 135 is opened (if not already open). The perfusionist opens the latch over the FIL sensor 404 and manually depresses the mechanical release button 412 to depress the pinch rod 458 downward. Portions of the purge line segment 147, partly filled with prime solution, are placed as shown in FIG. 14 fitted into the FIL sensor 404, the pinch valve 410, and the clip 426, with the vacuum sensor line 145 extending vertically. The perfusionist closes the latch over the FIL sensor 404 that applies uniform pressure to the portion of the purge line segment 147 trapped therein, and releases the mechanical release button 412 to allow the pinch rod 458 to rise upward and pinch the portion of the purge line segment 147 trapped therein.

The perfusionist attaches the free end of the vacuum sensor line 145 to the vacuum sensor input 414. The vacuum sensor line 145 is attached to the vacuum sensor input 414, and the purge line distal end connector 143 is coupled to a vacuum source, preferably through a vacuum line including a shut-off valve and the liquid trap. The shut-off valve is opened, the vacuum source regulator is adjusted to provide the specified vacuum (−225 mm Hg in this instance), and the error message of FIG. 39 should discontinue at this point.

Height adjustments are made to electronics arm assembly 314 along the mast 302 of FIG. 6 to ensure that the purge line segment 147 mounted at the top of the AAR controller 400 is at about the same height as the VARD purge port 134.

In this STANDBY state, the standby message of FIG. 20 will be normally displayed absent any detected errors. It would then be expected that the message of FIG. 38 is displayed and the corresponding Caution light and sound emitted when air is detected between the VARD air sensors. In the Standby Mode, the pinch valve 410 remains closed and is not automatically opened when air is sensed in the VARD 130. The perfusionist can selectively open the pinch valve 410 to purge air from the VARD 130 by depressing the MANUAL key (only if none of the power state failures are detected) or by depressing the mechanical release button 412 to depress the pinch rod 458 downward. The LCD screen 430 displays the message depicted in FIG. 25 when the MANUAL key is depressed and displays the message depicted in FIG. 26 when the mechanical release button 412 is depressed. The Caution light and sound are discontinued when air is no longer detected between the upper piezoelectric elements 138A, 138B.

After priming is completed, the operating algorithm remains in the Standby Mode, and the patient is prepared for cardioplegia and/or bypass as described above. The perfusionist can then depress the AUTO key to initiate the Automatic Mode of operation of the AAR controller 400 and VARD 130 during the delivery of cardioplegia and during bypass. As indicated in FIG. 16A, certain "transition" conditions are tested in step S124 when the AUTO key depression is detected in step S122. The transition error state messages that are detected in step S126 are displayed in step S128, and appropriate corrective action may have to be taken in step S130 before the Automatic Mode can be entered from step S126. The algorithm remains in the Standby Mode of step S114 after the corrective actions are taken in step S130 and ready to repeat the transition tests in step S124 upon subsequent depression of the AUTO key detected in step S122. The algorithm is restarted at step S100 with a replacement AAR controller 400 installed and connected as described above, if the AAR controller 400 must be replaced, and the Standby Mode of step S114 is again entered upon successful completion of steps S102-S112.

Figure 43:
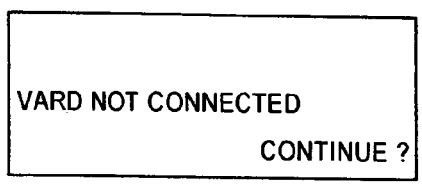

The VARD cable continuity is checked again in step S124, and the message of FIG. 43 is displayed on LCD screen 430 in step S128 if continuity is not found. The VARD cable 450 is either connected again or replaced and re-connected. The F3 key is depressed to return to step S114 and the AUTO key is depressed to again check for VARD continuity. If the error is repeated, the AAR controller 400 is to be replaced by a backup unit that is installed and connected as described above in step S100, and the Standby Mode of step S114 is again entered upon successful completion of steps S102-S112.

Figure 44:
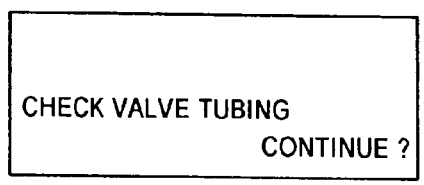

The presence or absence of a portion of the purge line segment 147 in the pinch valve 410 is determined in step S124 from the position of the pinch valve rod 458. A portion of the purge line segment 147 within the pinch valve opening prevents the pinch valve 458 from being urged all of the way across the pinch valve opening, and the position of the pinch rod 458 is detected by the optical sensors 472. The message of FIG. 44 is displayed on the LCD screen 430 in step S128 if the purge line segment 147 is not detected in this manner within the slot of the pinch valve 410. The perfusionist repositions the purge line segment 147 and depresses the F3 key to return to step S114. The AUTO key is again depressed to check for presence of the purge line segment 147. If the error is repeated, the AAR controller 400 is to be replaced by a backup unit that is installed and connected as described above in step S100, and the Standby Mode of step S114 is again entered upon successful completion of steps S102-S112.

Figure 45:
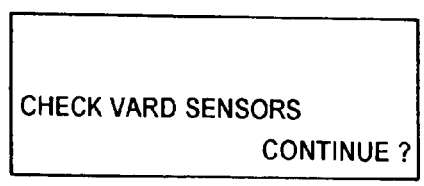

The AAR controller circuitry 460 also checks for any failure of the air sensor signal processing circuitry to properly respond to and interpret the air sensor output signal received from the receiver one of the piezoelectric elements 138A, 138B and 138C, 138D in step S124. It is expected that the AUTO key will be depressed when the VARD 130 is filled with fluid following priming, and therefore the air sensor output signal should not be indicative of air in the VARD 130. In step S124, the air sensor signal processing circuitry can be checked by a software test algorithm for accuracy in its response to the actual or true air sensor output signal and to a test air signal generated internally that is indicative of air in the VARD 130. The air sensor processing circuitry should not respond by providing a Caution or an Alarm based on the true air signal and should respond by providing a Caution or an Alarm in response to the test air signal. An erroneous response to the true air signal or the test air signal can be indicative of VARD cable failure or a failure of the air signal processing circuitry. The message of FIG. 45 is displayed on the LCD screen 430 in step S128 if an erroneous response is determined. The VARD cable 450 is either disconnected and connected again or replaced by a backup VARD cable 450. The F3 key is depressed to return to step S114 and the AUTO key is depressed to again check for air sensor signal circuitry or cable conductor integrity. If this error is repeated, the AAR controller 400 is to be replaced by a backup unit that is installed and connected as described above in step S100, and the Standby Mode of step S114 is again entered upon successful completion of steps S102-S112.

Figure 46:
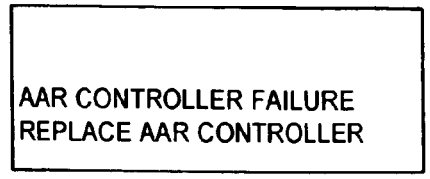
FIGS. 43-57 are LCD screen displays indicating error and system power states during the Automatic Mode.

In a further transition test, the output signals of the pinch valve optical sensors 472 are processed, and a logical conclusion is derived that the pinch rod 458 is in the proper closed position pressed against the portion of the purge line segment 147 within the pinch valve slot. The message of FIG. 46 is displayed on the LCD screen 430 if the pinch rod 458 is not detected in the proper closed position. The AAR controller 400 is to be replaced by a backup unit that is installed and connected as described above in step S100, and the Standby Mode of step S114 is again entered upon successful completion of steps S102-S112. The message of FIG. 44 is displayed if the pinch rod 458 is detected extending across the pinch valve slot, and the purge line segment 147 is to be repositioned within the pinch valve slot.

Figure 47:
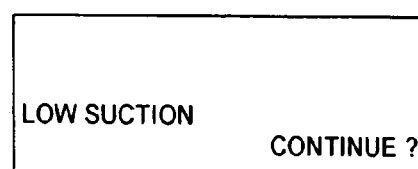

The vacuum or suction that is provided through the vacuum line connected to the purge line distal end connector 143 also continues to be checked in step S124 via vacuum sensor line 145 attached to the vacuum sensor input 414. The message of FIG. 47 is displayed on the LCD screen 430 in step S128 if the vacuum is low. The perfusionist is to take appropriate action in step S130 to adjust and independently test the vacuum through the vacuum sensor line 145, check the connection of the vacuum sensor line 145 to the vacuum sensor input 414, and depress the F3 key to return to the Standby Mode in step S114.

Figure 16B:
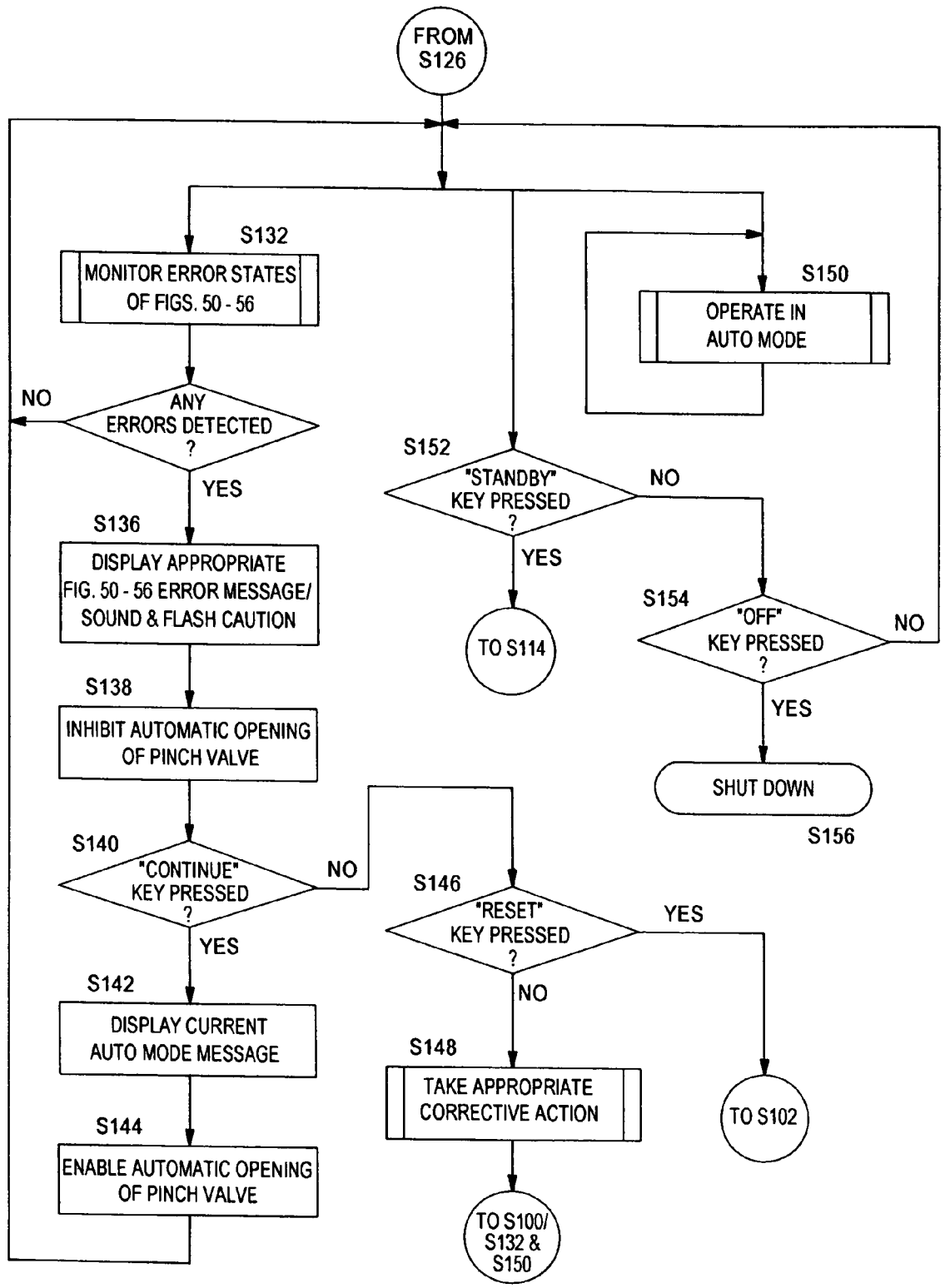
Figure 17A:
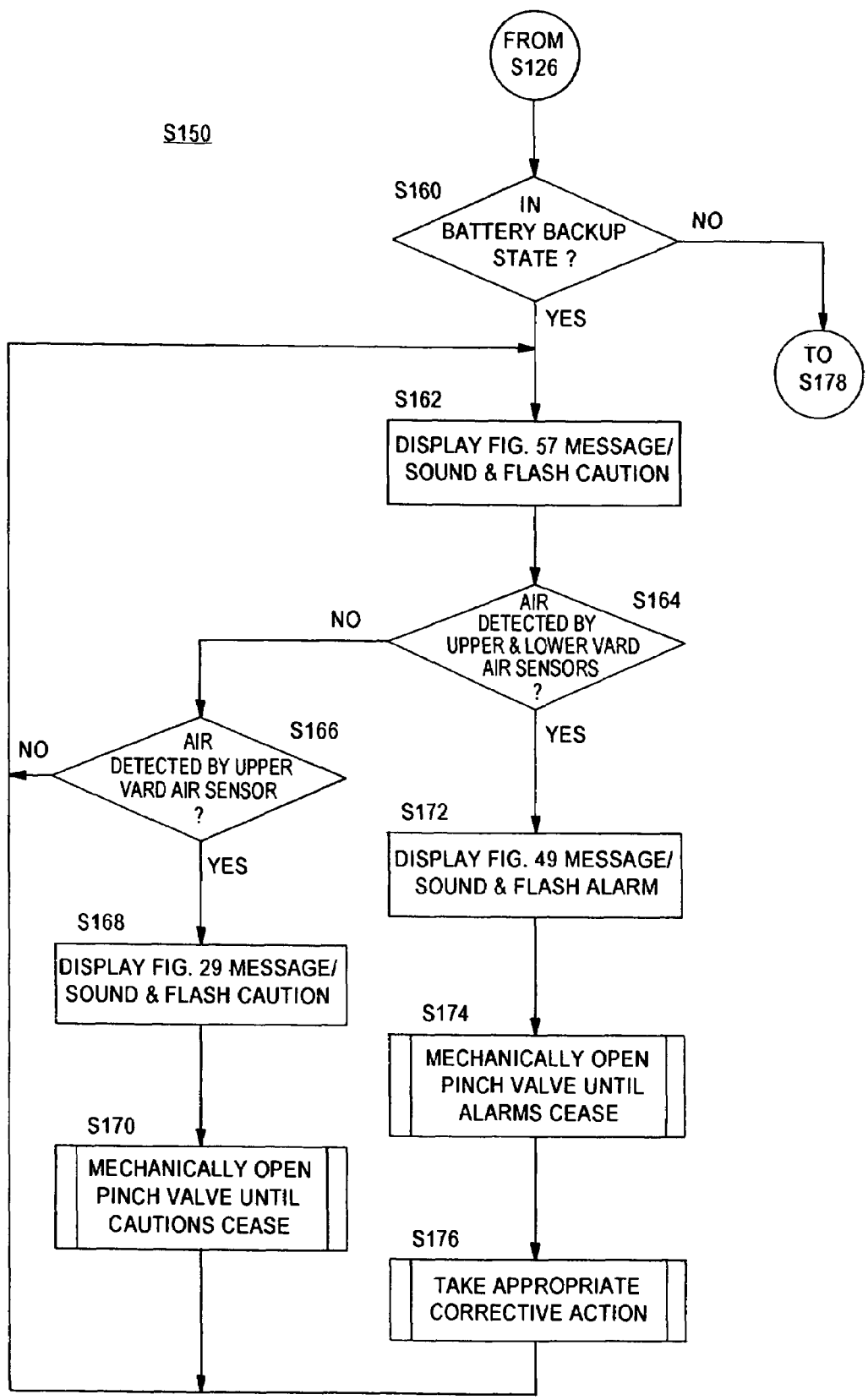
FIGS. 17A and 17B are a high level flow chart illustrating the steps of operation of the AAR system in the Automatic Mode.
Figure 17B:
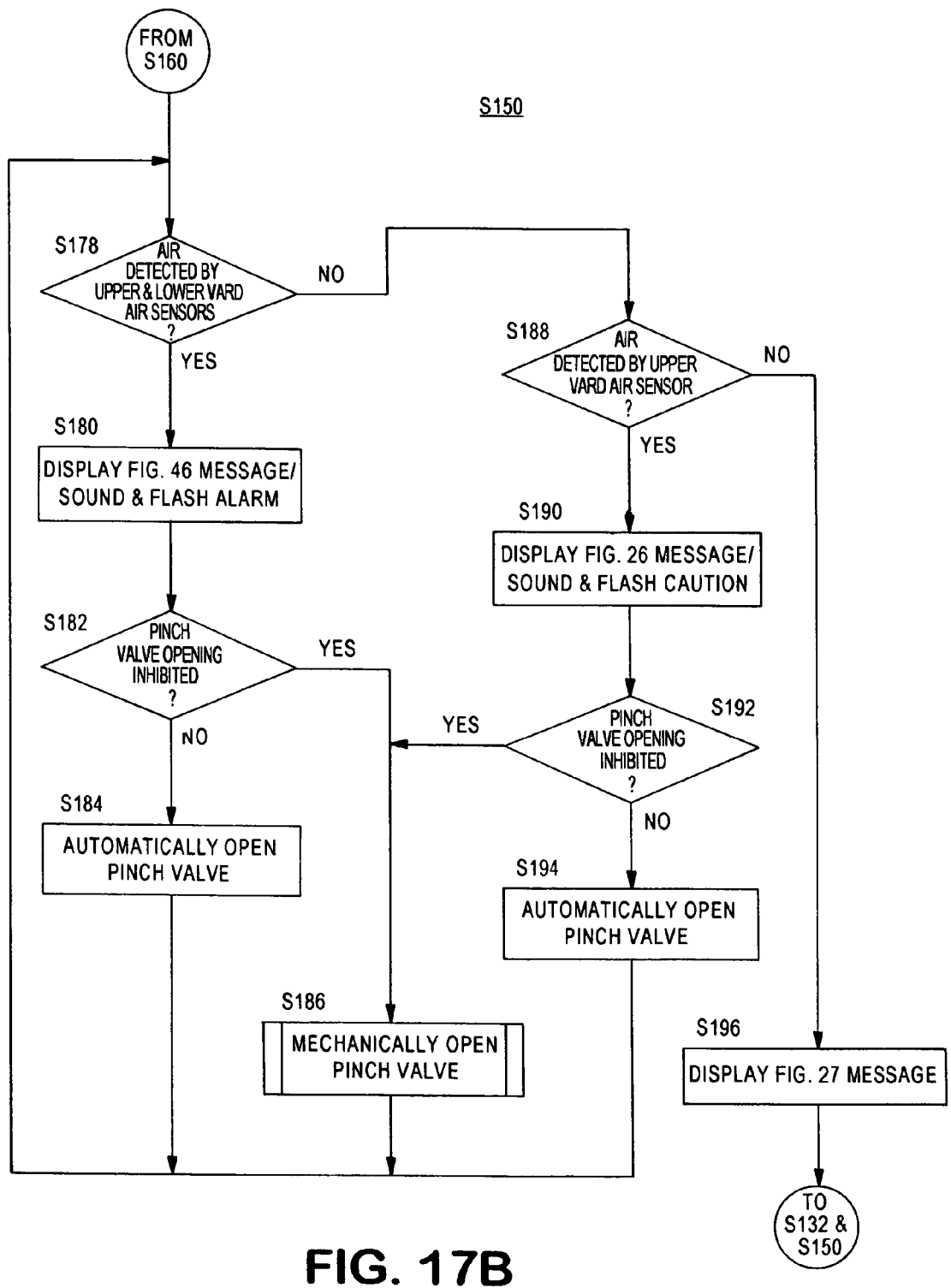

Turning first to FIG. 16B, the conditions that result in declaration of error states displayed by the error messages of FIGS. 50-56 are monitored in step S132 while the purging operations are conducted in step S150 as expanded in steps S160-S196 of FIGS. 17A and 17B. In FIG. 16B, the error monitoring and response operations and the actions taken by the perfusionist are depicted in parallel with the air purging operations since declared error states and actions of the perfusionist can interrupt or inhibit purging. The perfusionist can interrupt the Automatic Mode by depressing either the STANDBY key in step S152, returning to step S114 or the OFF key in step S154 shutting the AAR controller algorithm down in step S156.

Figure 27:
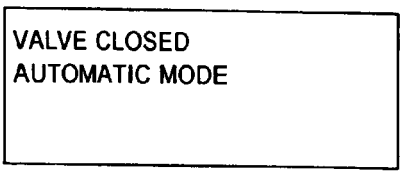
FIGS. 27 and 28 are LCD screen displays indicating the status of the purge valve during the Automatic Mode.
Figure 31:
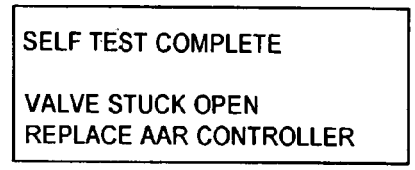

In FIG. 16B, the error messages shown in FIGS. 50-56 are displayed on LCD screen 430 in step S136 in place of the message of FIG. 27 when an error state is declared in step S134, and automatic opening of the pinch valve 410 is inhibited or interrupted in step S138. The error messages shown in FIGS. 50-52, and 54-56 result from the monitored conditions that cause the above-described error messages of FIGS. 31, 32, 45, 39, and 43, and similar corrective actions are to be taken in step S148. If no error states are declared in step S134, and no air is detected in the VARD 130, the operation in the Automatic Mode of step S150 results in display of the message of FIG. 27 by the LCD display screen 430 in step S196.

The error messages of FIGS. 50-54 and 56 offer the option to the perfusionist to continue operation by depressing the F3 key designated CONTINUE? to "clear" the error message if it is transitory. The depression of the F3 key is detected in step S140, and the current message generated in step S150 is displayed in step S142 and the automatic opening of the pinch valve 144 is enabled. However, steps S132 restarts, and the error state is again declared in step S134 if the underlying error condition is still present. Thus, the opening of the pinch valve 410 may only be transitory.

The perfusionist will then resort to either depressing the RESET key in step S146 to return to the Self Test Mode of step S102 or take the appropriate corrective action in step S148, which may involve replacing the AAR controller 400 and restarting the algorithm at step S100. Or the perfusionist may simply resort to manually opening the pinch valve by depressing the mechanical release button 412 or the MANUAL key or to manually clamping and unclamping the suction line or VARD purge line 141 as air is observed in the VARD 130 or venous return line.

The operations in step S150 of FIG. 16B, expanded upon as steps S160-S196 in FIGS. 17A-17B, depend upon whether the AAR circuitry 460 is being powered by the power supply 464 or is being powered by the backup battery 462, i.e., the operating system is in the battery backup state. In general, the operating system automatically opens the pinch valve 410 or responds to the MANUAL key depressed by the perfusionist when the operating system is powered by the power supply 464. The pinch valve 410 is closed or inhibited from opening when an error state is declared. However, the perfusionist is able to depress the mechanical release button 412 to push the pinch rod 458 down and open the pinch valve 410 at any time during the Automatic Mode to open the pinch valve 410.

The operating system will neither automatically open the pinch valve 410 nor respond to the MANUAL key depressed by the perfusionist if the operating system is in the battery backup state. Again, the perfusionist is able to depress the mechanical release button 412 to push the pinch rod 458 down and open the pinch valve 410. When air is sensed in VARD 130, the perfusionist is prompted to depress the mechanical release button 412, and the pinch valve 410 will remain open as long as the perfusionist continues to depress the mechanical release button 412. In practice, the perfusionist is expected to observe the air being purged through the distal purge line segment 147 and to release the mechanical release button 412 when blood is observed in purge line 141 or purge line segment 147.

Figure 48:
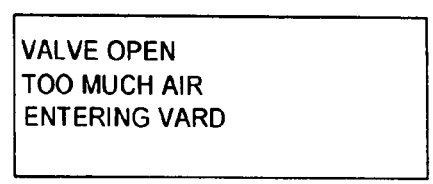

In addition, there are distinct AAR responses in the Automatic Mode to detection of air between the upper pair of piezoelectric elements 138A, 138B and the lower pair of piezoelectric elements 138C, 138D. Air detected between the lower pair of piezoelectric elements 138C, 138D indicates that too much air is entering the extracorporeal blood circuit 100 possibly from an air leak in the table lines or the cannulae extending into the venous and arterial vasculature of the patient. The error message "AIR IN VARD" of FIG. 48 is displayed by the LCD screen 430 if air is detected between the lower pair of piezoelectric elements 138C, 138D. The red Alarm LED flashes accompanied with the audible Alarm tone emitted by audible tone generator 416.

Figure 57:
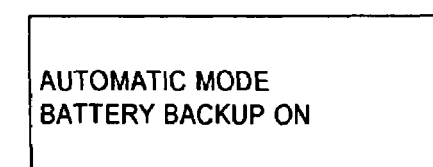

The operating power state is determined in step S160 of FIG. 17A, and the message of FIG. 57 is displayed in step S162 when the operating system is relying on the backup battery 462. The yellow Caution LED flashes accompanied with a single repeating, audible Caution tone emitted by audible tone generator 416. Thus, the message of FIG. 27 that would be typically displayed in the absence of air detected in the VARD 130 is not displayed on the LCD screen 430 if the operating system is relying on the backup battery 462.

Figure 29:
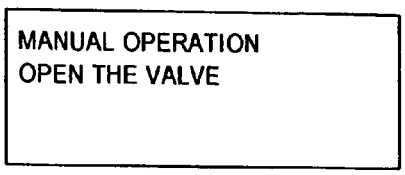
FIG. 29 is an LCD screen display instructing the perfusionist to mechanically open the pinch valve due to operation of the AAR controller in the battery backup state.
Figure 33:
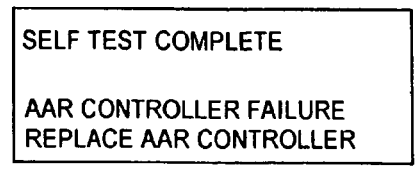

The message of FIG. 29 is displayed in step S168 when air is only detected between the upper piezoelectric elements 138A, 138B, as determined in steps S164 and S166. Again, the yellow Caution LED flashes accompanied with a single repeating, audible Caution tone emitted by audible tone generator 416. The perfusionist manually opens the pinch valve 410 in step S170 by depressing the mechanical release button 412 until the air is no longer detected between the upper piezoelectric elements 138A, 138B. The message of FIG. 57 is then displayed again on the LCD screen 430 in step S162 because the operating system continues to be powered by the backup battery 462.

Figure 49:
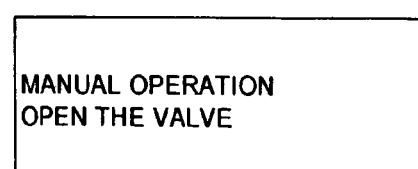
Figure 50:
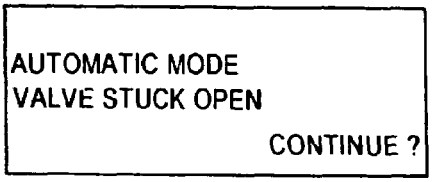
Figure 54:
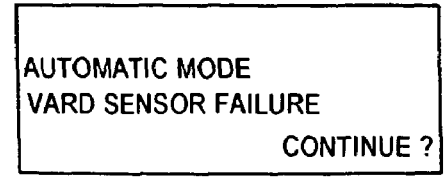
Figure 51:
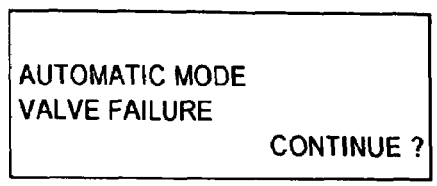
Figure 55:
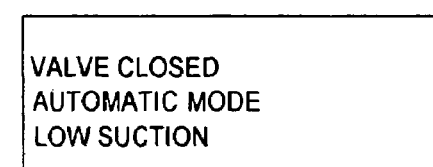
Figure 52:
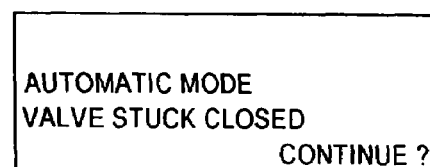
Figure 56:
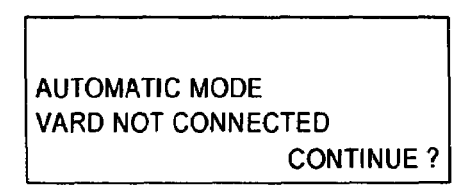

The message shown in FIG. 49 is displayed and the Alarm sound and red light are emitted in step S172 if air is detected between the lower piezoelectric elements 138C, 138D and between the upper piezoelectric elements 138A, 138B. The perfusionist manually opens the pinch valve 410 in step S174 by depressing the mechanical release button 412 until the air is no longer detected between the lower piezoelectric elements 138C, 138D. The perfusionist also takes appropriate corrective actions in step S178 to locate and stem air suction into the extracorporeal blood circuit 100 or in the table lines and cannulae and may also slow the speed of the blood pump 150.

The message of FIG. 29 is then displayed in step S168 when air is only detected between the upper piezoelectric elements 138A, 138B, as determined in steps S164 and S166. Again, the yellow Caution LED flashes accompanied with a single repeating, audible Caution tone emitted by audible tone generator 416. The perfusionist continues to manually open the pinch valve 410 in step S174 by depressing the mechanical release button 412 until the air is no longer detected between the lower piezoelectric elements 138C, 138D, and the message of FIG. 57 is again displayed on the LCD screen 430 in step S142 because the operating system continues to be powered by the backup battery 462.

The automatic application of power to the solenoid to lower the pinch rod 458 to automatically open the pinch valve 410 can take place in step S184 or step S194 when the determination is made in steps S160 that the AAR operating system is powered by the power supply 464 and no error states are declared in step S134 as confirmed in steps S182 and S192, respectively.

Figure 28:
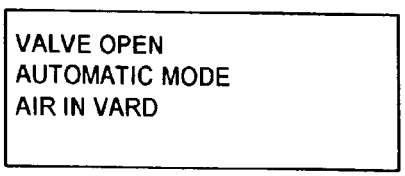
Figure 32:
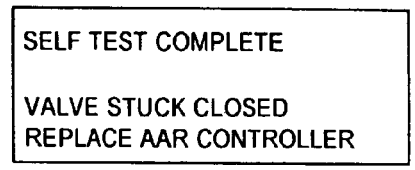

In the absence of a declared error state, the message shown in FIG. 28 is displayed on the LCD screen 430 and the yellow Caution LED flashes accompanied by a Caution tone emitted by audible tone generator 416 in step S190 if air is detected between the upper piezoelectric elements 138A, 138B in step S188 and is not detected between the lower piezoelectric elements 138C, 138D in step S178. The pinch valve 410 is automatically opened in step S194, and air is purged through the VARD purge line 141 until air is no longer detected between the upper piezoelectric elements 138A, 138B in step S188. The message shown in FIG. 27 is displayed in step S196 when air is no longer detected between the upper piezoelectric elements 138A, 138B.

Similarly, in the absence of a declared error state, the message shown in FIG. 48 is displayed on the LCD screen 430 and the red Alarm LED flashes accompanied with an Alarm sound emitted by audible tone generator 416 in step S180 if air is detected between the upper piezoelectric elements 138A, 138B and the lower piezoelectric elements 138C, 138D in step S178. The pinch valve 410 is automatically opened in step S184, and air is purged through the VARD purge line 141 until air is no longer detected between the lower piezoelectric elements 138C, 138D in step S178. The perfusionist also takes appropriate corrective actions in step S178 to locate and stem air suction into the extracorporeal blood circuit 100 or in the table lines and cannulae and may also slow the speed of the blood pump 150. It should be noted that the speed of the blood pump 150 may be automatically lowered if air is detected between the upper piezoelectric elements 138A, 138B and the lower piezoelectric elements 138C, 138D in step S178.

Then, air is detected between the upper piezoelectric elements 138A, 138B in step S188, the message shown in FIG. 28 is displayed on the LCD screen 430 and the yellow Caution LED flashes accompanied by a Caution tone emitted by audible tone generator 416 in step S190. The pinch valve 410 remains automatically opened in step S194, and air is purged through the VARD purge line 141 until air is no longer detected between the upper piezoelectric elements 138A, 138B in step S188. The message shown in FIG. 27 is displayed in step S196 when air is no longer detected between the upper piezoelectric elements 138A, 138B.

In this way, air is purged automatically in step S184 or S194 as long as no error state is declared in step S134 of FIG. 16B resulting in the error messages of FIGS. 50-56 that inhibit opening of the pinch valve as determined in steps S182 and S192, respectively. If an error state is declared in step S134, the perfusionist may choose to manually open the pinch valve 410 by depressing the mechanical release button 412 or the MANUAL key in step S186. Other appropriate corrective action is to be taken in accordance with steps S146 and S148 of FIG. 16B. Thus, the AAR system of the present invention can be employed in manual and automatic operating modes to reliably detect air in the VARD 130 and remove it.

The various sensors and error condition monitors of the AAR operating system function independently and in parallel operations. It will be understood that the steps of the operating algorithm performed by the AAR operating system depicted in FIGS. 16A-16B and 17A-17B are merely exemplary and that they can be performed in somewhat different order.

CONCLUSION

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical performance of a cardiac bypass procedure that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

We claim:

1. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:
    an air removal device incorporated in the extracorporeal blood circuit, the air removal device comprising:
        an air removal device housing enclosing a chamber;
        an air removal device purge port through the housing to the chamber;
        an air sensor supported by the air removal device housing in relation to the chamber adapted to provide an air sensor signal indicative of the presence of fluid or air in the air removal device housing;
    an air removal device purge line coupled to the air removal device purge port and extending to a purge line connector adapted to be coupled to a vacuum source to apply suction to the air removal device purge port to draw air therefrom;

an AAR controller having a purge valve adapted to receive a portion of the purge line and AAR controller circuitry to open or close the purge line, the AAR controller circuitry further comprising:

purge valve operating means for opening the purge valve in response to an air sensor signal indicative of the presence of air in the air removal device housing to allow air sensed in the air removal device to be purged through the purge line by the suction of the vacuum source;

error state determining means for monitoring operations and conditions of the AAR system and determining an error state of the AAR system;

alerting means for alerting the perfusionist of the error state; and further wherein the AAR controller further comprises a mechanical release button interconnected with the purge valve adapted to enable manual opening of the purge valve by the perfusionist.

2. The AAR system of claim 1, wherein:
the AAR controller further comprises a backup battery for providing operating power to the AAR controller circuitry;
the error state determining means determines if the backup battery is providing adequate operating power; and
the alerting means issues a backup battery error alert if the backup battery is not providing adequate operating power.

3. The AAR system of claim 1, wherein:
the alerting means formulates alert message signals; and
the AAR controller further comprises a display screen that the alert messages are applied to for displaying messages readable by the perfusionist.

4. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:

an air removal device incorporated in the extracorporeal blood circuit, the air removal device comprising:
an air removal device housing enclosing a chamber;
an air removal device purge port through the housing to the chamber;
an air sensor supported by the air removal device housing in relation to the chamber adapted to provide an air sensor signal indicative of the presence of fluid or air in the air removal device housing;

an air removal device purge line coupled to the air removal device purge port and extending to a purge line connector adapted to be coupled to a vacuum source to apply suction to the air removal device purge port to draw air therefrom;

an AAR controller having a purge valve adapted to receive a portion of the purge line and AAR controller circuitry to open or close the purge line, the AAR controller circuitry further comprising:

purge valve operating means for opening the purge valve in response to an air sensor signal indicative of the presence of air in the air removal device housing to allow air sensed in the air removal device to be purged through the purge line by the suction of the vacuum source;

error state determining means for monitoring operations and conditions of the AAR system and determining an error state of the AAR system;

alerting means for alerting the perfusionist of the error state;

wherein: the AAR controller further comprises a fluid in line (FIL) sensor arranged with respect to the purge valve adapted to receive a portion of the purge line to provide a FIL sensor signal to the AAR controller circuitry;

the error determining means determines if the FIL sensor signal indicates the presence of fluid in the purge line;

the alerting means issues an alert that fluid is present in the purge line when the error determining means determines that the FIL sensor signal indicates the presence of fluid in the purge line;

wherein the purge valve operating means is inhibited from opening the purge valve in response the air sensor signal indicative of the presence of air in the air removal device housing when the FIL sensor signal is determined to be indicative of fluid in the purge line; and wherein the AAR controller further comprises a mechanical release button interconnected with the purge valve adapted to enable manual opening of the purge valve by the perfusionist when the purge valve is closed in response to the FIL sensor signal indicative of fluid in the purge line.

5. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:

an air removal device incorporated in the extracorporeal blood circuit, the air removal device comprising:
an air removal device housing enclosing a chamber;
an air removal device purge port through the housing to the chamber;
an air sensor supported by the air removal device housing in relation to the chamber adapted to provide an air sensor signal indicative of the presence of fluid or air in the air removal device housing;

an air removal device purge line coupled to the air removal device purge port and extending to a purge line connector adapted to be coupled to a vacuum source to apply suction to the air removal device purge port to draw air therefrom;

an AAR controller having a purge valve adapted to receive a portion of the purge line and AAR controller circuitry to open or close the purge line, the AAR controller circuitry further comprising:

purge valve operating means for opening the purge valve in response to an air sensor signal indicative of the presence of air in the air removal device housing to allow air sensed in the air removal device to be purged through the purge line by the suction of the vacuum source;

error state determining means for monitoring operations and conditions of the AAR system and determining an error state of the AAR system;

alerting means for alerting the perfusionist of the error state; and wherein: the AAR controller further comprises a vacuum sensor arranged with respect to the purge line to provide a vacuum signal to the AAR controller circuitry indicative of vacuum in the purge line;

the error state determining means determines if the sensed vacuum exceeds a minimum vacuum; and the alerting means issues an alert if the sensed vacuum does not exceed the minimum vacuum.

6. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:

an air removal device incorporated in the extracorporeal blood circuit, the air removal device comprising:
an air removal device housing enclosing a chamber;
an air removal device purge port through the housing to the chamber;
an air sensor supported by the air removal device housing in relation to the chamber adapted to provide an air sensor signal indicative of the presence of fluid or air in the air removal device housing;
an air removal device purge line coupled to the air removal device purge port and extending to a purge line connector adapted to be coupled to a vacuum source to apply suction to the air removal device purge port to draw air therefrom;
an AAR controller having a purge valve adapted to receive a portion of the purge line and AAR controller circuitry to open or close the purge line, the AAR controller circuitry further comprising:
purge valve operating means for opening the purge valve in response to an air sensor signal indicative of the presence of air in the air removal device housing to allow air sensed in the air removal device to be purged through the purge line by the suction of the vacuum source;
error state determining means for monitoring operations and conditions of the AAR system and determining an error state of the AAR system;
alerting means for alerting the perfusionist of the error state; and
wherein: the AAR controller has an air sensor cable connector;
an air removal device cable extends from the air sensor to a cable terminal coupled to the air sensor cable connector;
the error state determining means comprises an electrical continuity checking circuit of the AAR controller circuitry coupled to the air sensor cable connector that provides a continuity signal indicative of continuity of the connection of the air removal device cable between the air sensor and the air sensor cable connector; and
the alerting means issues an air removal device cable error alert if the continuity signal is not provided.

7. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:

an air removal device incorporated in the extracorporeal blood circuit, the air removal device comprising:
an air removal device housing enclosing a chamber;
an air removal device purge port through the housing to the chamber;
an air sensor supported by the air removal device housing in relation to the chamber adapted to provide an air sensor signal indicative of the presence of fluid or air in the air removal device housing;
an air removal device purge line coupled to the air removal device purge port and extending to a purge line connector adapted to be coupled to a vacuum source to apply suction to the air removal device purge port to draw air therefrom;
an AAR controller having a purge valve adapted to receive a portion of the purge line and AAR controller circuitry to open or close the purge line, the AAR controller circuitry further comprising:
purge valve operating means for opening the purge valve in response to an air sensor signal indicative of the presence of air in the air removal device housing to allow air sensed in the air removal device to be purged through the purge line by the suction of the vacuum source;
error state determining means for monitoring operations and conditions of the AAR system and determining an error state of the AAR system;
alerting means for alerting the perfusionist of the error state;
wherein: the purge valve comprises a pinch valve having a valve slot receiving the portion of the purge line and a pinch rod adapted to be moved between a purge valve closed position extending into the slot to compress the purge line and a purge valve open position retracted out of the slot;
the purge valve operating means is coupled to the pinch rod to move the pinch rod between the purge valve closed position and the purge valve open position; and
wherein: the error state determining means comprises:
at least one pinch rod position sensor providing a pinch rod position signal indicative of the actual position of the pinch rod; and
means responsive to the pinch rod position signal for determining a position error state of the purge valve or the purge valve operating means when the pinch rod position signal does not confirm that the pinch rod is in a purge valve open position or a purge valve closed position dictated by the purge valve operating means; and
the alerting means issues a pinch rod position error alert in responsive to the determined position error state.

8. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:

an air removal device incorporated in the extracorporeal blood circuit, the air removal device comprising:
an air removal device housing enclosing a chamber;
an air removal device purge port through the housing to the chamber;
an air sensor supported by the air removal device housing in relation to the chamber adapted to provide an air sensor signal indicative of the presence of fluid or air in the air removal device housing;
an air removal device purge line coupled to the air removal device purge port and extending to a purge line connector adapted to be coupled to a vacuum source to apply suction to the air removal device purge port to draw air therefrom;
an AAR controller having a purge valve adapted to receive a portion of the purge line and AAR controller circuitry to open or close the purge line, the AAR controller circuitry further comprising:

purge valve operating means for opening the purge valve in response to an air sensor signal indicative of the presence of air in the air removal device housing to allow air sensed in the air removal device to be purged through the purge line by the suction of the vacuum source;

error state determining means for monitoring operations and conditions of the AAR system and determining an error state of the AAR system;

alerting means for alerting the perfusionist of the error state; and wherein: the error state determining means comprises:
at least one purge valve state sensor providing a purge state signal indicative of the actual open or closed state of the purge valve;

means responsive to the purge valve state signal for determining an error state of the purge valve or the purge valve operating means when the purge valve state signal does not confirm that the purge valve is in a commanded one of the purge valve open position and the purge valve closed position dictated by the purge valve operating means; and the alerting means issues a purge valve error alert in responsive to the determined position error state.

9. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:

an air removal device incorporated in the extracorporeal blood circuit, the air removal device comprising:
an air removal device housing enclosing a chamber;
an air removal device purge port through the housing to the chamber;
an air sensor supported by the air removal device housing in relation to the chamber adapted to provide an air sensor signal indicative of the presence of fluid or air in the air removal device housing;

an air removal device purge line coupled to the air removal device purge port and extending to a purge line connector adapted to be coupled to a vacuum source to apply suction to the air removal device purge port to draw air therefrom;

an AAR controller having a purge valve adapted to receive a portion of the purge line and AAR controller circuitry to open or close the purge line, the AAR controller circuitry further comprising:

purge valve operating means for opening the purge valve in response to an air sensor signal indicative of the presence of air in the air removal device housing to allow air sensed in the air removal device to be purged through the purge line by the suction of the vacuum source;

error state determining means for monitoring operations and conditions of the AAR system and determining an error state of the AAR system;

alerting means for alerting the perfusionist of the error state; and wherein:
the AAR controller further comprises a power supply adapted to be coupled to electrical mains power for providing operating power to the AAR controller circuitry and purge valve operating means;

the error state determining means determines if the power supply is providing adequate operating power; and the alerting means issues a power supply error alert if the power supply is not providing adequate operating power.

10. The AAR system of claim 9, wherein the power supply comprises redundant power supply circuits and means for selecting an operable power supply circuit.

11. The AAR system of claim 10, wherein:
the AAR controller further comprises a backup battery for providing operating power to the AAR controller circuitry;

the error state determining means determines if the backup battery is providing adequate operating power; and the alerting means issues a backup battery error alert if the backup battery is not providing adequate operating power.

12. The AAR system of claim 9, wherein:
the AAR controller further comprises a backup battery for providing operating power to the AAR controller circuitry; and the AAR controller circuitry is powered by the backup battery when the error state determining means determines that the power supply is not providing adequate operating power.

13. The AAR system of claim 12, wherein:
the purge valve operating means is disabled when the AAR controller circuitry is powered by the backup battery; and the AAR controller further comprises a mechanical release button interconnected with the purge valve adapted to enable manual opening of the purge valve by the perfusionist.

14. The AAR system of claim 12, wherein the alerting means issues a backup battery alert if the AAR controller circuitry is powered by the backup battery.

15. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:

an air removal device incorporated in the extracorporeal blood circuit, the air removal device comprising:
an air removal device housing enclosing a chamber;
an air removal device purge port through the housing to the chamber;
an air sensor supported by the air removal device housing in relation to the chamber adapted to provide an air sensor signal indicative of the presence of fluid or air in the air removal device housing;

an air removal device purge line coupled to the air removal device purge port and extending to a purge line connector adapted to be coupled to a vacuum source to apply suction to the air removal device purge port to draw air therefrom;

an AAR controller having a purge valve adapted to receive a portion of the purge line and AAR controller circuitry to open or close the purge line, the AAR controller circuitry further comprising:

purge valve operating means for opening the purge valve in response to an air sensor signal indicative of the presence of air in the air removal device housing to allow air sensed in the air removal device to be purged through the purge line by the suction of the vacuum source;

error state determining means for monitoring operations and conditions of the AAR system and determining an error state of the AAR system;
alerting means for alerting the perfusionist of the error state; and
wherein:
the alerting means formulates alert sound signals; and
the AAR controller further comprises at least one sound emitter that emits audible alert sounds in response to the alert sound signals that can be heard by the perfusionist.

16. An active air removal (AAR) system for purging air from an integrated extracorporeal blood circuit providing extracorporeal oxygenation of a patient's blood during cardiopulmonary bypass surgery adapted to be performed on a patient in the presence of a perfusionist, the AAR system comprising:
an air removal device incorporated in the extracorporeal blood circuit, the air removal device comprising:
an air removal device housing enclosing a chamber;
an air removal device purge port through the housing to the chamber;
an air sensor supported by the air removal device housing in relation to the chamber adapted to provide an air sensor signal indicative of the presence of fluid or air in the air removal device housing;
an air removal device purge line coupled to the air removal device purge port and extending to a purge line connector adapted to be coupled to a vacuum source to apply suction to the air removal device purge port to draw air therefrom;
an AAR controller having a purge valve adapted to receive a portion of the purge line and AAR controller circuitry to open or close the purge line, the AAR controller circuitry further comprising:
purge valve operating means for opening the purge valve in response to an air sensor signal indicative of the presence of air in the air removal device housing to allow air sensed in the air removal device to be purged through the purge line by the suction of the vacuum source;
error state determining means for monitoring operations and conditions of the AAR system and determining an error state of the AAR system;
alerting means for alerting the perfusionist of the error state; and
wherein: the alerting means formulates alert light signals; and
the AAR controller further comprises at least one light emitter that emits visual light in response to the alert light signals that can be seen by the perfusionist.

17. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:
providing an air removal device incorporated in the extracorporeal blood circuit, the air removal device comprising:
an air removal device housing enclosing a chamber;
an air removal device purge port through the housing to the chamber;
an air sensor supported by the air removal device housing; and
an air removal device purge line coupled to the air removal device purge port extending to a purge line connector adapted to be coupled to a vacuum source to apply suction to the air removal device purge port to draw air therefrom;
locating a portion of the air removal purge line extending through a purge valve of an AAR controller, the purge valve movable between a purge valve open position and a purge valve closed position;
applying operating power to the air sensor to generate an air sensor signal indicative of the absence or presence of air in the air removal device housing;
opening the puree valve in response to an air sensor signal indicative of the presence of air in the air removal device housing to allow air sensed in the air removal device to be purged through the purge line by the suction of the vacuum source;
monitoring operations or conditions of the AAR system;
determining an error state of the monitored operations or conditions of the AAR system;
issuing an alert to alert the perfusionist of the error state; and
further wherein the AAR controller further comprises a mechanical release button interconnected with the purge valve adapted to enable manual opening of the purge valve by the perfusionist.

18. The purging method of claim 17, wherein:
the AAR controller further comprises AAR controller circuitry and a backup battery for providing operating power to the AAR controller circuitry;
the determining step comprises determining if the backup battery is providing adequate operating power; and
the alert issuing step comprises issuing a backup battery error alert if the backup battery is not providing adequate operating power.

19. The purging method of claim 17, wherein:
the AAR controller further comprises a backup battery for providing operating power to the AAR controller circuitry;
the determining step comprises determining if the backup battery is providing adequate operating power; and
the alert issuing step comprises issuing a backup battery error alert if the backup battery is not providing adequate operating power.

20. The purging method of claim 17, wherein the alert issuing step comprises:
formulating alert message signals related to the determined error state; and
displaying alert messages readable by the perfusionist on a display screen.

21. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:
providing an air removal device incorporated in the extracorporeal blood circuit, the air removal device comprising:
an air removal device housing enclosing a chamber;
an air removal device purge port through the housing to the chamber;
an air sensor supported by the air removal device housing; and
an air removal device purge line coupled to the air removal device purge port extending to a purge line connector adapted to be coupled to a vacuum source to apply suction to the air removal device purge port to draw air therefrom;

locating a portion of the air removal purge line extending through a purge valve of an AAR controller, the purge valve movable between a purge valve open position and a purge valve closed position;
applying operating power to the air sensor to generate an air sensor signal indicative of the absence or presence of air in the air removal device housing;
opening the purge valve in response to an air sensor signal indicative of the presence of air in the air removal device housing to allow air sensed in the air removal device to be purged through the purge line by the suction of the vacuum source;
monitoring operations or conditions of the AAR system;
determining an error state of the monitored operations or conditions of the AAR system;
issuing an alert to alert the perfusionist of the error state; and
wherein the AAR controller further comprises a fluid in line (FIL) sensor arranged with respect to the purge valve, and further comprising:
locating a further portion of the purge line through the FIL sensor; and
powering the FIL sensor to develop a FIL sensor signal indicative of the absence or presence of fluid in the purge line, and wherein:
the error state determining step comprises determining if the FIL sensor signal indicates the presence of fluid in the purge line.

22. The purging method of claim 21, further comprising inhibiting the opening of the purge valve when the FIL sensor signal is determined to be indicative of fluid in the purge line.

23. The purging method of claim 22, wherein the AAR controller further comprises a mechanical release button interconnected with the purge valve adapted to enable manual opening of the purge valve by the perfusionist.

24. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:
providing an air removal device incorporated in the extracorporeal blood circuit, the air removal device comprising:
an air removal device housing enclosing a chamber;
an air removal device purge port through the housing to the chamber;
an air sensor supported by the air removal device housing; and
an air removal device purge line coupled to the air removal device purge port extending to a purge line connector adapted to be coupled to a vacuum source to apply suction to the air removal device purge port to draw air therefrom;
locating a portion of the air removal purge line extending through a purge valve of an AAR controller, the purge valve movable between a purge valve open position and a purge valve closed position;
applying operating power to the air sensor to generate an air sensor signal indicative of the absence or presence of air in the air removal device housing;
opening the purge valve in response to an air sensor signal indicative of the presence of air in the air removal device housing to allow air sensed in the air removal device to be purged through the purge line by the suction of the vacuum source;
monitoring operations or conditions of the AAR system;
determining an error state of the monitored operations or conditions of the AAR system;
issuing an alert to alert the perfusionist of the error state; and
wherein:
the AAR controller further comprises a vacuum sensor arranged with respect to the purge line to provide a vacuum signal indicative of vacuum in the purge line;
the error state determining step determines if the sensed vacuum exceeds a minimum vacuum; and
the alert issuing step issues an alert if the sensed vacuum does not exceed the minimum vacuum.

25. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:
providing an air removal device incorporated in the extracorporeal blood circuit, the air removal device comprising:
an air removal device housing enclosing a chamber;
an air removal device purge port through the housing to the chamber;
an air sensor supported by the air removal device housing; and
an air removal device purge line coupled to the air removal device purge port extending to a purge line connector adapted to be coupled to a vacuum source to apply suction to the air removal device purge port to draw air therefrom;
locating a portion of the air removal purge line extending through a purge valve of an AAR controller, the purge valve movable between a purge valve open position and a purge valve closed position;
applying operating power to the air sensor to generate an air sensor signal indicative of the absence or presence of air in the air removal device housing;
opening the purge valve in response to an air sensor signal indicative of the presence of air in the air removal device housing to allow air sensed in the air removal device to be purged through the purge line by the suction of the vacuum source;
monitoring operations or conditions of the AAR system;
determining an error state of the monitored operations or conditions of the AAR system;
issuing an alert to alert the perfusionist of the error state; and
further comprising:
connecting an air sensor cable between the AAR controller and the air sensor; and
wherein:
the determining step determines if electrical continuity is present in the connection of the air sensor cable between the AAR controller and the air sensor; and
the alert issuing step issues an air removal device cable error alert if electrical continuity is not determined.

26. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:
providing an air removal device incorporated in the extracorporeal blood circuit, the air removal device comprising:

an air removal device housing enclosing a chamber;
an air removal device purge port through the housing to the chamber;
an air sensor supported by the air removal device housing; and
an air removal device purge line coupled to the air removal device purge port extending to a purge line connector adapted to be coupled to a vacuum source to apply suction to the air removal device purge port to draw air therefrom;

locating a portion of the air removal purge line extending through a purge valve of an AAR controller, the purge valve movable between a purge valve open position and a purge valve closed position;

applying operating power to the air sensor to generate an air sensor signal indicative of the absence or presence of air in the air removal device housing;

opening the purge valve in response to an air sensor signal indicative of the presence of air in the air removal device housing to allow air sensed in the air removal device to be purged through the purge line by the suction of the vacuum source;

monitoring operations or conditions of the AAR system;

determining an error state of the monitored operations or conditions of the AAR system;

issuing an alert to alert the perfusionist of the error state;

wherein the purge valve comprises a pinch valve having a valve slot receiving the portion of the purge line and a pinch rod adapted to be moved between a purge valve closed position extending into the slot to compress the purge line and a purge valve open position retracted out of the slot;

the purge valve opening step comprises moving the pinch rod from the purge valve closed position to the purge valve open position and wherein:

the error state determining step comprises:
commanding the pinch rod to move into one of the pinch valve open and closed positions;
sensing the pinch rod position and providing a pinch rod position signal indicative of the actual position of the pinch rod; and
determining a position error state of the purge valve when the pinch rod position signal does not confirm that the pinch rod is in the commanded purge valve open or purge valve closed position; and the alert issuing step comprises issuing a pinch rod position error alert in response to the determined position error state.

27. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:

providing an air removal device incorporated in the extracorporeal blood circuit, the air removal device comprising:
an air removal device housing enclosing a chamber;
an air removal device purge port through the housing to the chamber;
an air sensor supported by the air removal device housing; and
an air removal device purge line coupled to the air removal device purge port extending to a purge line connector adapted to be coupled to a vacuum source to apply suction to the air removal device purge port to draw air therefrom;

locating a portion of the air removal purge line extending through a purge valve of an AAR controller, the purge valve movable between a purge valve open position and a purge valve closed position;

applying operating power to the air sensor to generate an air sensor signal indicative of the absence or presence of air in the air removal device housing;

opening the purge valve in response to an air sensor signal indicative of the presence of air in the air removal device housing to allow air sensed in the air removal device to be purged through the purge line by the suction of the vacuum source;

monitoring operations or conditions of the AAR system;

determining an error state of the monitored operations or conditions of the AAR system;

issuing an alert to alert the perfusionist of the error state; and wherein:

the error state determining step comprises:
commanding the purge valve to move into one of the purge valve open and closed positions;
sensing the purge valve position and providing a purge valve position signal indicative of the actual position of the purge valve; and
determining a position error state of the purge valve or the purge valve operating means when the sensed purge valve position signal does not confirm that the purge valve is in the commanded purge valve open position or purge valve closed position; and the alert issuing step comprises issuing a purge valve error alert in responsive to the determined position error state.

28. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:

providing an air removal device incorporated in the extracorporeal blood circuit, the air removal device comprising:
an air removal device housing enclosing a chamber;
an air removal device purge port through the housing to the chamber;
an air sensor supported by the air removal device housing; and
an air removal device purge line coupled to the air removal device purge port extending to a purge line connector adapted to be coupled to a vacuum source to apply suction to the air removal device purge port to draw air therefrom;

locating a portion of the air removal purge line extending through a purge valve of an AAR controller, the purge valve movable between a purge valve open position and a purge valve closed position;

applying operating power to the air sensor to generate an air sensor signal indicative of the absence or presence of air in the air removal device housing;

opening the purge valve in response to an air sensor signal indicative of the presence of air in the air removal device housing to allow air sensed in the air removal device to be purged through the purge line by the suction of the vacuum source;

monitoring operations or conditions of the AAR system;

determining an error state of the monitored operations or conditions of the AAR system;

issuing an alert to alert the perfusionist of the error state; and wherein:

the AAR controller further comprises AAR controller circuitry and a power supply adapted to be coupled to electrical mains power for providing operating power to the AAR controller circuitry;

the determining step comprises determining if the power supply is providing adequate operating power; and the alert issuing step comprises issuing a power supply error alert if the power supply is not providing adequate operating power.

29. The purging method of claim 28, wherein the power supply comprises redundant power supply circuits, and further comprising:

selecting an operable power supply circuit to provide operating power to the AAR controller.

30. The purging method of claim 28, wherein the AAR controller further comprises a backup battery for providing operating power to the AAR controller circuitry, and further comprising:

powering the AAR controller circuitry by power from the backup battery when the determining step determines that the power supply is not providing adequate operating power.

31. The purging method of claim 28, wherein the alert issuing step comprises issuing a backup battery alert if the AAR controller circuitry is powered by the backup battery.

32. The purging method of claim 31, further comprising:

inhibiting the step of opening the purge valve in response to an air sensor signal indicative of the presence of air in the air removal device housing when the AAR controller circuitry is powered by the backup battery; and wherein:

the AAR controller further comprises a mechanical release button interconnected with the purge valve adapted to enable manual opening of the purge valve by the perfusionist.

33. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:

providing an air removal device incorporated in the extracorporeal blood circuit, the air removal device comprising:

an air removal device housing enclosing a chamber;

an air removal device purge port through the housing to the chamber;

an air sensor supported by the air removal device housing; and an air removal device purge line coupled to the air removal device purge port extending to a purge line connector adapted to be coupled to a vacuum source to apply suction to the air removal device purge port to draw air therefrom;

locating a portion of the air removal purge line extending through a purge valve of an AAR controller, the purge valve movable between a purge valve open position and a purge valve closed position;

applying operating power to the air sensor to generate an air sensor signal indicative of the absence or presence of air in the air removal device housing;

opening the purge valve in response to an air sensor signal indicative of the presence of air in the air removal device housing to allow air sensed in the air removal device to be purged through the purge line by the suction of the vacuum source;

monitoring operations or conditions of the AAR system;

determining an error state of the monitored operations or conditions of the AAR system;

issuing an alert to alert the perfusionist of the error state; and wherein the alert issuing step comprises:

formulating alert sound signals related to the determined error state; and applying the formulated alert sound signals to a sound emitter that emits audible alert sounds that can be heard by the perfusionist.

34. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the method comprising:

providing an air removal device incorporated in the extracorporeal blood circuit, the air removal device comprising:

an air removal device housing enclosing a chamber;

an air removal device purge port through the housing to the chamber;

an air sensor supported by the air removal device housing; and an air removal device purge line coupled to the air removal device purge port extending to a purge line connector adapted to be coupled to a vacuum source to apply suction to the air removal device purge port to draw air therefrom;

locating a portion of the air removal purge line extending through a purge valve of an AAR controller, the purge valve movable between a purge valve open position and a purge valve closed position;

applying operating power to the air sensor to generate an air sensor signal indicative of the absence or presence of air in the air removal device housing;

opening the purge valve in response to an air sensor signal indicative of the presence of air in the air removal device housing to allow air sensed in the air removal device to be purged through the purge line by the suction of the vacuum source;

monitoring operations or conditions of the AAR system;

determining an error state of the monitored operations or conditions of the AAR system;

issuing an alert to alert the perfusionist of the error state; and wherein the alert issuing step comprises:

formulating alert light signals related to the determined error state; and applying the formulated alert light signals to at least one light emitter that emits visual light in response to the alert light signals that can be seen by the perfusionist.

35. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:

providing an air removal device incorporated in the extracorporeal blood circuit, the air removal device comprising:

an air removal device housing enclosing a chamber;
an air removal device purge port through the housing to the chamber;
an air sensor supported by the air removal device housing adapted to provide an air sensor signal indicative of air in the air removal device housing;
an air removal device purge line coupled to the air removal device purge port and extending to a purge line connector adapted to be coupled to a vacuum source to apply suction to the air removal device purge port to draw air therefrom;
providing an active air removal AAR controller operating under the control of an AAR operating algorithm;
locating a portion of the air removal purge line extending through a purge valve of the AAR controller, the purge valve movable between a purge valve open position and a purge valve closed position;
coupling the air sensor with the AAR controller;
monitoring operations or conditions of the AAR system;
determining an error state of the monitored operations or conditions of the AAR system;
automatically moving of the purge valve from the closed position to the open position in an absence of a determined error state and when the air sensor signal is indicative of air in the air removal device housing to allow air sensed in the air removal device to be purged through the purge line by the suction of the vacuum source; and
wherein the AAR controller operating system is powered by a power supply adapted to be coupled to mains power or by a backup battery, and further comprising:
determining if the power supply is operative and capable of supplying operating power to the AAR controller operating system;
determining if the backup battery is present and capable of supplying operating power to the AAR controller operating system; and
supplying operating power from the backup battery to the AAR controller operating system when the power supply is determined to be inoperative or incapable of supplying operating power to the AAR controller operating system and the backup battery is determined to be present and capable of supplying operating power to the AAR controller operating system.

36. The method of claim 35, further comprising alerting the perfusionist of the determined power state.

37. The operating method of claim 35, wherein the AAR controller further comprises a mechanical release button interconnected with the purge valve adapted to enable manual opening of the purge valve by the perfusionist.

38. The operating method of claim 35, further comprising disabling the automatic movement of the purge valve from the closed position to the open position when the air sensor signal is indicative of air in the air removal device housing if the power supply is determined to be inoperative or incapable of supplying operating power to the AAR controller operating system.

39. The operating method of claim 38, wherein the AAR controller further comprises a mechanical release button interconnected with the purge valve adapted to enable manual opening of the purge valve by the perfusionist.

40. The operating method of claim 35, wherein:
the purge valve comprises a pinch valve having a valve slot receiving the portion of the purge line and a pinch rod adapted to be moved between a purge valve closed position extending into the slot to compress the purge line and a purge valve open position retracted out of the slot; and
the purge valve opening step comprises moving the pinch rod from the purge valve closed position to the purge valve open position.

41. The operating method of claim 40, wherein the error state determining step comprises determining a pinch valve error state of the pinch valve.

42. The operating method of claim 41, wherein the pinch valve error state determining step comprises:
commanding the pinch rod to move into one of the pinch valve open and closed positions;
sensing the pinch rod position and providing a pinch rod position signal indicative of the actual position of the pinch rod; and
determining a position error state of the purge valve when the pinch rod position signal does not confirm that the pinch rod is in the commanded pinch valve open or purge valve closed position.

43. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:
providing an air removal device incorporated in the extracorporeal blood circuit, the air removal device comprising:
an air removal device housing enclosing a chamber;
an air removal device purge port through the housing to the chamber;
an air sensor supported by the air removal device housing adapted to provide an air sensor signal indicative of air in the air removal device housing;
an air removal device purge line coupled to the air removal device purge port and extending to a purge line connector adapted to be coupled to a vacuum source to apply suction to the air removal device purge port to draw air therefrom;
providing an active air removal AAR controller operating under the control of an AAR operating algorithm;
locating a portion of the air removal purge line extending through a purge valve of the AAR controller, the purge valve movable between a purge valve open position and a purge valve closed position;
coupling the air sensor with the AAR controller;
monitoring operations or conditions of the AAR system;
determining an error state of the monitored operations or conditions of the AAR system;
automatically moving of the purge valve from the closed position to the open position in an absence of a determined error state and when the air sensor signal is indicative of air in the air removal device housing to allow air sensed in the air removal device to be purged through the purge line by the suction of the vacuum source;
further comprising alerting the perfusionist of the determined error state; and
wherein the error state determining step comprises determining the presence of fluid in the purge line.

44. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:

providing an air removal device incorporated in the extracorporeal blood circuit, the air removal device comprising:
an air removal device housing enclosing a chamber;
an air removal device purge port through the housing to the chamber;
an air sensor supported by the air removal device housing adapted to provide an air sensor signal indicative of air in the air removal device housing;
an air removal device purge line coupled to the air removal device purge port and extending to a purge line connector adapted to be coupled to a vacuum source to apply suction to the air removal device purge port to draw air therefrom;
providing an active air removal AAR controller operating under the control of an AAR operating algorithm;
locating a portion of the air removal purge line extending through a purge valve of the AAR controller, the purge valve movable between a purge valve open position and a purge valve closed position;
coupling the air sensor with the AAR controller;
monitoring operations or conditions of the AAR system;
determining an error state of the monitored operations or conditions of the AAR system;
automatically moving of the purge valve from the closed position to the open position in an absence of a determined error state and when the air sensor signal is indicative of air in the air removal device housing to allow air sensed in the air removal device to be purged through the purge line by the suction of the vacuum source; and
wherein the AAR controller further comprises a fluid in line (FIL) sensor arranged with respect to the purge valve, and further comprising:
locating a further portion of the purge line through the FIL sensor; and
powering the FIL sensor to develop a FIL sensor signal indicative of the absence or presence of fluid in the purge line, and wherein:
the error state determining step comprises determining the presence of fluid in the purge line from the FIL sensor signal.

45. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:
providing an air removal device incorporated in the extracorporeal blood circuit, the air removal device comprising:
an air removal device housing enclosing a chamber;
an air removal device purge port through the housing to the chamber;
an air sensor supported by the air removal device housing adapted to provide an air sensor signal indicative of air in the air removal device housing;
an air removal device purge line coupled to the air removal device purge port and extending to a purge line connector adapted to be coupled to a vacuum source to apply suction to the air removal device purge port to draw air therefrom;
providing an active air removal AAR controller operating under the control of an AAR operating algorithm;
locating a portion of the air removal purge line extending through a purge valve of the AAR controller, the purge valve movable between a purge valve open position and a purge valve closed position;
coupling the air sensor with the AAR controller;
monitoring operations or conditions of the AAR system;
determining an error state of the monitored operations or conditions of the AAR system;
automatically moving of the purge valve from the closed position to the open position in an absence of a determined error state and when the air sensor signal is indicative of air in the air removal device housing to allow air sensed in the air removal device to be purged through the purge line by the suction of the vacuum source; and
wherein the error state determining step comprises determining the presence of fluid in the purge line.

46. The operating method of claim 45, wherein the AAR controller further comprises a mechanical release button interconnected with the purge valve adapted to enable manual opening of the purge valve by the perfusionist.

47. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:
providing an air removal device incorporated in the extracorporeal blood circuit, the air removal device comprising:
an air removal device housing enclosing a chamber;
an air removal device purge port through the housing to the chamber;
an air sensor supported by the air removal device housing adapted to provide an air sensor signal indicative of air in the air removal device housing;
an air removal device purge line coupled to the air removal device purge port and extending to a purge line connector adapted to be coupled to a vacuum source to apply suction to the air removal device purge port to draw air therefrom;
providing an active air removal AAR controller operating under the control of an AAR operating algorithm;
locating a portion of the air removal purge line extending through a purge valve of the AAR controller, the purge valve movable between a purge valve open position and a purge valve closed position;
coupling the air sensor with the AAR controller;
monitoring operations or conditions of the AAR system;
determining an error state of the monitored operations or conditions of the AAR system;
automatically moving of the purge valve from the closed position to the open position in an absence of a determined error state and when the air sensor signal is indicative of air in the air removal device housing to allow air sensed in the air removal device to be purged through the purge line by the suction of the vacuum source; and further comprising:
connecting an air sensor cable between the AAR controller and the air sensor; and
wherein the determining step determines if electrical continuity is present in the connection of the air sensor cable between the AAR controller and the air sensor.

48. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:

providing an air removal device incorporated in the extracorporeal blood circuit, the air removal device comprising:
  an air removal device housing enclosing a chamber;
  an air removal device purge port through the housing to the chamber;
  an air sensor supported by the air removal device housing adapted to provide an air sensor signal indicative of air in the air removal device housing;
  an air removal device purge line coupled to the air removal device purge port and extending to a purge line connector adapted to be coupled to a vacuum source to apply suction to the air removal device purge port to draw air therefrom;
providing an active air removal AAR controller operating under the control of an AAR operating algorithm;
locating a portion of the air removal purge line extending through a purge valve of the AAR controller, the purge valve movable between a purge valve open position and a purge valve closed position;
coupling the air sensor with the AAR controller;
monitoring operations or conditions of the AAR system;
determining an error state of the monitored operations or conditions of the AAR system;
automatically moving of the purge valve from the closed position to the open position in an absence of a determined error state and when the air sensor signal is indicative of air in the air removal device housing to allow air sensed in the air removal device to be purged through the purge line by the suction of the vacuum source; and
wherein the error state determining step comprises determining an error state of the air sensor.

49. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:
  providing an air removal device incorporated in the extracorporeal blood circuit, the air removal device comprising:
    an air removal device housing enclosing a chamber;
    an air removal device purge port through the housing to the chamber;
    an air sensor supported by the air removal device housing adapted to provide an air sensor signal indicative of air in the air removal device housing;
    an air removal device purge line coupled to the air removal device purge port and extending to a purge line connector adapted to be coupled to a vacuum source to apply suction to the air removal device purge port to draw air therefrom;
  providing an active air removal AAR controller operating under the control of an AAR operating algorithm;
  locating a portion of the air removal purge line extending through a purge valve of the AAR controller, the purge valve movable between a purge valve open position and a purge valve closed position;
  coupling the air sensor with the AAR controller;
  monitoring operations or conditions of the AAR system;
  determining an error state of the monitored operations or conditions of the AAR system;
  automatically moving of the purge valve from the closed position to the open position in an absence of a determined error state and when the air sensor signal is indicative of air in the air removal device housing to allow air sensed in the air removal device to be purged through the purge line by the suction of the vacuum source; and
  wherein the error state determining step comprises determining a low vacuum condition.

50. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:
  providing an air removal device incorporated in the extracorporeal blood circuit, the air removal device comprising:
    an air removal device housing enclosing a chamber;
    an air removal device purge port through the housing to the chamber;
    an air sensor supported by the air removal device housing adapted to provide an air sensor signal indicative of air in the air removal device housing;
    an air removal device purge line coupled to the air removal device purge port and extending to a purge line connector adapted to be coupled to a vacuum source to apply suction to the air removal device purge port to draw air therefrom;
  providing an active air removal AAR controller operating under the control of an AAR operating algorithm;
  locating a portion of the air removal purge line extending through a purge valve of the AAR controller, the purge valve movable between a purge valve open position and a purge valve closed position;
  coupling the air sensor with the AAR controller;
  monitoring operations or conditions of the AAR system;
  determining an error state of the monitored operations or conditions of the AAR system;
  automatically moving of the purge valve from the closed position to the open position in an absence of a determined error state and when the air sensor signal is indicative of air in the air removal device housing to allow air sensed in the air removal device to be purged through the purge line by the suction of the vacuum source; and
  wherein:
    the AAR controller further comprises a vacuum sensor arranged with respect to the purge line to provide a vacuum signal indicative of vacuum in the purge line;
    the error state determining step determines a low vacuum error state if the sensed vacuum falls below a minimum vacuum.

51. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:
  providing an air removal device incorporated in the extracorporeal blood circuit, the air removal device comprising:
    an air removal device housing enclosing a chamber;
    an air removal device purge port through the housing to the chamber;
    an air sensor supported by the air removal device housing adapted to provide an air sensor signal indicative of air in the air removal device housing;
    an air removal device purge line coupled to the air removal device purge port and extending to a purge line connector adapted to be coupled to a vacuum source to apply suction to the air removal device purge port to draw air therefrom;

providing an active air removal AAR controller operating under the control of an AAR operating algorithm;

locating a portion of the air removal purge line extending through a purge valve of the AAR controller, the purge valve movable between a purge valve open position and a purge valve closed position;

coupling the air sensor with the AAR controller;

monitoring operations or conditions of the AAR system;

determining an error state of the monitored operations or conditions of the AAR system;

automatically moving of the purge valve from the closed position to the open position in an absence of a determined error state and when the air sensor signal is indicative of air in the air removal device housing to allow air sensed in the air removal device to be purged through the purge line by the suction of the vacuum source; and wherein the error state determining step comprises determining a purge valve error state of the purge valve.

52. The operating method of claim 51, wherein the purge valve error state determining step comprises:

commanding the purge valve to move into one of the purge valve open and closed positions;

sensing the purge valve position and providing a purge valve position signal indicative of the actual position of the purge valve; and determining a position error state of the purge valve or the purge valve operating means when the sensed purge valve position signal does not confirm that the purge valve is in the commanded purge valve open position or purge valve closed position.

53. A method of operating an active air removal (AAR) system to purge air from an integrated extracorporeal blood circuit providing extracorporeal oxygenation of a patient's blood during cardiopulmonary bypass surgery adapted to be performed in the presence of a perfusionist on a patient in an operating room, the operating method comprising:

providing an air removal device incorporated in the extracorporeal blood circuit, the air removal device comprising:

an air removal device housing enclosing a chamber;

an air removal device purge port through the housing to the chamber;

an air sensor supported by the air removal device housing adapted to provide an air sensor signal indicative of air in the air removal device housing;

an air removal device purge line coupled to the air removal device purge port and extending to a purge line connector adapted to be coupled to a vacuum source to apply suction to the air removal device purge port to draw air therefrom;

providing an active air removal AAR controller operating under the control of an AAR operating algorithm;

locating a portion of the air removal purge line extending through a purge valve of the AAR controller, the purge valve movable between a purge valve open position and a purge valve closed position;

coupling the air sensor with the AAR controller;

monitoring operations or conditions of the AAR system;

determining an error state of the monitored operations or conditions of the AAR system;

automatically moving of the purge valve from the closed position to the open position in an absence of a determined error state and when the air sensor signal is indicative of air in the air removal device housing to allow air sensed in the air removal device to be purged through the purge line by the suction of the vacuum source; and wherein:

the AAR controller further comprises a vacuum sensor arranged with respect to the purge line to provide a vacuum signal indicative of vacuum in the purge line when the purge valve is closed; and the error state determining step comprises determining if the sensed vacuum exceeds a minimum vacuum.

\* \* \* \* \*

UNITED STATES PATENT AND TRADEMARK OFFICE
CERTIFICATE OF CORRECTION

PATENT NO. : 7,335,334 B2
APPLICATION NO. : 10/743599
DATED : February 26, 2008
INVENTOR(S) : Robert W. Olsen et al.

Page 1 of 1

It is certified that error appears in the above-identified patent and that said Letters Patent is hereby corrected as shown below:

In Column 44, Line 11, claim 22   ....the puree valve.... should be ....the purge valve....

Signed and Sealed this
First Day of May, 2012

David J. Kappos
*Director of the United States Patent and Trademark Office*